(12) United States Patent
Jagadeesan et al.

(10) Patent No.: US 11,890,063 B2
(45) Date of Patent: Feb. 6, 2024

(54) SYSTEM AND METHODS FOR A TRACKERLESS NAVIGATION SYSTEM

(71) Applicant: The Brigham and Women's Hospital, Inc., Boston, MA (US)

(72) Inventors: Jayender Jagadeesan, Boston, MA (US); Haoyin Zhou, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 342 days.

(21) Appl. No.: 17/414,640

(22) PCT Filed: Dec. 17, 2019

(86) PCT No.: PCT/US2019/066864
§ 371 (c)(1),
(2) Date: Jun. 16, 2021

(87) PCT Pub. No.: WO2021/131880
PCT Pub. Date: Jun. 25, 2020

(65) Prior Publication Data
US 2022/0051431 A1 Feb. 17, 2022

Related U.S. Application Data

(60) Provisional application No. 62/780,556, filed on Dec. 17, 2018.

(51) Int. Cl.
*A61B 34/20* (2016.01)
*A61B 1/00* (2006.01)
(Continued)

(52) U.S. Cl.
CPC .............. *A61B 34/20* (2016.02); *G06T 7/73* (2017.01); *G06T 17/00* (2013.01); *G06V 10/98* (2022.01);
(Continued)

(58) Field of Classification Search
CPC ........... G06T 17/00; G06T 2207/10021; G06T 2207/10056; G06T 2207/10068;
(Continued)

(56) References Cited

U.S. PATENT DOCUMENTS 9,763,748 B2 9/2017 Hummelink
10,033,985 B2 * 7/2018 Engedal ................. G06T 7/251
(Continued)

OTHER PUBLICATIONS

Amini et al., Augmented reality mastectomy surgical planning prototype using the HoloLens template for healthcare technology letters, 2019, pp. 261-265 (5 pages), vol. 6, Issue No. 6, Healthcare Technology Letters.

(Continued)

*Primary Examiner* — Daquan Zhao
(74) *Attorney, Agent, or Firm* — Quarles & Brady LLP

(57) ABSTRACT

Systems and methods for creating images of an environment includes controlling at least one camera to acquire imaging data from the environment and selecting, from the imaging data, a three-dimensional-two-dimensional correspondence as a control point for use in a perspective-n-point problem to determine a position and orientation of the at least one camera from n known correspondences between three-dimensional object points and their two-dimensional image projections in the environment. The method also includes reprojecting at least a selected number of the projections, determining a reprojection error for each of the projections, and performing a weight assignment of reprojection errors to distinguish the inliers form outliers. These steps of the method are repeated to apply the weight assignment to outliers in a decreased fashion during iterations to reduce an impact of outliers in the real-time display of the environment.

20 Claims, 59 Drawing Sheets

(51) Int. Cl.
*A61B 3/00* (2006.01)
*H04N 13/204* (2018.01)
*G06T 7/73* (2017.01)
*G06T 17/00* (2006.01)
*G06V 10/98* (2022.01)
*H04N 17/00* (2006.01)
*H04N 23/00* (2023.01)

(52) U.S. Cl.
CPC . *H04N 13/204* (2018.05); *G06T 2207/10021* (2013.01); *G06T 2207/10056* (2013.01); *G06T 2207/10068* (2013.01); *G06T 2207/30004* (2013.01); *G06T 2207/30244* (2013.01)

(58) Field of Classification Search
CPC . G06T 2207/30004; G06T 2207/30244; G06T 7/73; G06T 7/00; G06T 11/00; G06T 15/00; G06T 19/00; G06V 10/98; G06V 10/00; A61B 2034/2065; A61B 2090/365; A61B 2090/367; A61B 34/20; A61B 5/065; A61B 1/00; A61B 3/00; G09G 2380/08; H04N 13/204; H04N 17/00; H04N 23/00
USPC .......................................... 348/42, 45, 51, 61
See application file for complete search history.

(56) References Cited

U.S. PATENT DOCUMENTS

| | | |
|---|---|---|
| 2014/0121770 A1 | 5/2014 | Keyama |
| 2016/0098858 A1* | 4/2016 | Patkar .................... G06T 7/593 |
| | | 345/420 |
| 2017/0091945 A1 | 3/2017 | Vetterli et al. |
| 2017/0294020 A1* | 10/2017 | Crivella .................... G06T 7/33 |
| 2018/0350266 A1 | 12/2018 | Calderon |
| 2019/0099222 A1 | 4/2019 | Nahum |

OTHER PUBLICATIONS

Hummelink et al., Applications and limitations of using patient-specific 3D printed molds in autologous breast reconstruction, 2018, pp. 571-576 (6 pages), vol. 41, Issue No. 5, European journal of plastic surgery.

Melchels et al., CAD/CAM-assisted breast reconstruction, 2011, 17 pages, vol. 3, Issue No. 3, Document No. 034114, Biofabrication.

Ogunleye et al., The utility of three-dimensional models in complex microsurgical reconstruction, 2020, pp. 428-434 (7 pages), vol. 47, Issue No. 05, Archives of plastic surgery.

PCT International Search Report and Written Opinion, PCT/US2019/066864, dated Jun. 25, 2020, 12 pages.

Tomita et al., DIEP flap breast reconstruction in patients with breast ptosis: 2-stage reconstruction using 3-dimensional surface imaging and a printed mold, 2017, 4 pages, vol. 5, Issue No. 10, Plastic and Reconstructive Surgery Global Open.

Tomita et al., DIEP Flap Breast Reconstruction Using 3-dimensional Surface Imaging and a Printed Mold, Mar. 2015, 5 pages, vol. 3, Issue 3, Plastic and Reconstructive Surgery—Global Open.

Zhou et al., Real-time dense reconstruction of tissue surface from stereo optical video, 2019, 36 pages, vol. 39, Issue No. 2, IEEE transactions on medical imaging.

* cited by examiner

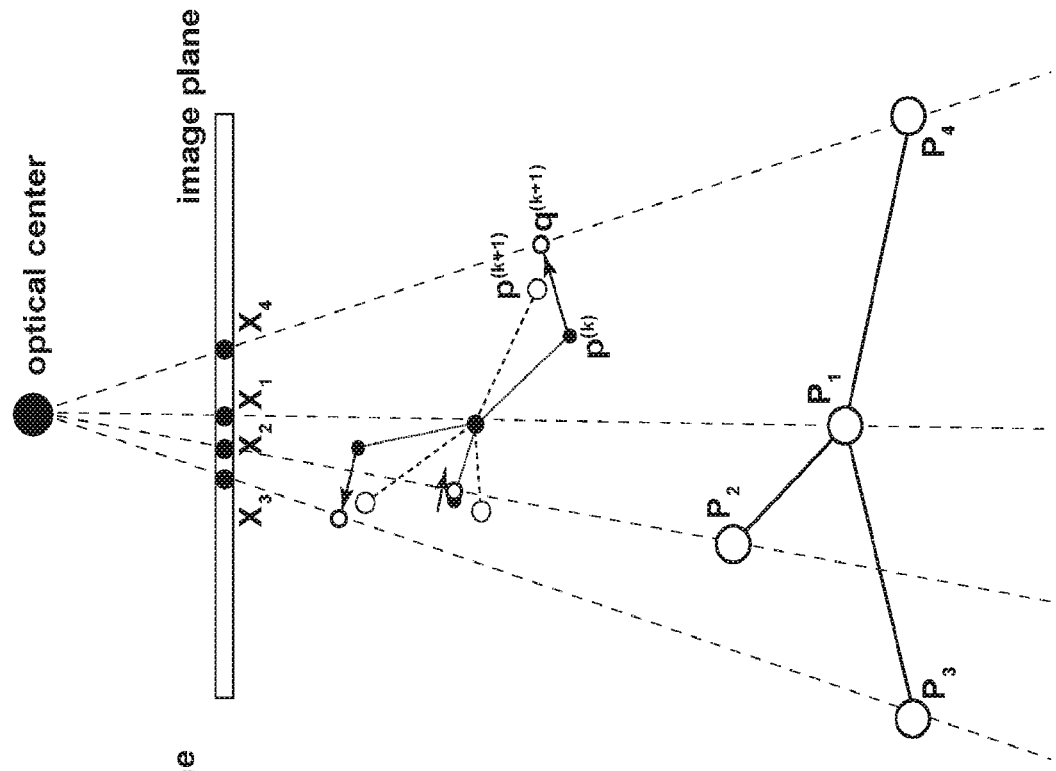
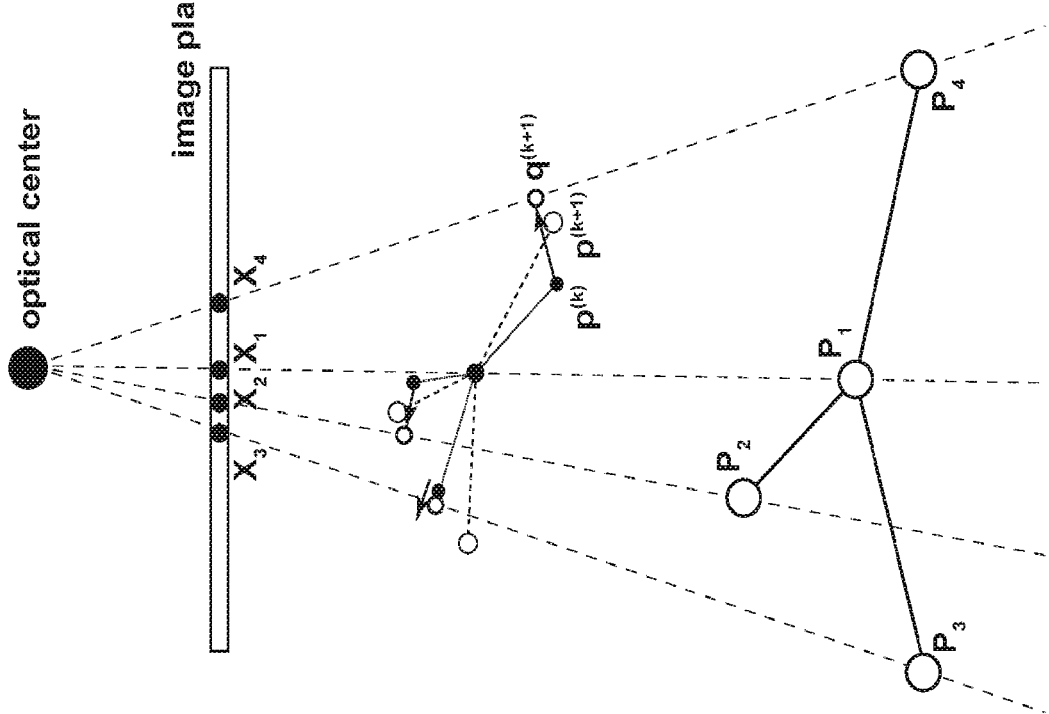
FIG. 4A
FIG. 4B

200

```
trials = 0;
RANSAC try different reference o until [RANSAC termination condition Eq. (25) ]
      k = 0;
      do until [Iteration termination condition A Eq. (26) ]    ⎫
            R1PPnP iterations with re-weighting mechanism;      ⎬  to detect as many
            k = k+1;                                            ⎭  inliers as possible
      end
      trials = trials + 1;
end
k = 0;
do until [Iteration termination condition B Eq. (27) ]   ⎫  Refinement: to make
      R1PPnP iterations without re-weighting mechanism;  ⎬  pose estimation more
      k = k+1;                                           ⎪  accuate based on inliers
end                                                      ⎭  already detected
```

FIG. 6

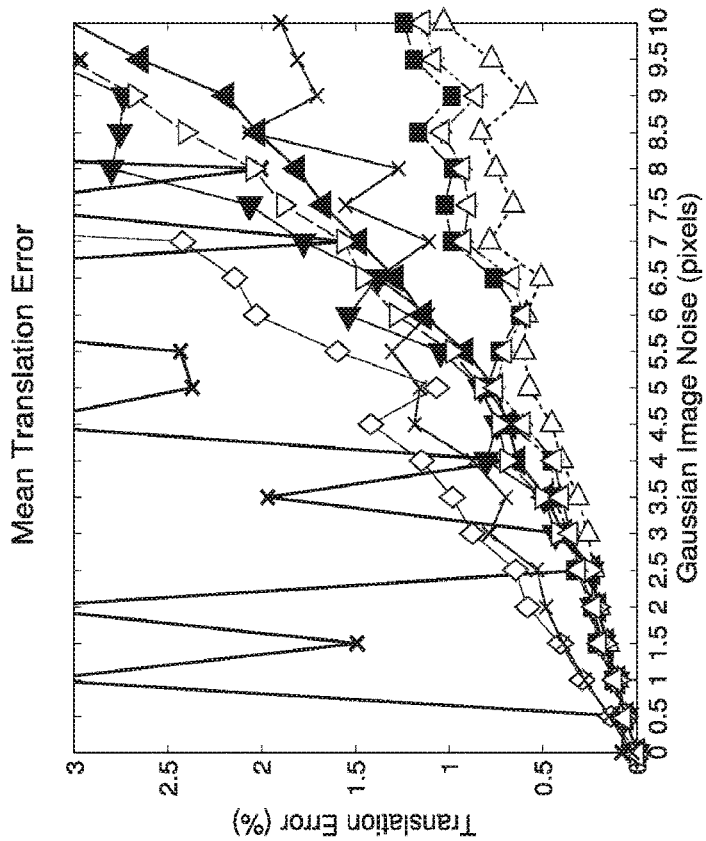
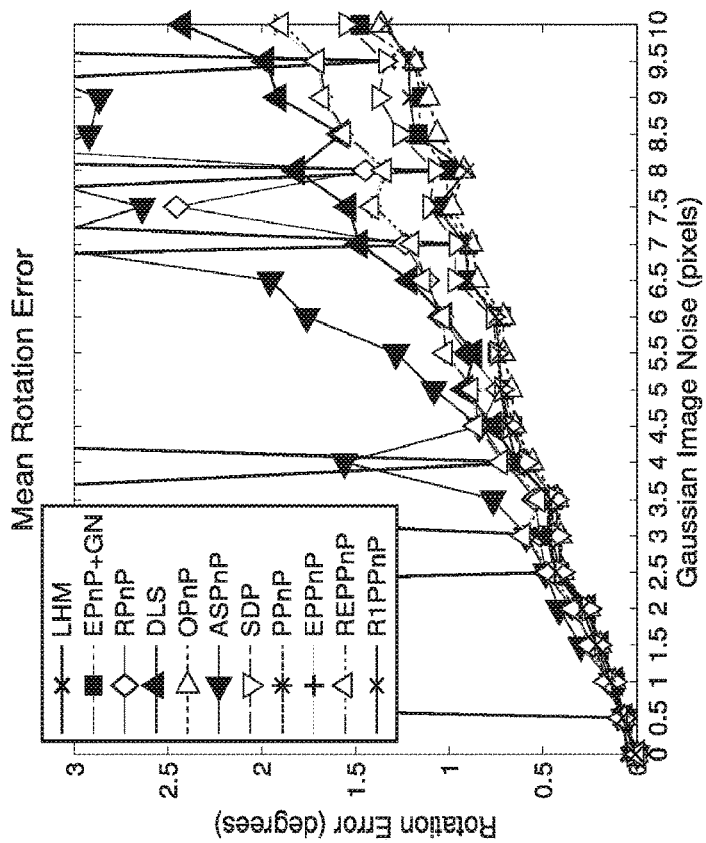
FIG. 10A
FIG. 10B

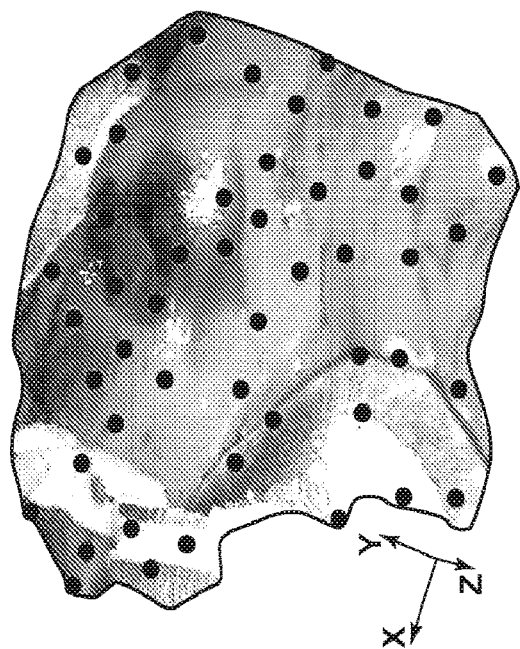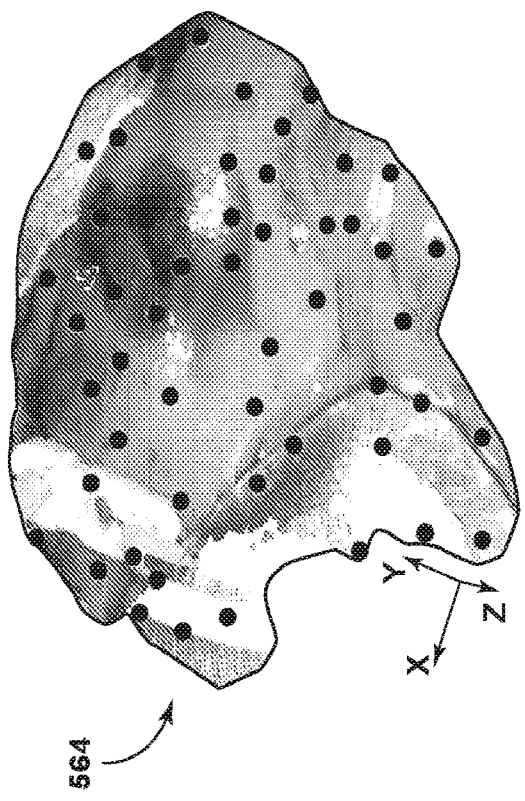
FIG. 27D

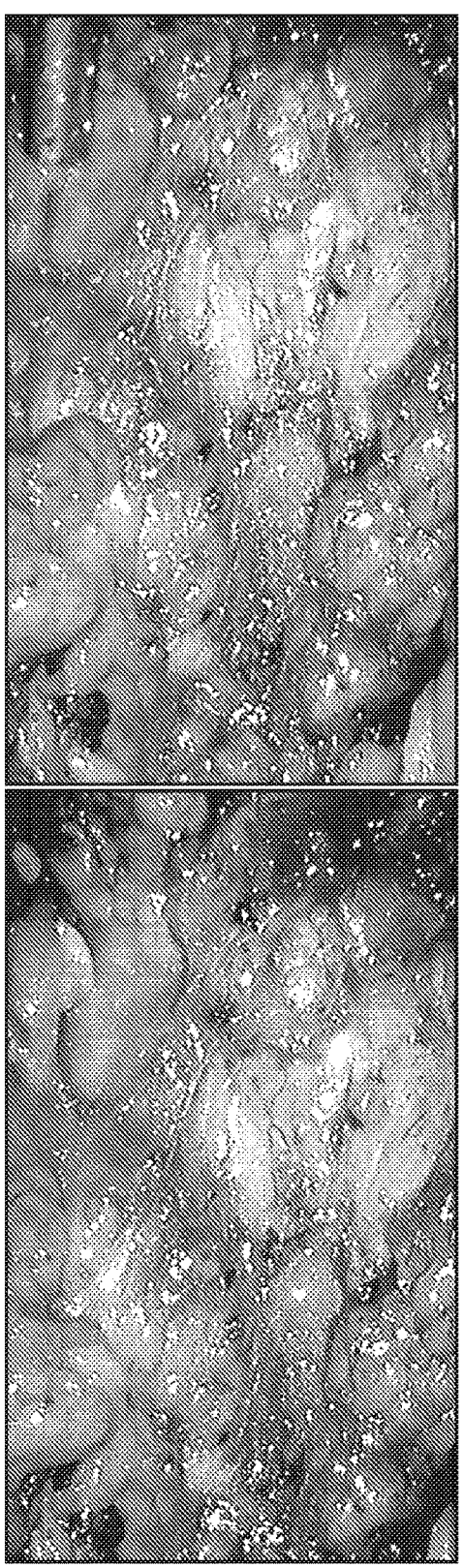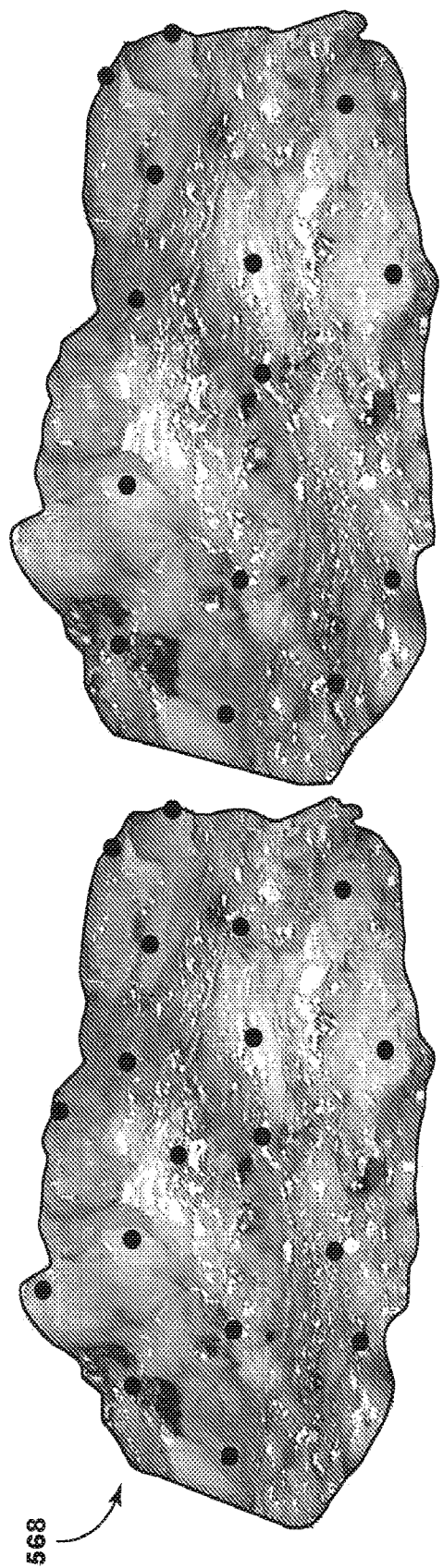
FIG. 27E

SYSTEM AND METHODS FOR A TRACKERLESS NAVIGATION SYSTEM

CROSS-REFERENCE TO RELATED APPLICATIONS

This application is based on, claims the benefit of, and incorporates herein by reference, U.S. Provisional Patent Application Ser. No. 62/780,556, filed on Dec. 17, 2018 and entitled "SYSTEM AND METHODS FOR A TRACKERLESS NAVIGATION SYSTEM."

STATEMENT REGARDING FEDERALLY SPONSORED RESEARCH

This invention was made with government support under K99EB027177, R01EB025964, P41EB015898, P41RR019703, and R01DK119269 from the National Institutes of Health. The government has certain rights in the invention.

BACKGROUND

The present disclosure relates generally to systems and methods for a trackerless navigation. The systems and methods provided herein have wide applicability, for example, including guided medical, such as surgical, or industrial or other exploratory procedures. Such medical procedures may include laparoscopic surgical procedures and other minimally invasive surgical or robotic procedures.

The perspective-n-point (PnP) problem aims to determine the position and orientation of a calibrated camera from n known correspondences between three-dimensional (3D) object points and their two-dimensional (2D) image projections. PnP is a core problem in the computer vision field and has found many applications, such as robot vision navigation, augmented reality, and computer animation. In the past decades, many effective PnP approaches have been proposed with very fast computational speed and high accuracy.

To date, most PnP algorithms are designed under the assumption that no outlier exists among the given three-dimensional-two-dimensional (3D-2D) correspondences. However, in practical applications, this outlier-free assumption is often difficult to satisfy. This is because image feature detection and matching approaches, such as SURF, BRISK and ORB, do not always give perfect results due to scaling, illumination, shadow, occlusion, and other confounding or complicating factors. Outliers are often unavoidable and they can have a significant impact on the PnP methods. Even a small percentage of outliers can lead to a significant decrease in accuracy. Hence, the ability to handle outliers is important for extending PnP algorithms into practical applications, particularly, those that necessitate or benefit from accuracy and precision.

As just one example, consider medical procedures. A surgeon's visualization during surgery is typically limited to the anatomical tissue surface exposed to him/her through an optical imaging modality, such as a laparoscope, endoscope, or microscope. As a result, intraoperative identification of the critical structures lying below the visual surface is difficult and could lead to inadvertent complications during the surgery. Direct registration between two-dimensional (2D) optical (microscopy, endoscopy or laparoscopy) videos and three-dimensional (3D) magnetic resonance (MR), computed tomography (CT), ultrasound, optical, or other images is difficult and highly non-trivial.

For example, laproscopes, endoscopes, and microscopes are some of the most common tools for performing minimally invasive surgical procedures. In these cases, tissue visualization during surgery is typically limited to the anatomical surface exposed to the surgeon through an optical imaging modality, such as laparoscope, endoscope or microscope. To identify the critical structures lying below the tissue surface, surgical navigation systems need to register the intraoperative data to preoperative MR/CT imaging before performing the surgical procedure. However, during surgery, tissue deformation caused by heartbeat, respiration, instruments interaction, or patient movements may make the initial registration results less accurate.

Accordingly, there is a substantial need for improved navigation and guidance systems and methods, such as for use in surgical procedures and other applications.

SUMMARY

The present disclosure overcomes the aforementioned drawbacks by providing robust and efficient trackerless navigation system and methods that can be used in challenging applications such as navigation in the face of non-rigid movement, such as tissue deformation.

In one aspect, the present disclosure provides a system for navigating an environment experiencing non-rigid motion. The system includes at least one imaging system including at least one camera configured to acquire imaging data from the environment. The system includes a processor configured to receive the imaging data from the at least one camera and programmed to provide a real-time display of the environment experiencing the non-rigid motion by (i) selecting, from the imaging data, a three-dimensional-two-dimensional (3D-2D) correspondence as a control point for use in a perspective-n-point (PnP) problem to determine a position and orientation of the at least one camera from n known correspondences between 3D object points and their 2D image projections in the environment, (ii) reprojecting at least a selected number of the projections, (iii) determining a reprojection error for each of the projections, (iv) performing a weight assignment of reprojection errors to distinguish inliers and outliers, (v) repeating (i) through (iv) multiple times, the weight assignment applied to outliers being decreased during iterations to reduce the impact of outliers in the real-time display of the environment. The system includes a display configured to display the real-time display of the environment experiencing the non-rigid motion.

In another aspect, the present disclosure provides a method for creating images of an environment experiencing non-rigid motion. The method includes steps including (a) controlling at least one camera to acquire imaging data from the environment, (b) selecting, from the imaging data, a three-dimensional-two-dimensional (3D-2D) correspondence as a control point for use in a perspective-n-point (PnP) problem to determine a position and orientation of the at least one camera from n known correspondences between 3D object points and their 2D image projections in the environment, (c) reprojecting at least a selected number of the projections, (d) determining a reprojection error for each of the projections, (e) applying a histogram voting process to select inliers, (f) performing a weight assignment of reprojection errors to distinguish the inliers form outliers, iteratively repeating steps (a)-(f), the weight assignment applied to outliers being decreased during iterations to reduce an impact of outliers in the real-time display of the environment, and displaying the images of the environment experiencing the non-rigid motion in real-time.

In yet another aspect, the present disclosure provides a method for creating images of an environment experiencing non-rigid motion. The method includes steps including (a) controlling at least one camera to acquire imaging data from the environment, (b) selecting, from the imaging data, a three-dimensional-two-dimensional (3D-2D) correspondence as a control point for use in a perspective-n-point (PnP) problem to determine a position and orientation of the at least one camera from n known correspondences between 3D object points and their 2D image projections in the environment, (c) reprojecting at least a selected number of the projections, (d) determining a reprojection error for each of the projections, (e) performing a weight assignment of reprojection errors to distinguish the inliers form outliers, iteratively repeating steps (a)-(e), the weight assignment applied to outliers being decreased during iterations to reduce an impact of outliers in the real-time display of the environment, and displaying the images of the environment experiencing the non-rigid motion in real-time.

BRIEF DESCRIPTION OF THE DRAWINGS

FIG. 4A is an illustration of a first step of a iterative process with two-dimensional (2D) space and one-dimensional (1D) camera imaging plane.

FIG. 4B is an illustration of a second step of the iterative process of FIG. 4A.

FIG. 6 is pseudocode that generally illustrates a process that uses the R1PPnP algorithm to estimate a pose.

FIG. 10A is a graph of mean rotation error in degrees vs. Gaussian image noise in pixels for various PnP methods used with outlier-free synthetic data for quasi-singular cases.

FIG. 10B is a graph of mean translation error as a percent vs. Gaussian image noise in pixels for the PnP methods used in FIG. 9A on outlier-free synthetic data for quasi-singular cases.

FIG. 27D is a set of input video frames of Hamlyn in vivo data with respiration and heartbeat along with a corresponding set of deformed templates including dots representing control points.

FIG. 27E is a set of input video frames of in vivo kidney data with deformation caused by respiration along with a corresponding set of deformed templates including dots representing control points.

DETAILED DESCRIPTION

Figure 1:
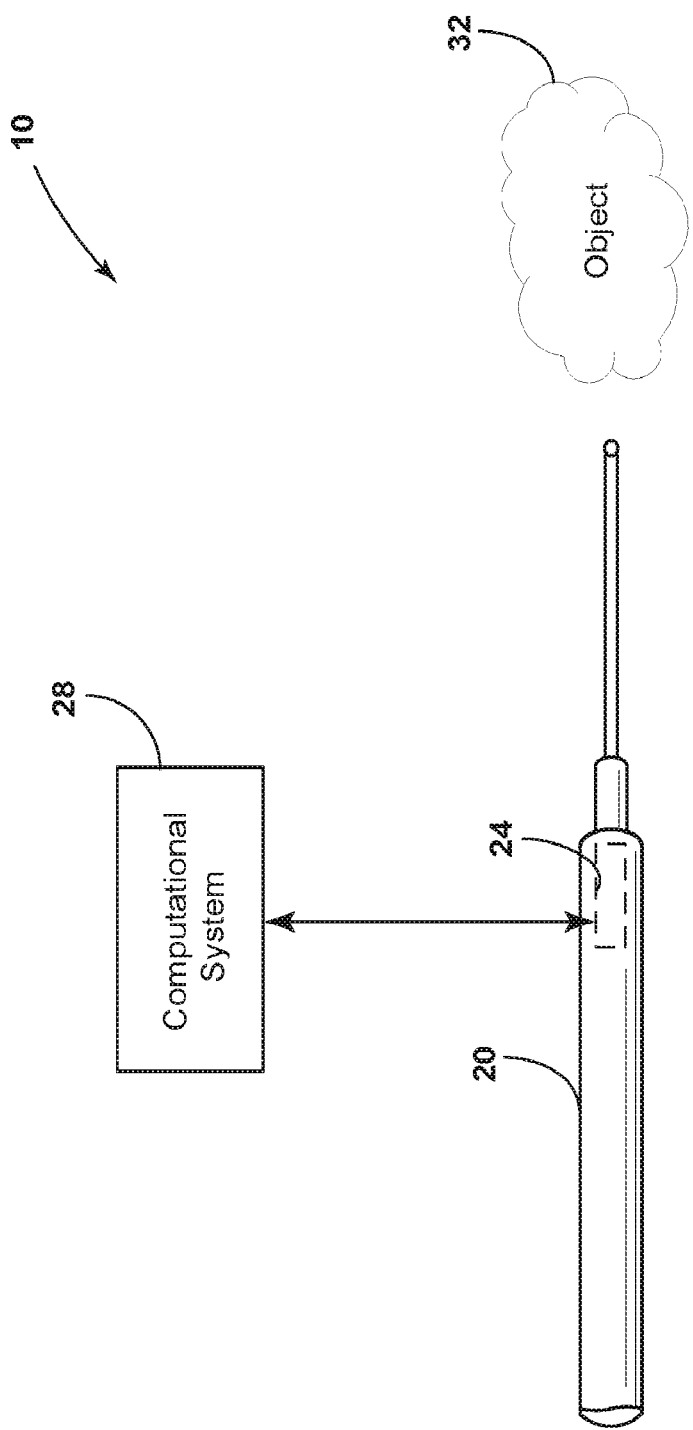
FIG. 1 is a diagram of an exemplary system for use in a surgical setting.

Referring to FIG. 1, an exemplary system 10 for use in a surgical setting is shown. The system 10 can include a device 20, which as one non-limiting example may include an imaging system 24 capable of generating videos and/or pictures. The imaging system may be a stereoscopic imaging system that uses two camera lenses. In one non-limiting example, the imaging system 24 can include a laparoscope, endoscope, microscope, or other interventional system. The imaging system 24 can be coupled to and in communication with a computational system 28. Images or video may be transmitted to the computational system 28 for processing and/or to receive commands from the computational system 28. The computational system 28 can include at least one processor and at least one memory, and may be a controller, desktop computer, laptop, tablet computer, smartphone, or other suitable computational device. The imaging device 20 is designed to image a target or object 32. In the non-limiting example of a medical procedure, the target or object 32 may be tissue and the imaging device 20 can acquire images or video of the tissue. The tissue may include organs, such as kidneys, livers, spines, hearts, lungs, breasts, or other suitable tissues. The system 10 can be used to implement at least a portion of the imaging and reconstruction techniques described below, even when used in an environment that includes non-rigid motion, such as tissue deformation or physiological motion.

One mechanism for handling outliers is to combine a perspective-n-point (PnP) (n=3 or 4) algorithm with the random sample consensus (RANSAC)-based scheme to eliminate outliers, and then perform a more accurate PnP algorithm with the remaining inliers to refine the result. A number of very fast closed-form P3P or P4P algorithms have been proposed. However, their RANSAC combination scheme still needs many trials until the selected three or four three-dimensional-two-dimensional (3D-2D) correspondences are all inliers, which results in a high time complexity. Hence, the computational speed decreases significantly as the percentage of outliers increases. To reduce the time complexity, one can utilize the PnP algorithm with a smaller n. However, when n=1 or 2, the PnP problem has infinitely many solutions, which makes the conventional RANSAC-based scheme infeasible.

Beyond RANSAC-based methods, REPPnP is a method proposed by some to address outliers. REPPnP integrates an outlier rejection mechanism with camera pose estimation. It formulates the pose estimation problem as a low-rank homogeneous system in which the solution lies on its one-dimensional (1D) null space. Outlier correspondences are those rows of the linear system that perturb the null space and are progressively detected by projecting them on an iteratively estimated solution of the null space. Although REPPnP is very fast and accurate, it suffers from a severe limitation that it cannot handle more than approximately 50% of outliers. Thus, these attempts to address outliers fails in many applications, including, for example, surgical or medical procedures that demand accuracy and precision.

The present disclosure provides systems and methods that overcome these shortcomings, and can be implemented, for example, using the system of FIG. 1, or others. In particular, a robust 1-point RANSAC-based PnP method is provided herein that will be referred to herein as R1PPnP. As set forth below, an optimal iterative process is described as part of the PnP algorithm of R1PPnP. This algorithm takes a random 3D-2D correspondence as the control point. To address outliers, a soft weight assignment method is provided that uses reprojection errors to distinguish inliers and outliers, and integrate it into the algorithm. The weight factors associated with outliers decrease significantly during the iteration to reduce the impact of outliers. Finally, the 1-point RANSAC scheme can be used to try different control points for the PnP algorithm. By using this combination of the RANSAC scheme and the soft weight assignment, the overall algorithm is capable of eliminating outliers using a selected control point that is an inlier.

As will be described, the R1PPnP method has much lower time complexity and is much faster than conventional RANSAC+P3P or P4P methods, especially when the percentage of outliers is large. Compared with REPPnP, the R1PPnP methods described herein do not suffer from the percentage of outliers limitation.

The below sections are organized in a plurality of sections. First, in the "Model" section, the fundamental model used in R1PPnP is described. The details of the algorithm are given in the "Core Algorithm Design" section, in which proof of convergence, local minima analysis, and the strategy to select control points is described. The outliers handling mechanism, including soft weight assignment and the 1-point RANSAC scheme, is introduced in the "Outliers Handling Mechanism" section. Details of termination conditions is provided in the "Outliers Handling Mechanism" section. Evaluation results are presented in a section labeled "Experiments".

The PnP problem, coined by Fischler and Bolles, is articulated as follows. Given the relative spatial locations of n control points, and given the angle to every pair of control points $P_i$ from an additional point called the center of perspective C, find the lengths of the line segments joining C to each of the control points. The PnP problem has been studied for many years. In early studies, direct linear transformation (DLT) was used as a solution in a straightforward way by solving a linear system. However, DLT ignores the intrinsic camera parameters, which are assumed to be known, and therefore generally leads to a less stable pose estimate.

In the past decade, researchers have proposed many PnP methods to improve speed, accuracy, and robustness to outliers. As mentioned, the PnP methods can be roughly classified into non-iterative and iterative methods. Generally speaking, non-iterative methods are more efficient but are unstable under image noise and outliers. Many non-iterative PnP methods are based on a set of small number of points (n=3,4). They are referred to as P3P or P4P methods. P3P is the smallest subset of control points that yields a finite number of solutions. When the intrinsic camera parameters are known and we have n≥4 points, the solution is generally unique. Triggs proposed a PnP method with four- or five-correspondences. These PnP methods based on less than four correspondences do not make use of redundant points and are very sensitive to noise and outliers. However, due to their efficiency and capability to calculate from a small point set, P3P or P4P methods are very useful for combing a RANSAC-like scheme to reject outliers. There are also many non-iterative PnP methods that are able to make use of redundant points but are quite time consuming. For example, Ansar's method is $O(n^8)$ and Fiore's is $O(n^2)$. Schweighofer proposed an $O(n)$ PnP method named SDP, but is slow. In recent years, three excellent $O(n)$ effective non-iterative PnP methods, EPnP, RPnP and UPnP, have been proposed, and these methods are very efficient and accurate even compared to iterative methods.

Iterative PnP methods are mostly optimization methods that decrease their energy function in the iterative process. They are generally more accurate and robust, but slower. For example, Dementhon proposed POSIT that is easy to implement and further proposed SoftPOSIT to handle situations when the correspondence relationships are unknown. Although SoftPOSIT has a certain ability to handle outliers, the strong assumption that all correspondences are unknown make it slow. Lu's method is the most accurate iterative P n P method but may get stuck in local minima. Schweighofer discussed the local minima situation of Lu's method and proposed a method to avoid this limitation.

PnP algorithms are widely used in applications such as structure from motion and monocular simultaneous localization and mapping (SLAM), which require dealing with hundreds or even thousands of noisy feature points and outliers in real-time. The fact that outliers have a much greater impact on PnP accuracy than image Gaussian white noise makes it is necessary for the PnP algorithm to handle outliers efficiently. Conventional method to handle outliers is to combine a RANSAC-like scheme with the P3P or P4P algorithms. Besides, L1-norm is also widely used to handle a certain amount of outliers because the L1-norm penalty is less sensitive to outliers than the L2-norm penalty. Although a L1-norm-based energy function is more robust to outliers, it cannot absolutely get rid of outliers and its computation is more complex. Some proposed a very fast PnP method that can handle up to 50% of outliers. The outlier rejection mechanism is integrated within the pose estimation pipeline with negligible computational overhead. Compared to that method, the R1PPnP algorithm described herein demonstrates much stronger robustness and can be used in applications where the predecessors fail.

Model

As described herein, the camera frame will be denoted as c and the world frame will be denoted as w. For point i, without taking into account the distortion, the perspective projection equations are employed to describe the pinhole camera model, $$u_i = f\frac{x_i^c}{z_i^c}, v_i = f\frac{y_i^c}{z_i^c}, \quad (1)$$

where f is the camera focal length, $x_i=[u_i, v_i, f]^T$ is the image homogeneous coordinate in pixels, and $X_i^c=[x_i^c, y_i^c, z_i^c]^T$ is the real-world coordinate with respect to the camera frame.

According to Equation (1), $$X_i^c = \lambda_i^* x_i, \quad (2)$$

where $\lambda_i^* = z_i^c/f$ is the normalized depth of point i. Equation (2) indicates that an object point lies on the straight line of sight of the related image point.

The relationship between the camera and world frame coordinate of point i is $$X_i^c = RX_i^w + t, \quad (3)$$

where $R \in SO(3)$ is the rotation matrix and $t \in R^3$ is the translation vector. R and t are the variables that need to be estimated in the PnP problem.

Similarly to the translation elimination method used in works, with two points i and o, $$X_i^c - X_o^c = R(X_i^w - X_o^w), i \neq o. \quad (4)$$

In the proposed R1PPnP algorithm, $o \in [1,N]$ suggests the index of the control point, N is the number of 3D-2D correspondences. R1PPnP represents the shape of the point cloud by the relative positions between the control point o and other N-1 points. Denoting $S_i = X_i^w - X_o^w$, where S means "shape", then, according to Equation (2) and Equation (4), $$\lambda_i^* x_i - \lambda_o^* x_o = RS_i. \quad (5)$$

Divising both sides of Equation (5) by the depth of the control point $\lambda_o^*$, allows Equation (5) to be rewritten as $$\lambda_i x_i - x_o = \mu RS_i, \quad (6)$$

where $\lambda_i = \mu \lambda_i^*$ and $\mu = 1/\lambda_o^*$ is the scale factor. This provides $$t = 1/\mu x_o - RX_o^w \quad (7)$$

According to Equation (6) and Equation (7), the PnP problem can be solved by minimizing the objective function $$f(R, \mu, \lambda_i) = \Sigma_{i=1, i \neq o}^N \|\lambda_i x_i - x_o - \mu RS_i\|^2, \quad (8)$$

where $\|\cdot\|$ is the L2-norm.

The objective function Equation (8) is based on Euclidean distances in the 3D space. Compared with the reprojection error cost, Equation (8) gives more weights to points with larger depths. For example, the same level of reprojection error has relatively larger effects when related to an object point with greater depth. To solve this problem, the cost function Equation (8) can be normalized with depths of points and the objective function of R1PPnP algorithm is provided as $$f(R, \mu, \lambda_i) = \sum_{i=1, i \neq o}^N \left(\frac{1}{\lambda_i}\|\lambda_i x_i - x_o - \mu RS_i\|\right)^2, \quad (9)$$

where $1/\lambda_i$ is introduced to adjust the weight of point i to eliminate the inequity among points in Equation (8). We estimate R, $\mu$ and $\lambda_i$ (i=1, ..., N, i≠o) by minimizing the objective function Equation (9), the variables of which consist of two parts: the camera pose {R, $\mu$} and the relative depths with respect to the control point {$\lambda_i$}. To describe the following algorithm intuitively, we introduce two sets of points: $p_i$ and $q_i$. With a randomly selected control o, points $p_i$ are determined by the camera pose {R, $\mu$}, and points $q_i$ are determined by depths $\lambda_i$. We have $$p_i = x_o + \mu RS_i, \quad (10)$$

$$q_i = \lambda_i x_i. \quad (11)$$

Figure 2:
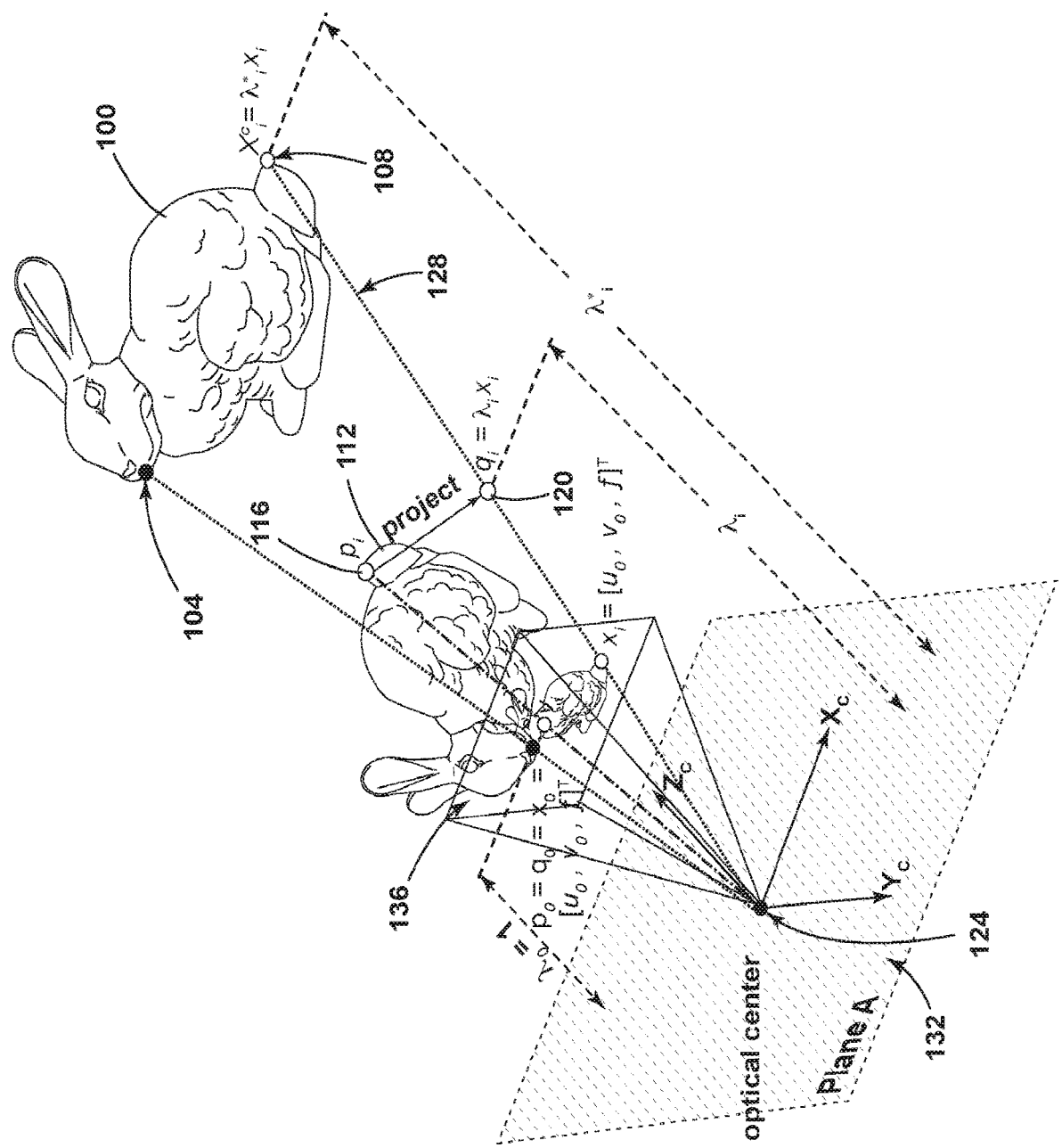
FIG. 2 is an illustration of geometrical relationships with a bunny model.

FIG. 2 is an illustration of geometrical relationships with a bunny model. The mouth point of a real object 100 is a control point o (marked with 104). In algorithm, all virtual points rotate and scale around the control point 104 with $p_o = q_o = x_o$. We use a tail point 108 to exemplify $p_i$ (marked with 116) and its projection $q_i$ (marked with 120). Plane A 132 is parallel to the imaging plane 136 and passes the camera optical center 124. Without loss of generality and for clearer demonstration, in FIG. 2 we use focal length f=1 and all depths are distances between points and plane A.

As shown in FIG. 2, points $p_i$ are attached with a virtual object 112 obtained by rotating and scaling the real object around the control point $p_o = q_o = x_o \cdot q_i$ is the projection of $p_i$ on the corresponding line of sight 128. The objective function Equation (9) is equivalent to $$f(p_i, q_i) = \sum_{i=1, i \neq o}^{N} \left(\frac{1}{\lambda_i} \|p_i - q_i\|\right)^2 \quad (12)$$

As this objective function approaches the global optimal solution and as shown in FIG. 2, point $p_i$ gets close to $q_i$ and the z-component of $p_i$ gets close to $f\lambda_i$. Hence, it is expected that the objective function Equation (12) has similar optimal solutions as the conventional reprojection error cost, because $$f(p_i, q_i) = \sum_{i=1, i \neq o}^{N} \left\| \left[\frac{p_{i,x}}{\lambda_i}, \frac{p_{i,y}}{\lambda_i}, \frac{p_{i,z}}{\lambda_i}\right]^T - x_i \right\|^2 \approx \quad (13)$$

$$\sum_{i=1, i \neq o}^{N} \left\| \left[f\frac{p_{i,x}}{p_{i,z}}, f\frac{p_{i,y}}{p_{i,z}}, f\right]^T - [u_i, v_i, f]^T \right\|^2$$

Core Algorithm Design

We first introduce the core algorithm of R1PPnP, which can be used to solve the P n P problem in outlier-free situations. This section introduces the core algorithm process, proof of convergence, the local minima avoidance mechanism, and the strategy to select the control point.

The core algorithm of R1PPnP is an optimal iterative process with the objective function Equation (9) or Equation (12). In each iteration, it estimates the points set $q_i$ and $p_i$ (i=1, . . . , N, i≠o) alternately by fixing one points set and updating the other one according to the objective function minimization.

(1) $q_i$ Estimation Stage.

Because each $q_i$ are independent with each other, our algorithm seeks the closest $q_i$ for each $p_i$. According to Equation (11), points $q_i$ are constrained to the related lines of sight. Hence, we vertically project $p_i$ onto the related lines of sight to obtain the points' relative depths with respect to the control point o by $$\lambda_i = x_i^T p_i/(x_i^T x_i), i=1, \ldots, N \text{ and } i \neq o. \quad (14)$$

Then, points $q_i$ are updated according to Equation (11).

(2) $p_i$ Estimation Stage.

Points $p_i$ are determined by R and µ. According to Equation (10), the updated R and µ should make points $\{\mu RS_i\}$ have the smallest weighted sum of squared distances to points $\{q_i-x_o\}$, and subject to $R^T R = I_{3 \times 3}$. According to the objective function Equation (12), the weights used in this stage are $1/\lambda_i$ in the previous iteration.

Denoting matrices $$A = \left[\frac{q_1 - x_o}{\lambda_1}, \ldots, \frac{q_N - x_o}{\lambda_N}\right]_{3 \times N} \text{ and }$$

$$S = \left[\frac{S_1}{\lambda_1}, \ldots, \frac{S_N}{\lambda_N}\right]_{3 \times N},$$

then according to $$[U, \Sigma, V^T] = svd(AS^T), R = UV^T, \quad (15)$$

Figure 3:
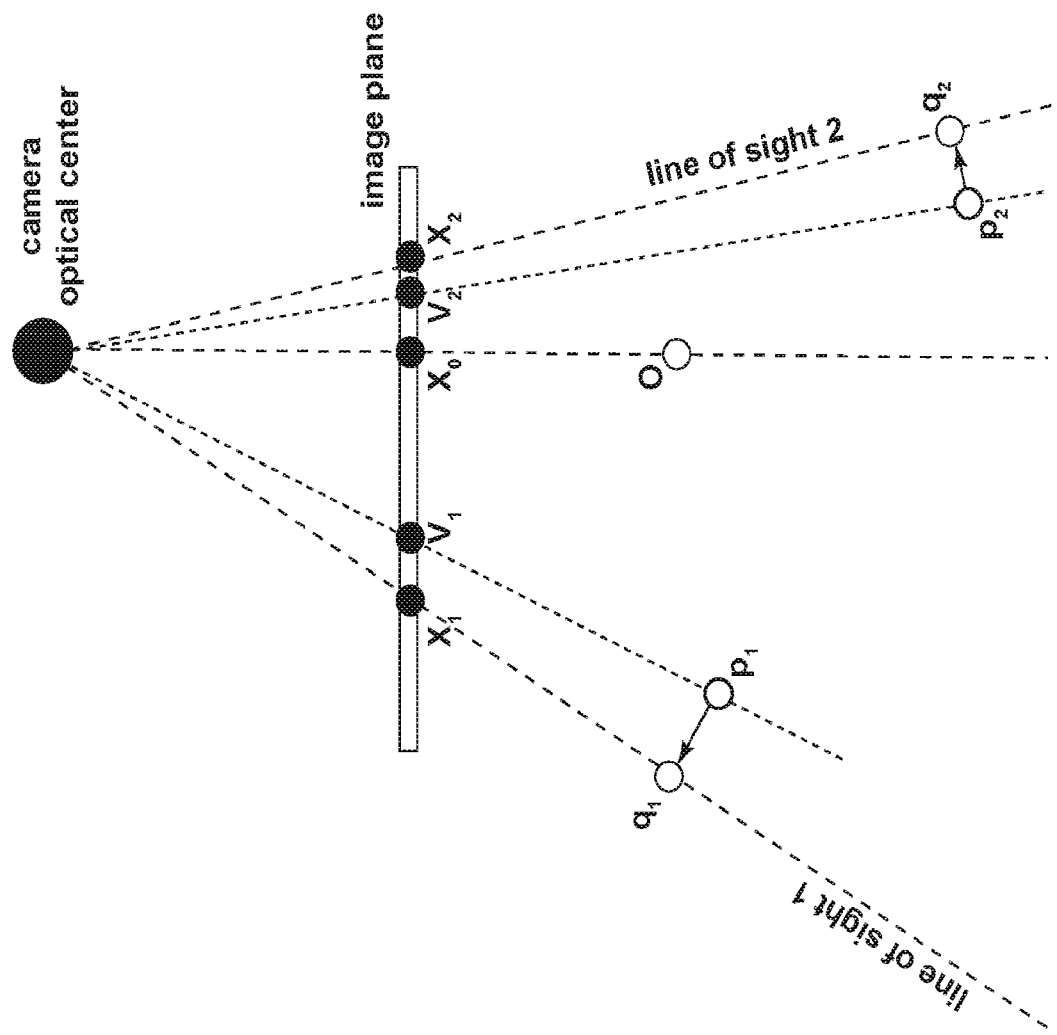
FIG. 3 is an illustration of the updating method of the scale factor $\mu$.

FIG. 3 is an illustration of the updating method of the scale factor µ. One possible method is to update µ according to the Euclidean distances between $p_i$, $q_i$ and o, which works for $p_1$ and $q_1$ because they have close depths as o. However, this method may result in slow µ updating rate for $p_2$ and $q_2$ because $\|q_2-o\| \approx \|p_2-o\|$. Hence, it is more efficient to compare $v_i$ and $x_i$ to move points $p_i$ to the related lines of sight.

Because points $p_i$ are directly generated from $S_i$ according to Equation (10), Equation (15) suggests that R is updated according to the differences between points $p_i$ and $q_i$ in the 3D space. However, FIG. 3 demonstrates that by using this method, the updating rate of µ may be slow in situations when the range of depths is large. To achieve faster convergence rate, we update the scale factor µ by comparing the projected image coordinates of $p_i$, which are denoted as $v_i$, and the real image points $x_i$. Denoting matrices $B=[v_1-x_o, \ldots, v_N-x_o]_{3 \times N}$ and $C=[x_1-x_o, \ldots, x_N-x_o]_{3 \times N}$·µ is updated by $$\Delta\mu = \|vector(C)\|/\|vector(B)\| \quad (16)$$

$$\mu_{new} = \mu_{old} \Delta\mu \quad (17)$$

Finally, points $p_i$ are updated according to Equation (10).

Proof of Convergence

We first provide the mathematical proof of the convergence of R1PPnP when not using $1/\lambda_i$ as weights in the objective function Equation (12). k denotes the number of iterations. $q_i^{(k+1)}$ is obtained by vertically projecting $p_i^{(k)}$ to the line of sight i, and $q_i^{(k+1)}$ and $q_i^{(k)}$ are on the line of sight i. Hence, the three points, $p_i^{(k)}, q_i^{(k)}$, and $q_i^{(k+1)}$ comprise a right-angled triangle. Therefore, for each index i, i≠o, $$\|p_i^{(k)} - q_i^{(k+1)}\|^2 = \|p_i^{(k)} - q_i^{(k)}\|^2 - \|q_i^{(k+1)} - q_i^{(k)}\|^2 \quad (18)$$

In the $p^{(k+1)}$ updating stage, the updated R and µ make the objective function Equation (12) smaller. Hence, $$\Sigma_{i=1}^{N} \|p_i^{(k+1)} - q_i^{(k+1)}\|^2 \leq \Sigma_{i=1}^{N} \|p_i^{(k)} - q_i^{(k+1)}\|^2 \quad (19)$$

According to Equation (18), Equation (19), and the objective function Equation (12), $$f(p_i^{(k+1)}, q_i^{(k+1)}) \leq f(p_i^{(k)}, q_i^{(k)}) - \Sigma_{i=1}^{N} \|q_i^{(k+1)} - q_i^{(k)}\|^2 \quad (20)$$

Hence, the objective function will strictly decrease until $q_i^{(k+1)} = q_i^{(k)}$ when not using $1/\lambda_i$ as weights. However, when $1/\lambda_i$ is applied in the objective function, the above convergence proof is not rigorous in mathematics because $\lambda_i^{(k+1)} \neq \lambda_i^{(k)}$. As the iteration process, the changes of $\lambda_i$ become small, which makes the formula Equation (20) hold. In addition, our experimental results in this disclosure also support the assumption that our algorithm is convergent.

Local Minima Avoidance

We have concluded that the iterative process of R1PPnP is convergent. However, we still need to address situations that R1PPnP may get stuck in local minima. To demonstrate the iterative process more intuitively, we introduce a 1D camera working in the 2D space, as shown in FIG. 4. In this demonstration, an object with four points $P_i$, i=1, . . . , 4 are projected to the camera image plane and their image points $x_i$ are obtained. $P_1$ is selected as the control point, which means o=1. Different initial values may result in different convergence results.

FIG. 4 shows iterative process with 2D space and 1D camera imaging plane. $P_1$, $P_2$, $P_3$ and $P_4$ are the object points; $P_1$ is selected as the control point (o=1). FIG. 4A shows that the iterative process $p^{(k)} \to q^{(k+1)} \to p^{(k+1)} \to \ldots$ makes the estimation pose approach the correct solution. FIG. 4B shows that the rotation related to $P^{(k+1)}$ is worse than that related to $p^{(k)}$, which means the process is approaching a local minima, which is a mirror-image form of the true object shape.

FIG. 4A demonstrates a process that is approaching the correct global optimal results. Beginning with points $p^{(k)}$, the algorithm projects $p^{(k)}$ to their related lines of sight and obtains points $q^{(k+1)}$. Then, according to $q^{(k+1)}$, the algorithm updates the rotation R and scale factor µ to generate points $p^{(k+1)}$. In this process, the rotation and scale factor related to $p^{(k+1)}$ are closer to the truth compared to that related to $p^{(k)}$, and finally the algorithm will reach the correct solution.

However, as the progress shown in FIG. 4B indicates, $p^{(k+1)}$ has a larger pose error than $p^{(k)}$, and the algorithm will finally get stuck in local minima. The reconstructed points $p^{(k)}$ or $p^{(k+1)}$ come in mirror-image forms of the real object points P. Without loss of generality, in either 2D or 3D space, a mirror-image form suggests that the left-right-handed shape of the point cloud has been changed, which should not happen in reality. The reason the core algorithm of R1PPnP may generate points with different left-right-handed shape is that its rotation estimation equation (15) does not constrict det(R)=1.

In practice we found it not appropriate to constrain det(R)=1 from the beginning of the algorithm. Instead, we allow the iteration process to approach the mirror-image form. This is because we found that, with the constrain det(R)=1 from the beginning, the algorithm has many types of local minima and they are unpredictable. However, without this constrain, the convergence direction of the core algorithm becomes predictable, with only two types of convergence. The algorithm may reach the global optimal result directly or the approximate mirror-image form. For the latter case, the estimated det(R)=−1.

Hence, according to the above analysis, we propose the local minima avoidance mechanism. The algorithm begins with a random initial value and control point. When the algorithm converges to a result with det(R)=−1, we perform a mirror flip by $$\lambda_{i,new}=1/\lambda_{i,old}, i=1,\ldots,N \text{ and } i \neq o. \quad (21)$$

Control Point o Selection

Figure 5:
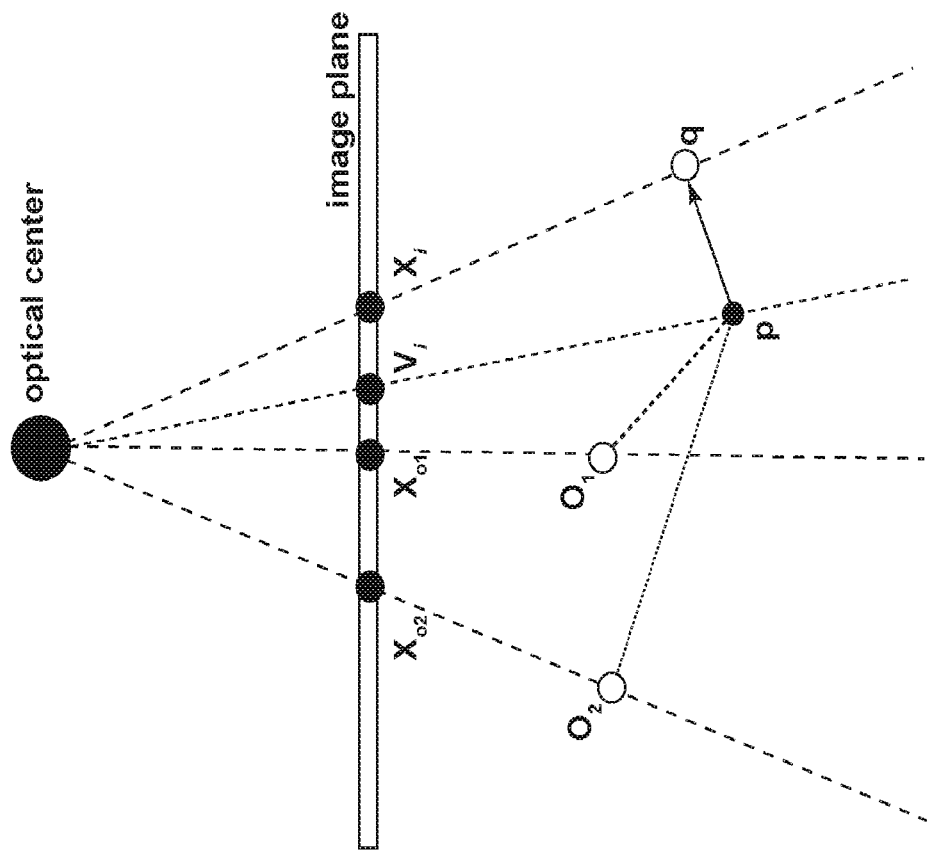
FIG. 5 is an illustration of an example to show the behavior of how the selection of control point o is related to the convergence rate with 2D space and 1D camera imaging plane.

In R1PPnP, the selection of control point o is related to the convergence rate. FIG. 5 illustrates an example to illustrate the behavior of how the selection of control point o is related to the convergence rate with 2D space and 1D camera imaging plane. According to the R and µ updating methods in Equations (15) and (16). $\langle p-o_1, q-o_1 \rangle > \langle p-o_2, q-o_2 \rangle$ and $\|x_i-x_{o1}\|/\|v_i-x_{o1}\| > \|x_i-x_{o2}\|/\|v_i-x_{o2}\|$ suggest that the iteration process is more likely to have larger R and µ updating rate when o is closer to p.

To select different points as the control point o may result in different convergence rates. Without taking into account noise, the correct value of rotation R should be the same for any control point o in a PnP task. Hence, larger rotation updating steps in the iteration process suggest that less number of iterations are required to converge to the correct value when starting from the same initial value. In R1PPnP, R is updated according to the differences between points $p_i$ and $q_i$, i=1, . . . , N, i≠o. When point o is close to $p_i$, the rotation updating steps are more likely to be large, as shown in FIG. 5. The updating rates of µ also follow this analysis. Therefore, we are prone to select the control point o from the center of the point cloud, which has better odds of having smaller distances to the rest of the point cloud to achieve faster convergence rate.

Outliers Handling Mechanism

The robust and fast capability of handling outliers is the main contribution of the proposed R1PPnP algorithm. Our outliers handling mechanism combines a soft weight assignment method and the 1-point RANSAC scheme.

Soft Re-weighting

R1PPnP mainly consists of $q_i$ and $p_i$ estimation stages. As described in the "Model" section, in the $q_i$ stage, calculations related to each point are independent from the others. Hence, outliers do not affect inliers in the $q_i$ stage. However, in the $p_i$ stage, outliers perturbs the camera pose estimation results. To reduce the impact of outliers, the basic idea of our soft re-weighting method is to assign each 3D-2D correspondence a weight factor, and to make weight factors related to outliers small when estimating the camera pose in the $p_i$ stage.

One possible method to assign weights is based on least median of squares, however this method cannot handle more than 50% of outliers. We designed a soft weight assignment method embedded in the iteration process. To distinguish inliers and outliers, the weights of 3D-2D correspondences are determined by $$w_i = \begin{cases} 1.0 & \text{if } e_i \leq H \\ H/e_i & \text{if } e_i > H \end{cases} \quad (22)$$

where $e_i$ suggests the reprojection error of point i with the current R and µ during iteration, H is the inliers threshold that points with final reprojection errors smaller than H are considered as inliers. The reweighting rule Equation (22) suggests that a point with a large reprojection error will have a small weight during the estimation of camera pose, which is designed under a reasonable assumption that outliers have much larger reprojection errors than inliers. Although inliers may also have larger reprojection errors than H during the iteration process, it is acceptable to assign weights that are smaller than 1 to inliers as long as outliers have much smaller weights. Hence, we simply use H as the benchmark to assign weights.

According to R estimation given by Equation (15), we multiply the weight factors with each item of matrices A and S, $$A_i = w_i A_i, S_i = w_i S_i \quad (23)$$

Similarity, to update µ using Equation (16), $$B_i = w_i B_i, C_i = w_i C_i \quad (24)$$

Since inliers have much larger weights, R and µ are mainly estimated with inliers.

1-Point RANSAC Scheme

The core algorithm of R1PPnP is based on a randomly selected control point o. In outlier-free situations, our algorithm works with any control point. However, in situations with outliers, the control point o should be an inlier to make the algorithm work. Hence, we employ the 1-point RANSAC scheme to try different 3D-2D correspondences as the control point until the algorithm finds the correct solution. The 1-point RANSAC scheme combines the core algorithm naturally because the core algorithm can perform the computation with any control point o ∈ [1, N]. We assume that 2D-3D correspondences have the same the possibility to be an inlier, without loss of generality, we select the control point o from the center of all image points to the outside. This is because we found that R1PPnP needs less iterations to converge when o is closer to the center, the details of which has been discussed in the "Control Point o Selection" subsection of the "Core Algorithm Design" section.

Flow Chart

FIG. 6 shows pseudocode that generally illustrates a process 200 that uses the R1PPnP algorithm to estimate a pose. First, the process 200 detects as many inliers as possible inside the RANSAC framework, then based on the detected inliers, the process 200 executes the R1PPnP algorithm without re-weighting mechanism to get more accurate results.

Figure 7:
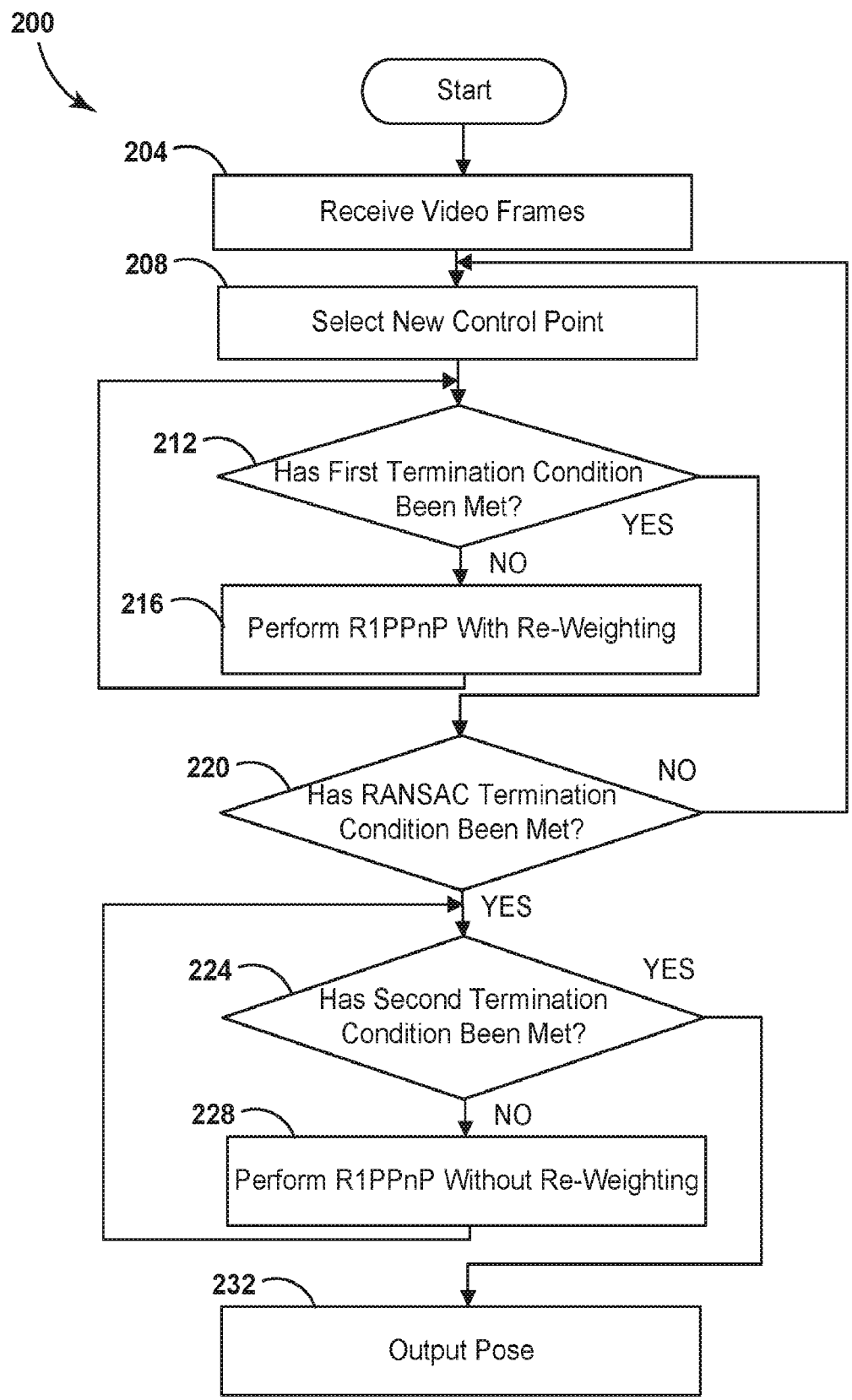
FIG. 7 shows a flowchart including the process that uses the R1PPnP algorithm to estimate a pose.

FIG. 7 shows a flowchart including the process 200. The process 200 can start with a predetermined pose, and is update the pose using R1PPnP techniques. At 204, the process 200 can receive video frames including a right video frame and a left video frame. The process 200 can then proceed to 208. At 208, the process 200 can select a new control point o. The process 200 can then proceed to 212. At 212, the process 200 can determine if a first termination condition has been meet. The first termination condition can be Equation (26). The process 200 can proceed to 216 if the first termination condition has not been met (i.e., the "NO" at 212). The process 200 can proceed to 220 if the first termination condition has been met (i.e., the "YES" at 212).

At 216, the process 200 can execute the R1PPnP algorithm with reweighting based on the Equation (9) described above. The process 200 can then proceed to 212. At 220, process 200 can determine if the RANSAC termination condition (26) has been met. If the RANSAC termination condition (26) has been met, (i.e., the "YES" at 220), the process 200 can proceed to 224. If the RANSAC termination condition (26) has not been met, (i.e., the "NO" at 220), the process 200 can proceed to 208.

At 224, the process 200 can determine if a second termination condition has been met. The second termination condition can be Equation (27). The process 200 can proceed to 228 if the first termination condition has not been met (i.e., the "NO" at 224). The process 200 can proceed to 232 if the first termination condition has been met (i.e., the "YES" at 212).

At 228, the process 200 can perform execute the R1PPnP algorithm without reweighting. The process 200 can then proceed to 224. At 232, the process 200 can output an estimated pose.

Appropriate termination conditions seek balance between speed and precision for RANSAC-based or iterative algorithms. As shown in FIG. 6, two types of termination conditions need to be specified for R1PPnP.

RANSAC Termination Condition

The standard RANSAC termination condition was employed for R1PPnP, that is $$\text{trials} \geq \log(1-p)/\log(1-p_{inliers}{}^s), \quad (25)$$

where p is the certainty and we use p=0.99 for all RANSAC-based methods in this disclosure, trials is the number of RANSAC trials, $p_{inliers}$=(maximum number of detected inliers)/(number of all points), s is the number of control points needed in each RANSAC trial. s=1 for R1PPnP, and s=3,4 for RANSAC+P3P and P4P respectively.

During the RANSAC process, the camera pose estimated by conventional RANSAC+P3P or P4P methods is based on very small number of points. Because of image noise, the estimated pose varies with different inliers as the control points. This is especially serious when the image noise is large. To improve accuracy, the termination condition Equation (25) suggests that the standard RANSAC scheme may continue looking for better results after finding a large percentage of inliers. In contrast, R1PPnP takes into account all points when estimating the pose, which makes it insensitive to the selected control point o. Therefore it is a reasonable assumption that when $p_{inliers}$ is large enough (we used the threshold of 60%), no improvement can be found and the RANSAC process of R1PPnP could be terminated. Accuracy evaluation results in this disclosure have testified the rationality of this assumption.

Termination Conditions for R1PPnP Iterations

As shown in FIG. 6, we first detect as many inliers as possible and the related termination condition A is satisfied when the detected number of inliers becomes stable, that is, $$N_{inlier}{}^{(k)} - N_{inlier}{}^{(k-20)} \leq 0 \text{ and } k > 20, \quad (26)$$

where k is the index of iterations, $N_{inlier}$ is the number of detected inliers. According to our experience, in most cases no more inliers would be detected if $N_{inlier}$ has not increased in 20 iterations. It is more robust and efficient to stop the process when no more inliers can be detected.

A good termination condition A should be able to stop the iteration process as early as possible when point o is an outlier, and do not interrupt when point o is an inlier. We proposed the termination condition A with a window size=20 iterations to seek balance between speed and robustness. This termination condition is not based on the comparison of parameters of adjacent iterations because in R1PPnP, the dynamically updated weights $w_i$ may make the convergence process complex, especially when point o is an outlier. With an outlier as the control point, $\|R^{(k)} - R^{(k-1)}\|$ may take many iterations to converge to zero, which is slow. With the change of detected number of inliers in a larger window size, the termination decision can be more robust and efficient.

The refinement stage makes pose estimation results more accurate based on the detected inliers. Without the reweighting mechanism, the convergence process is much simple. Hence the termination condition B is satisfied when the estimated rotation becomes stable, that is, $$\|R^{(k)} - R^{(k-1)}\| < 1e-5. \quad (27)$$

Experiments

The performance of the proposed R1PPnP algorithm was evaluated by comparing against the state-of-the-art PnP methods. The source code was implemented in MATLAB scripts and executed on a computer with an Intel Core i72.60 GHz CPU. We used both synthetic and real-world data to conduct evaluation experiments. The initial values for R1PPnP are R=diag{1,1,1} and μ=1e−4. RANSAC+P3P or P4P methods also used the standard termination condition Equation (25).

Synthetic Experiments

Synthetic experiments in this disclosure shared the following parameters. The camera focal length is 1,000 pixels with a resolution of 640×480. Two types of synthetic data were generated. (1) Ordinary three-dimensional (3D) case: object points were randomly and uniformly distributed in a cube region [−2,2]×[−2,2]×[4,8]. (2) Quasi-singular case: The distribution cube is [1,2]×[1,2]×[4,8]. For each experiment result, we report the mean values of 100 trials.

For accuracy evaluation, the rotation error is measured in degrees between the truth rotation $R_{true}$ and the estimated R as $e_{rot}(\deg) = |[\acos(r_{k,true}{}^T \cdot r_k)_{k=1,2,3}]^T| \times 180/\pi$, where $r_{k,true}$ and $r_k$ are the k th column of $R_{true}$ and R respectively. The translation error is $e_{trans}(\%) = \|t_{true} - t\|/\|t\| \times 100\%$.

Outlier-Free Synthetic Situations

Figure 8B:
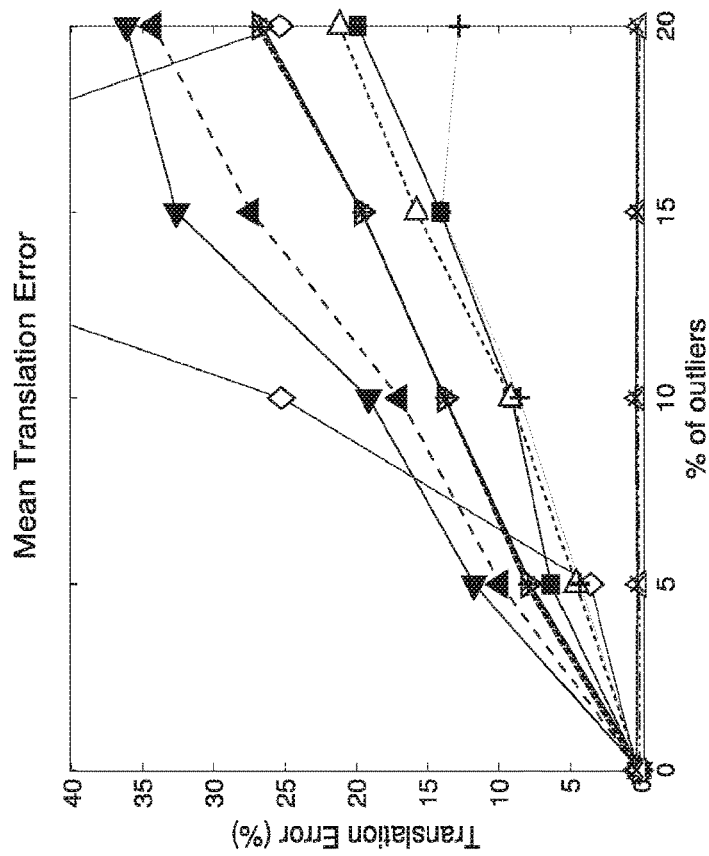
FIG. 8B is a graph of translation error as a percent vs percentage of outliers for the same PnP methods.
Figure 8A:
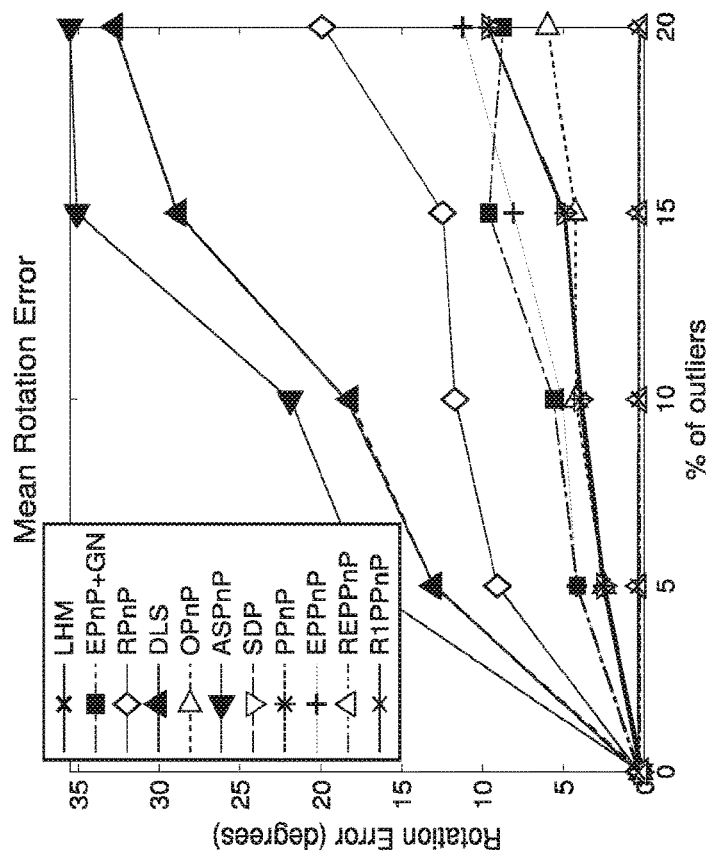
FIG. 8A is a graph of rotation error in degrees vs. percentage of outliers for various perspective-n-point (PnP) methods.

Most PnP algorithms do not have the ability to handle outliers, and even a small percentage of outliers will significantly reduce the accuracy, as shown in FIG. 8. FIG. 8A shows a graph of rotation error in degrees vs. percentage of outliers for various PnP methods, and FIG. 8B shows a graph of translation error as a percent vs percentage of outliers for the same PnP methods. Except for REPPnP and R1PPnP, most PnP methods cannot handle outliers. Thus, although outlier-free situations are not the main concern of R1PPnP, we first conducted comparison experiments between the proposed R1PPnP and other PnP algorithms in outlier-free situations. The reason for this comparison is that RANSAC+P3P or P4P methods usually need other PnP methods as the final refinement step. Hence the accuracy and speed in outlier-free situations are also related to the performance in situations with outliers.

Here we only performed the core algorithm of R1PPnP without outliers handling mechanism. The termination condition for R1PPnP iterations was as Equation (27). In this experiment, we compared our proposed R1PPnP with the following PnP methods: LHM, EPnP, RPnP, DLS, OPnP, ASPnP, SDP, PPnP, EPPnP and REPPnP.

In our accuracy evaluation experiments, the number of points was 100 and we added different levels of Gaussian image noises from 0 to 10 pixels.

Figure 9B:
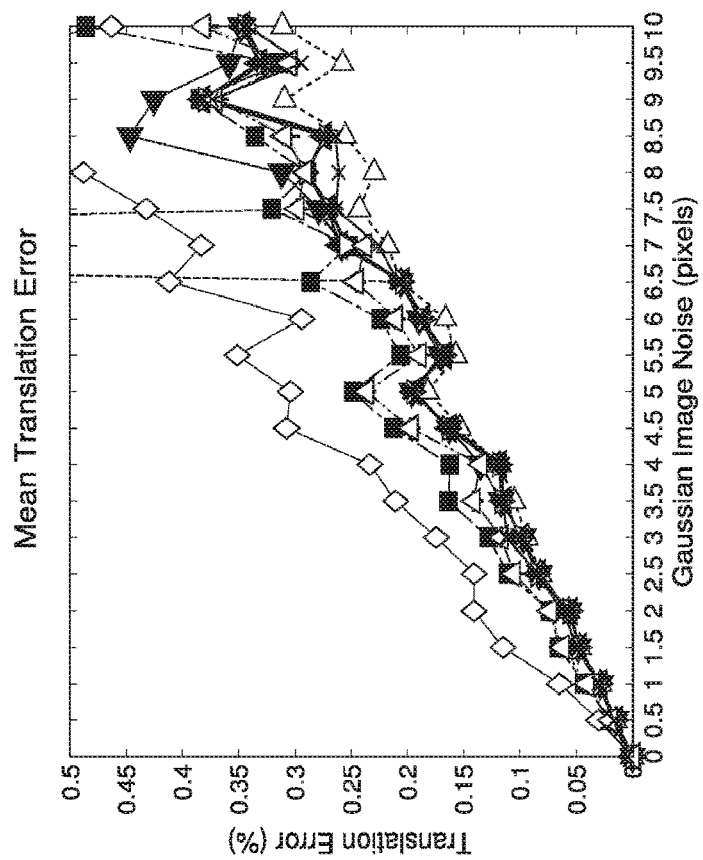
FIG. 9B is a graph of mean translation error as a percent vs. Gaussian image noise in pixels for the PnP methods used in FIG. 9A on outlier-free synthetic data for ordinary 3D cases.
Figure 9A:
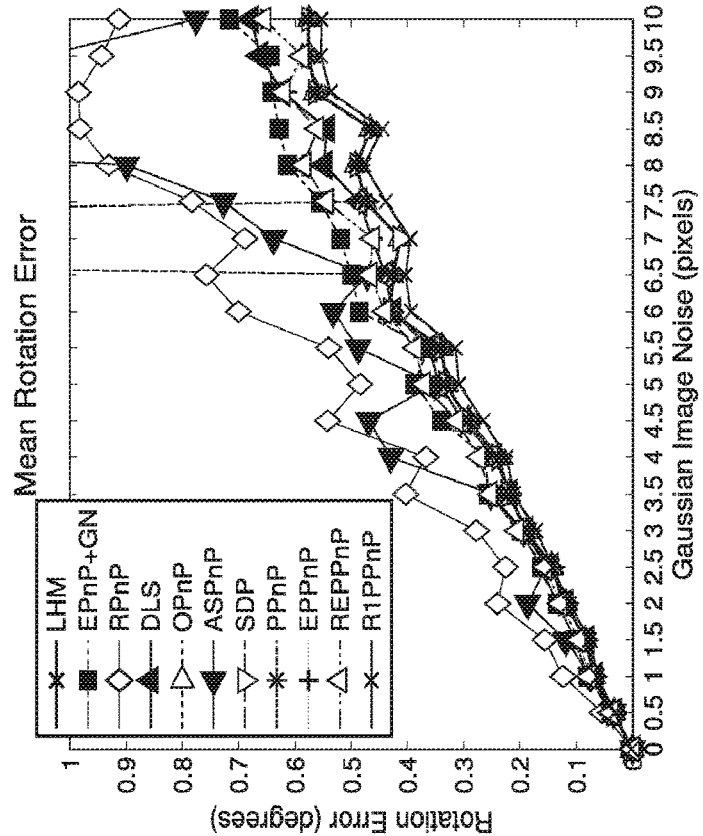
FIG. 9A is a graph of mean rotation error in degrees vs. Gaussian image noise in pixels for various PnP methods used with outlier-free synthetic data for ordinary three-dimensional (3D) cases.

FIG. 9A shows a graph of mean rotation error in degrees vs. Gaussian image noise in pixels for various PnP methods used with outlier-free synthetic data for ordinary 3D cases. FIG. 9B shows a graph of mean translation error as a percent vs. Gaussian image noise in pixels for the PnP methods used in FIG. 9A on outlier-free synthetic data for ordinary 3D cases.

FIG. 10A shows a graph of mean rotation error in degrees vs. Gaussian image noise in pixels for various PnP methods used with outlier-free synthetic data for quasi-singular cases. FIG. 10B shows a graph of mean translation error as a percent vs. Gaussian image noise in pixels for the PnP methods used in FIG. 9A on outlier-free synthetic data for quasi-singular cases.

As shown in FIGS. 9A-B and 10A-B, for both ordinary 3D and quasi-singular cases, R1PPnP gave the most accurate rotation estimation results together with OPnP and SDP. For ordinary 3D cases, R1PPnP was among the most accurate methods to estimate translation.

To evaluate runtime, Gaussian image noise with a standard deviation of σ=5 pixels was added and the number of points increased from 100 to 1000.

Figure 11A:
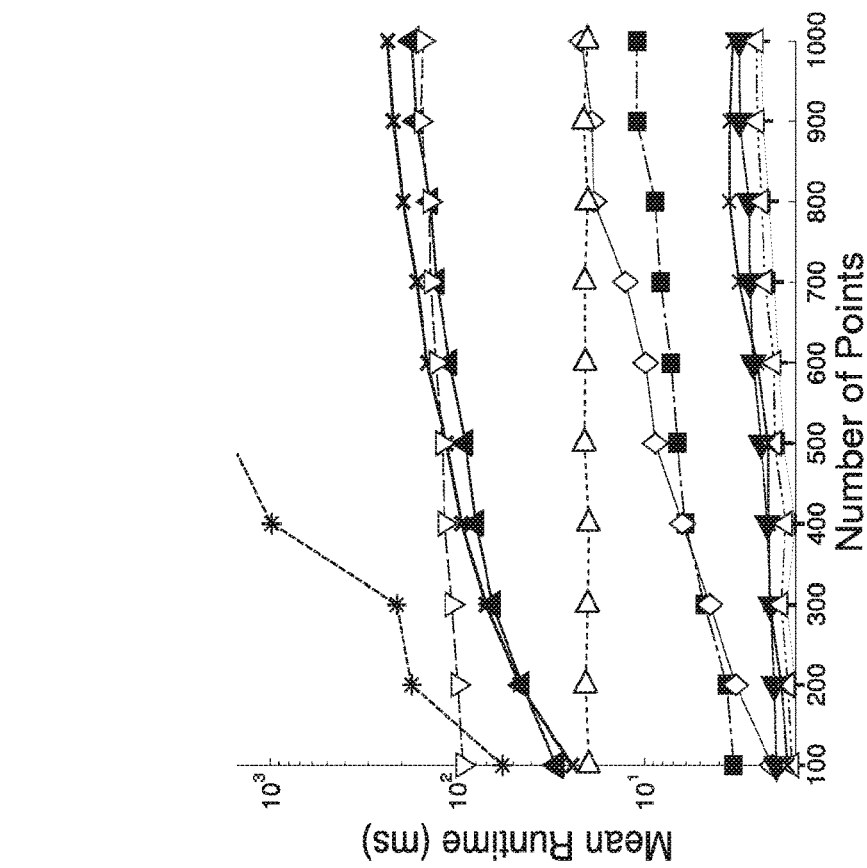
FIG. 11A is a graph of mean runtime vs. number of points for various PnP methods with outlier-free synthetic data for ordinary 3D cases. Standard deviation of image noise is $\sigma=5$ pixels.
Figure 11B:
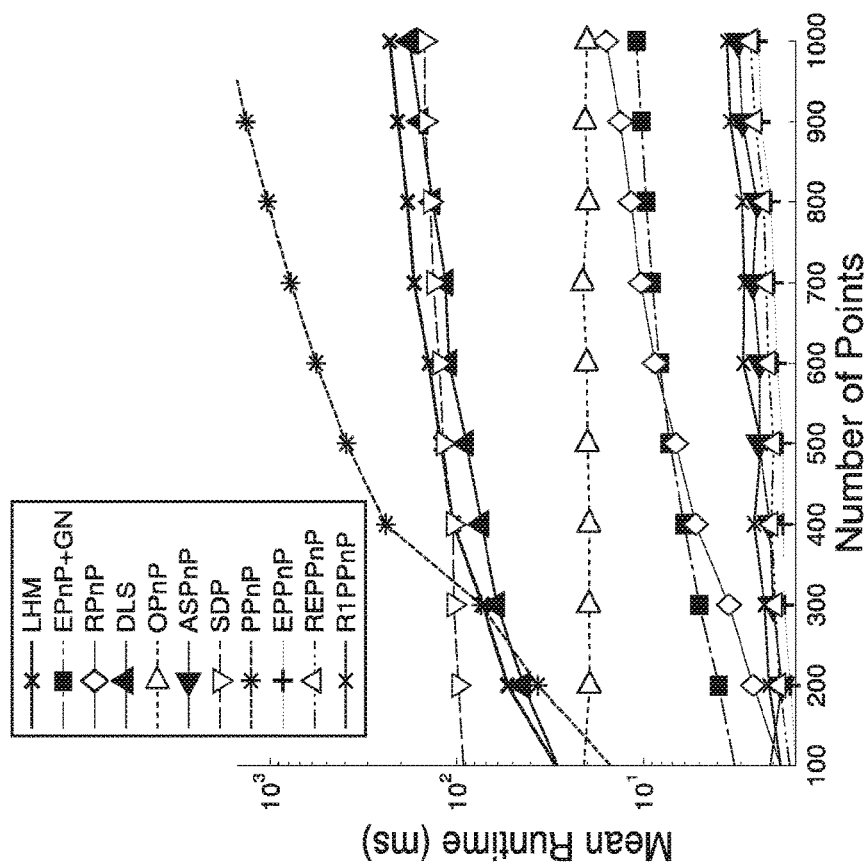
FIG. 11B is a graph of mean runtime vs. number of points for various PnP methods with outlier-free synthetic data for quasi-singular cases. Standard deviation of image noise is $\sigma=5$ pixels.

FIG. 11A shows a graph of mean runtime vs. number of points for various PnP methods with outlier-free synthetic data for ordinary 3D cases. Standard deviation of image noise is σ=5 pixels. FIG. 11B shows a graph of mean runtime vs. number of points for various PnP methods with outlier-free synthetic data for quasi-singular cases. Standard deviation of image noise is σ=5 pixels.

As shown in FIGS. 11A-B, the R1PPnP method showed superior computational speed. The runtime of R1PPnP did not grow significantly with respect to the number of points.

Generally speaking, in outlier-free situations, R1PPnP was among the state-of-the-art methods in terms of both accuracy and computational speed.

Synthetic Situations with Outliers

The main advantage of R1PPnP is that it is capable of handling a large percentage of outliers with a much faster speed than conventional methods. For demonstrating this, we introduced the following RANSAC-based P n P methods for comparison: (RANSAC+P3P); (RANSAC+RP4P+ RPnP); (RANSAC+P3P+ASPnP); and (RANSAC+P3P+ OPnP). According to evaluations in outlier-free situations, OPnP is the most accurate PnP method and ASPnP and RPnP are fast. We selected these methods as the final refinement step to fully demonstrate the performance of RANSAC+ refinement-like methods. Another important method is REPPnP, which is the state-of-the-art PnP algorithm that addresses outliers.

The experiments were conducted as follows. $N_{inlier}$=100 correct matches (inliers) between 3D object points and 2D image points were generated. $N_{outlier}$ mismatches (outliers) were generated by randomly corresponding 3D and 2D points. The true percentage of outliers is $p_{outlier}=N_{outlier}/(N_{inlier}+N_{outlier})$. Gaussian image noise with a standard deviation of σ=5 pixels was added. For R1PPnP and other RANSAC-based methods, the reprojection error threshold to distinguish inliers and outliers was H=10 pixels.

Figure 12B:
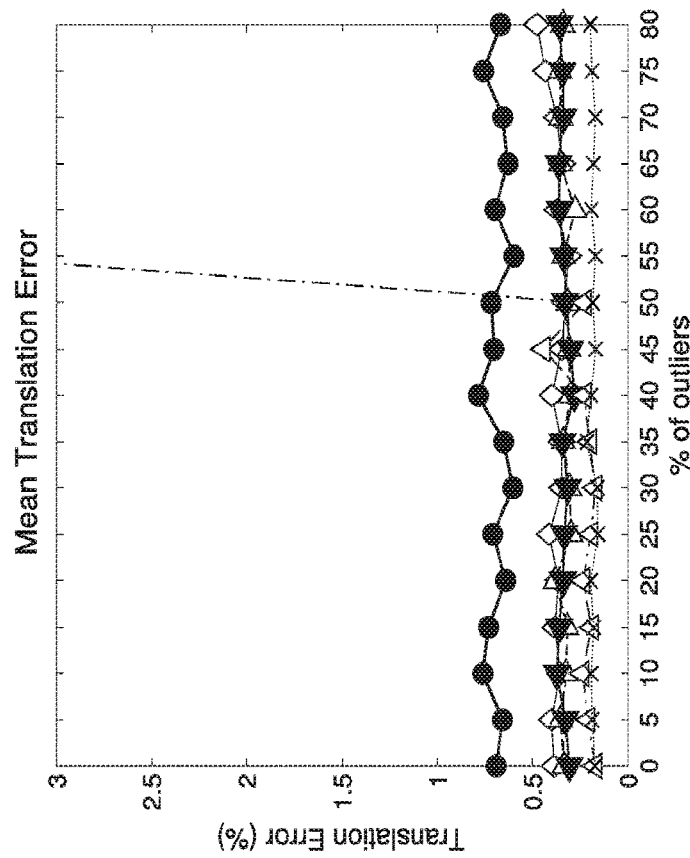
FIG. 12B is a graph of mean translation error as a percent vs. percentage of outliers for synthetic data with outliers for ordinary 3D cases.
Figure 12A:
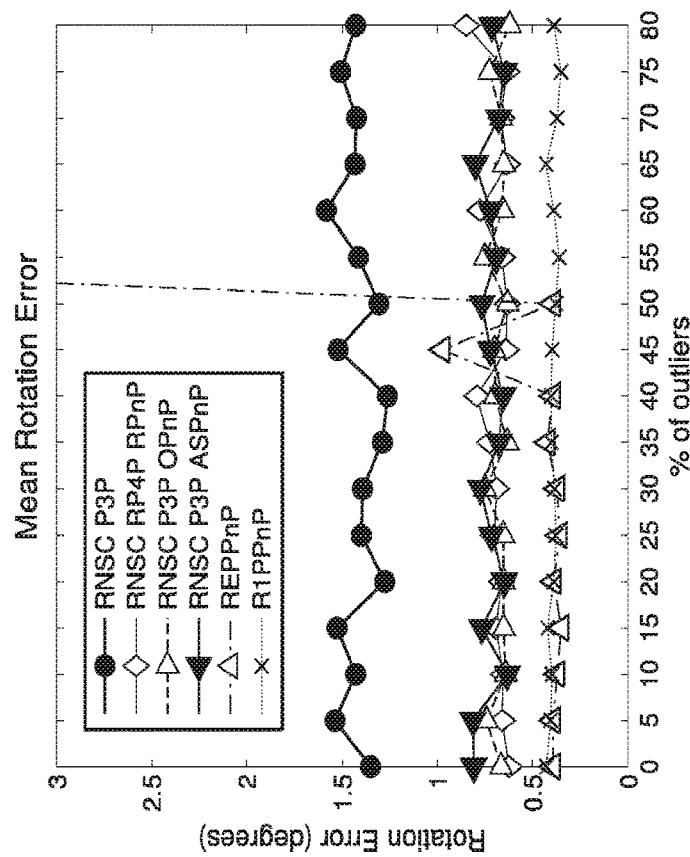
FIG. 12A is a graph of mean rotation error in degrees vs. percentage of outliers for synthetic data with outliers for ordinary 3D cases.

FIG. 12A is a graph of mean rotation error in degrees vs. percentage of outliers for synthetic data with outliers for ordinary 3D cases. FIG. 12B is a graph of mean translation error as a percent vs. percentage of outliers for synthetic data with outliers for ordinary 3D cases.

Figure 12D:
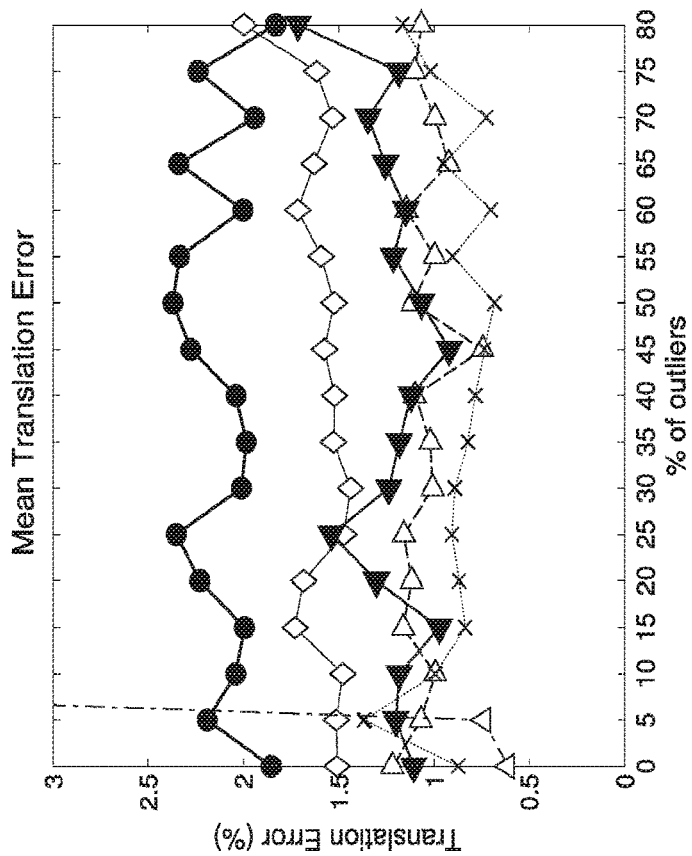
FIG. 12D is a graph of mean translation error as a percent vs. percentage of outliers for synthetic data with outliers for quasi-singular cases.
Figure 12C:
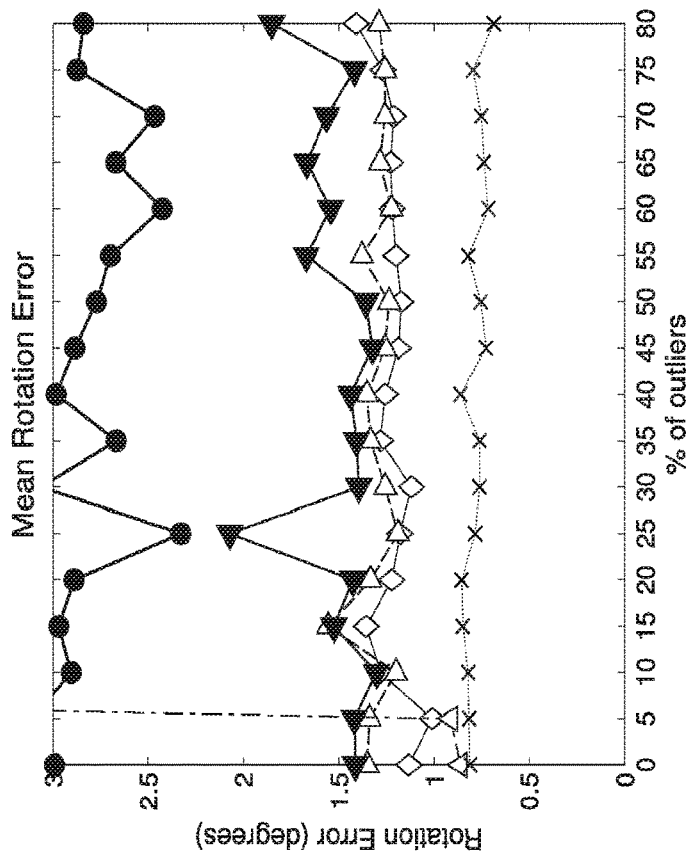
FIG. 12C is a graph of mean rotation error in degrees vs. percentage of outliers for synthetic data with outliers for quasi-singular cases.

FIG. 12C is a graph of mean rotation error in degrees vs. percentage of outliers for synthetic data with outliers for quasi-singular cases. FIG. 12D is a graph of mean translation error as a percent vs. percentage of outliers for synthetic data with outliers for quasi-singular cases.

As shown in FIGS. 12A-D, REPPnP began to fail when the percentage of outliers was larger than 50% with ordinary 3D cases, and only 5% with quasi-singular cases. R1PPnP was capable of handling situations with a large percentage of outliers. R1PPnP was more accurate than RANSAC-based methods for both rotation and translation estimation.

Figure 13B:
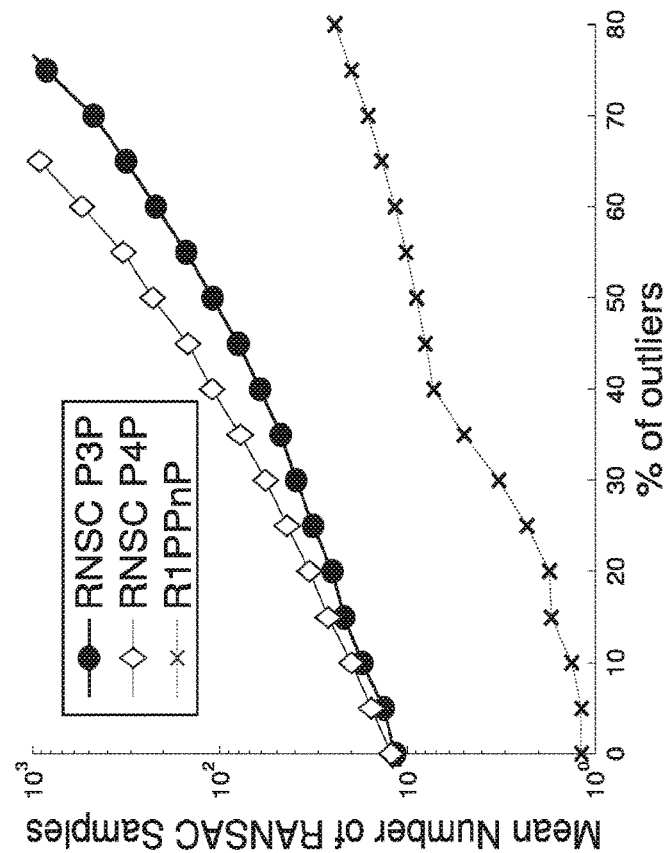
FIG. 13B is a graph of mean number of random sample consensus (RANSAC) samples vs percentage of outliers for RANSAC-based methods using ordinary 3D cases synthetic data.
Figure 13A:
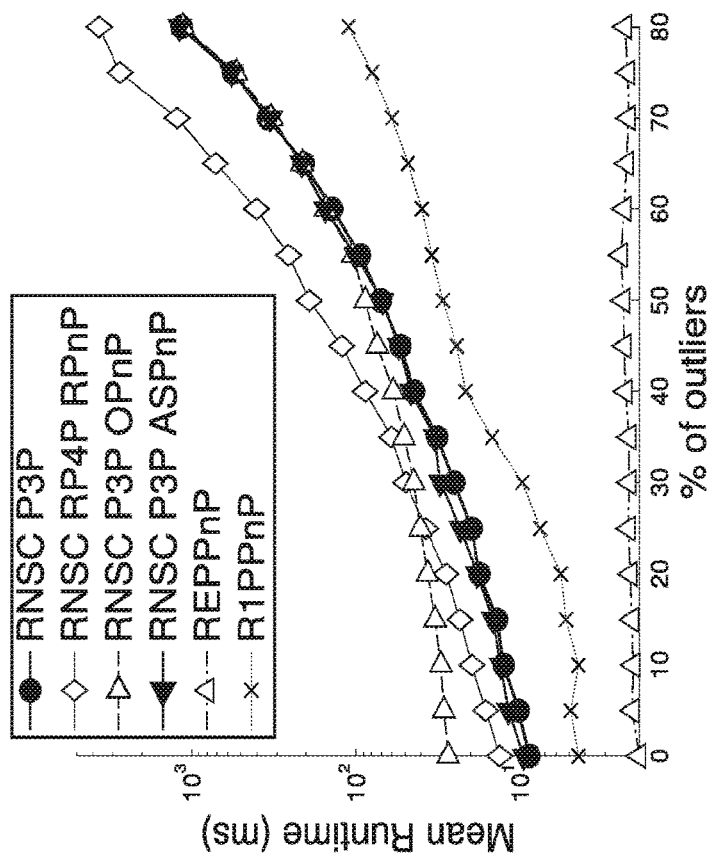
FIG. 13A is a graph of mean runtime in milliseconds vs percentage of outliers for various methods using ordinary 3D cases synthetic data.

FIG. 13A shows a graph of mean runtime in milliseconds vs percentage of outliers for various methods using ordinary 3D cases synthetic data. FIG. 13B shows a graph of mean number of RANSAC samples vs percentage of outliers for RANSAC-based methods using ordinary 3D cases synthetic data. Results with quasi-singular cases are similar to the results with ordinary 3D cases. RANSAC+P3P or P4P needs more than 10 RANSAC trails when $p_{outliers}$=0 because the large image noise (σ=5 pixels) usually makes P3P or P4P methods unable to find the correct pose with 3 or 4 inliers to satisfy the termination condition Equation (25). In contrast, the required number of RANSAC trials of R1PPnP is not sensitive to image noise because all points are taken into account. As shown in FIGS. 13A-B, compared to other RANSAC-based methods, R1PPnP was much faster, especially when the percentage of outliers was large.

Real-World Image Data

Our real-world experiments were conducted on the Technical University of Denmark (DTU) robot image data at http://roboimagedata.imm.dtu.dk/, which provides images and the related 3D point cloud obtained by structured light scan. The true values of rotations and translations are known. Images have a resolution of 800×600. Datasets numbered 1 to 30 were used. In each dataset, images were captured under 19 different illumination situations and from 119 camera positions. We selected 10 out of 19 illumination situations. Hence, a total of 30×10×119=35700 images were included in this evaluation. Following the instruction, for each dataset and illumination situation, we used the image numbered 25 as the reference image and performed SURF matching between the reference image and other images. The inliers threshold was H=5 pixels for all methods. With each image, we ran all algorithms 5 times and used the average value for the subsequent statistics.

The total number of correspondences and the percentage of outliers varied with objects, illumination situations and camera poses. Although clear comparisons require that only one factor is different, this kind of variable-controlling is difficult for PnP evaluation on real-world data because SURF matching results are unpredictable. In experiments we found that the performance of PnP algorithms were mainly affected by the percentage of outliers, rather than the total number of correspondences. Therefore in this section, we report the evaluation results by comparing the statistical results of PnP methods at each percentage of outliers range. Because the true number of inliers was unknown, for each image, algorithms detected inliers and we considered the maximum number of inliers as the ground truth.

Figure 14A:
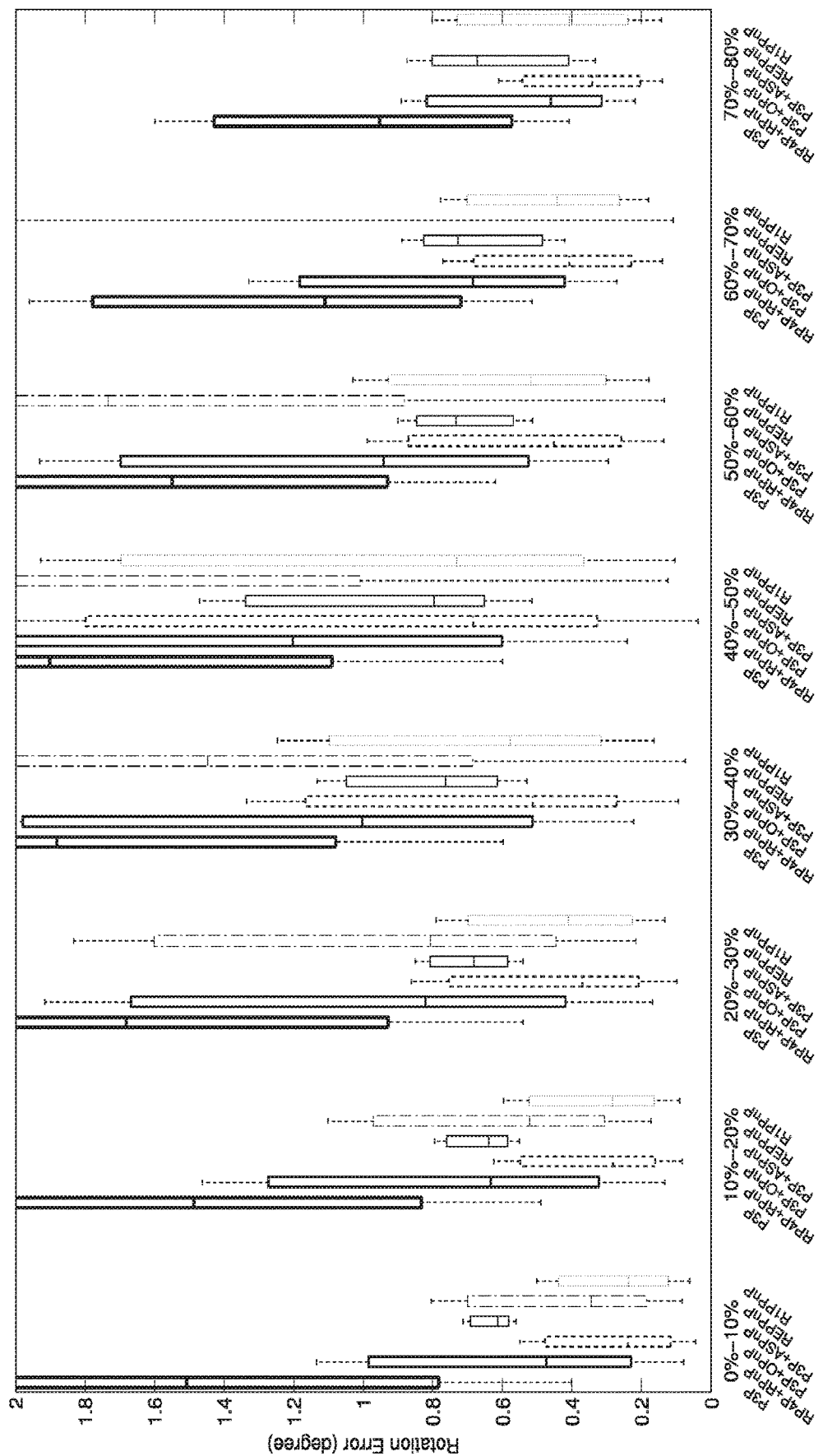
FIG. 14A is a graph of rotation error in degrees vs. percentage of outliers for various methods with real world data.
Figure 14B:
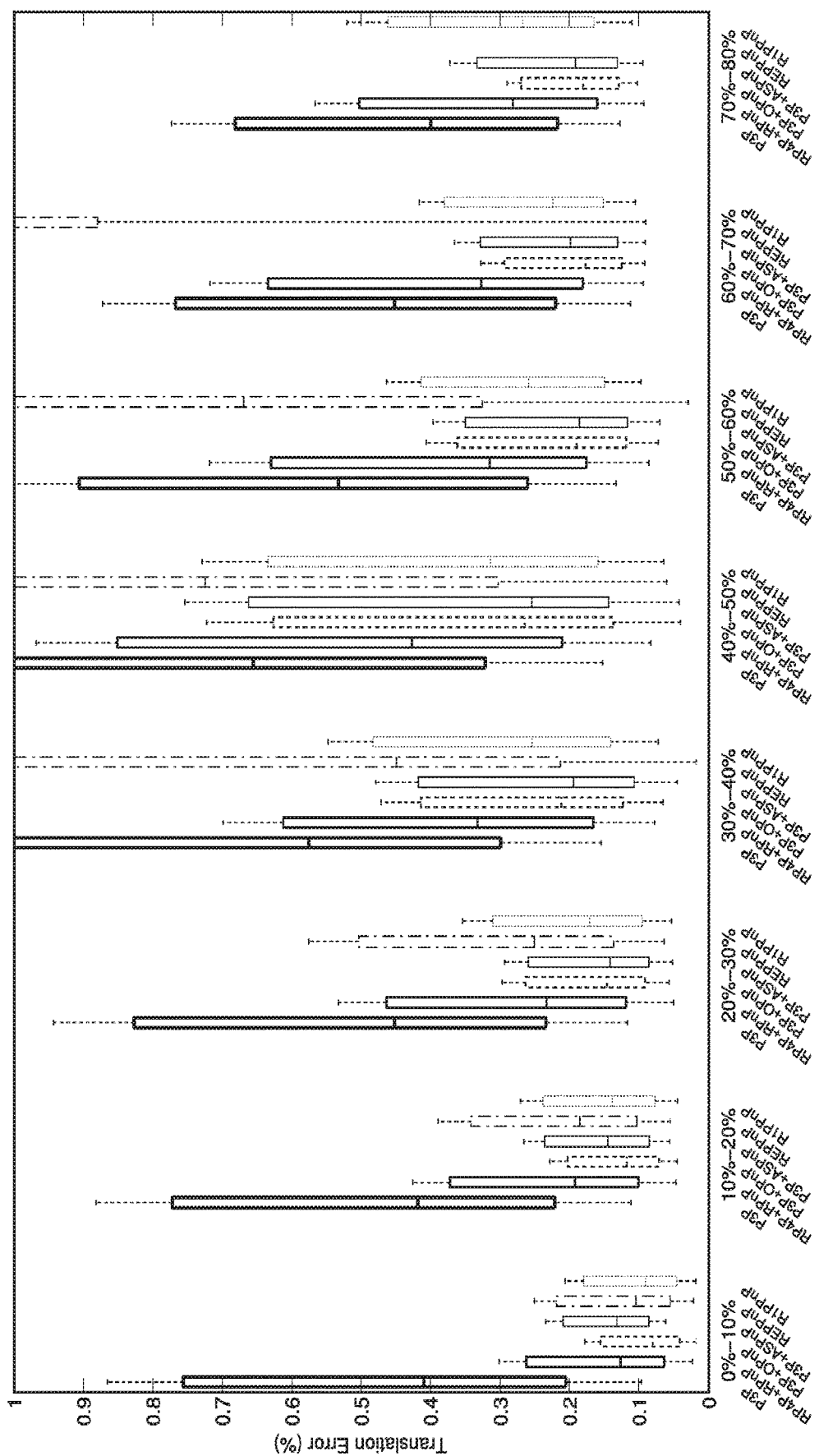
FIG. 14B is a graph of translation error as a percent vs. percentage of outliers for various methods with real world data.

FIG. 14A shows a graph of rotation error in degrees vs. percentage of outliers for various methods with real world data. FIG. 14B shows a graph of translation error as a percent vs. percentage of outliers for various methods with real world data.

Figure 14C:
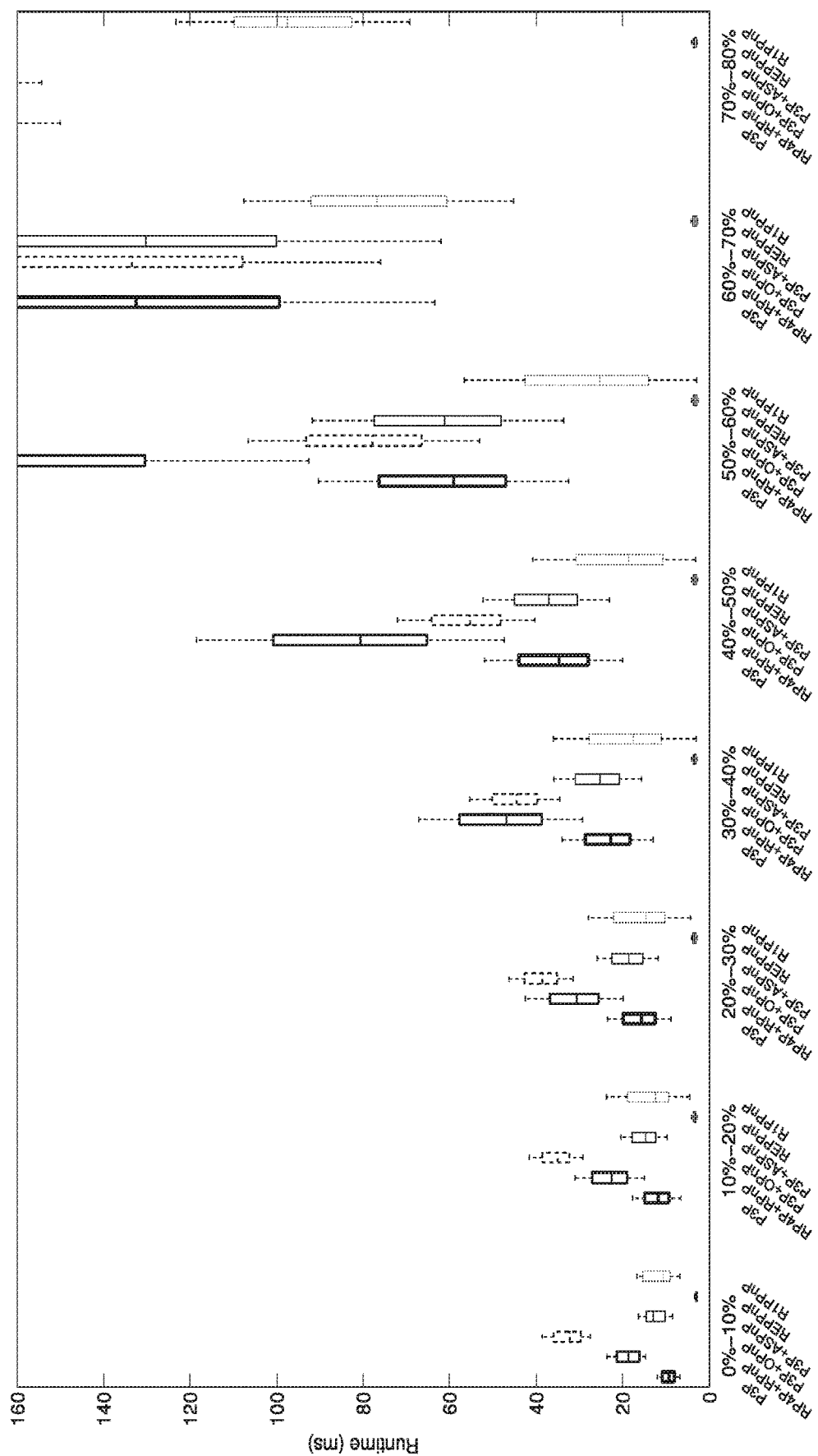
FIG. 14C is a graph of runtime of the various methods in FIG. 14A.
Figure 14D:
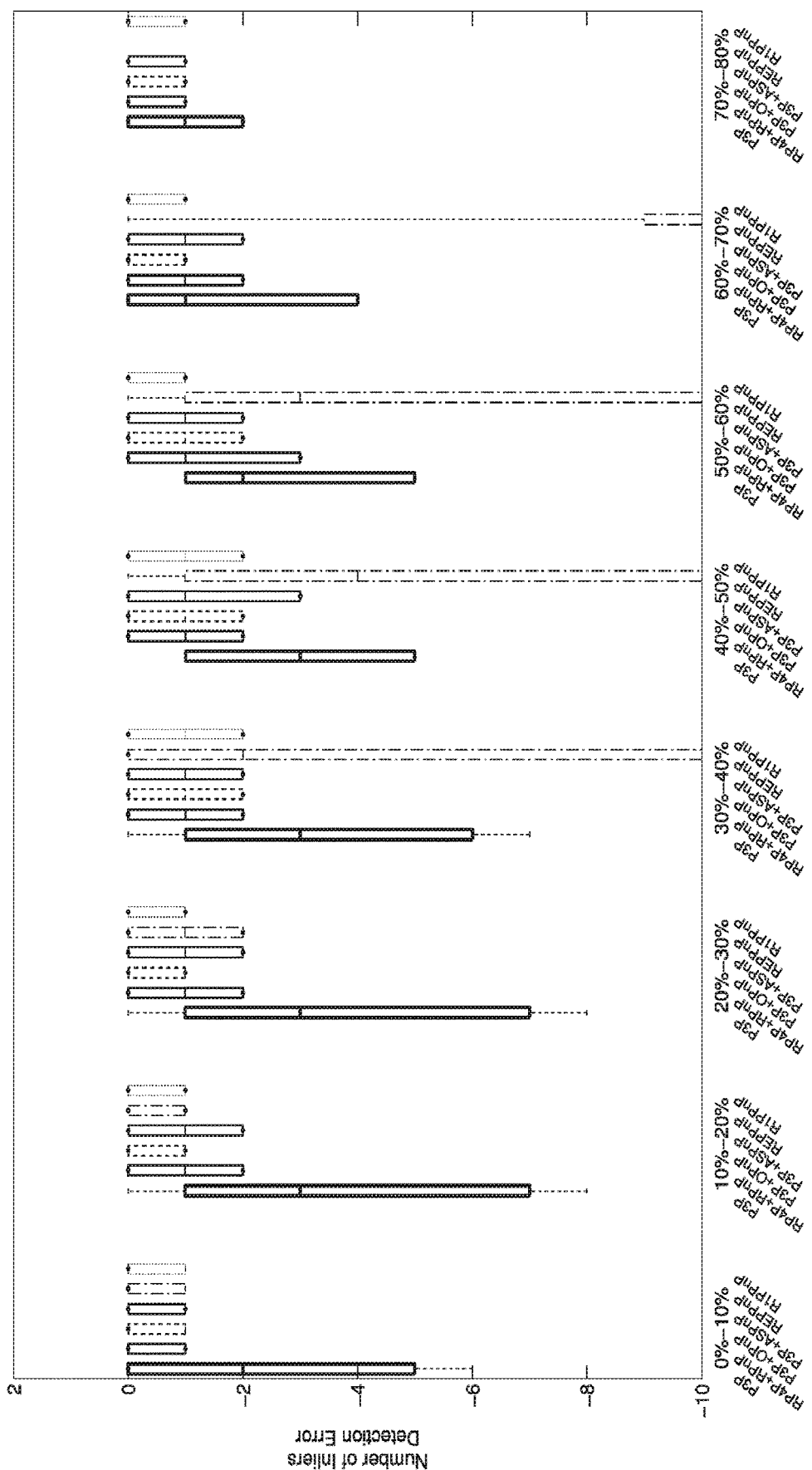
FIG. 14D is a graph of number of inliers detection error for the methods, in FIG. 14A.

As shown in FIG. 14C, a graph of runtime of the various methods, as the percentage of outliers increased, the runtime of R1PPnP did not grow significantly compared with conventional RANSAC+P3P or P4P methods. When $p_{outliers}$<30%, R1PPnP was much more accurate than pure RANSAC+P3P as shown in FIG. 14A and FIG. 14B. To improve accuracy, RANSAC+P3P needs other PnP methods, such as OPnP or ASPnP, as the final refinement step. Compared with other refinement PnP methods, R1PPnP was much faster than OPnP even when the percentage of outliers was small. FIG. 14D shows number of inliers detection error (i.e., number detected minus the maximum detected) for the methods, with zero implying that method found the most outliers.

Figure 15:
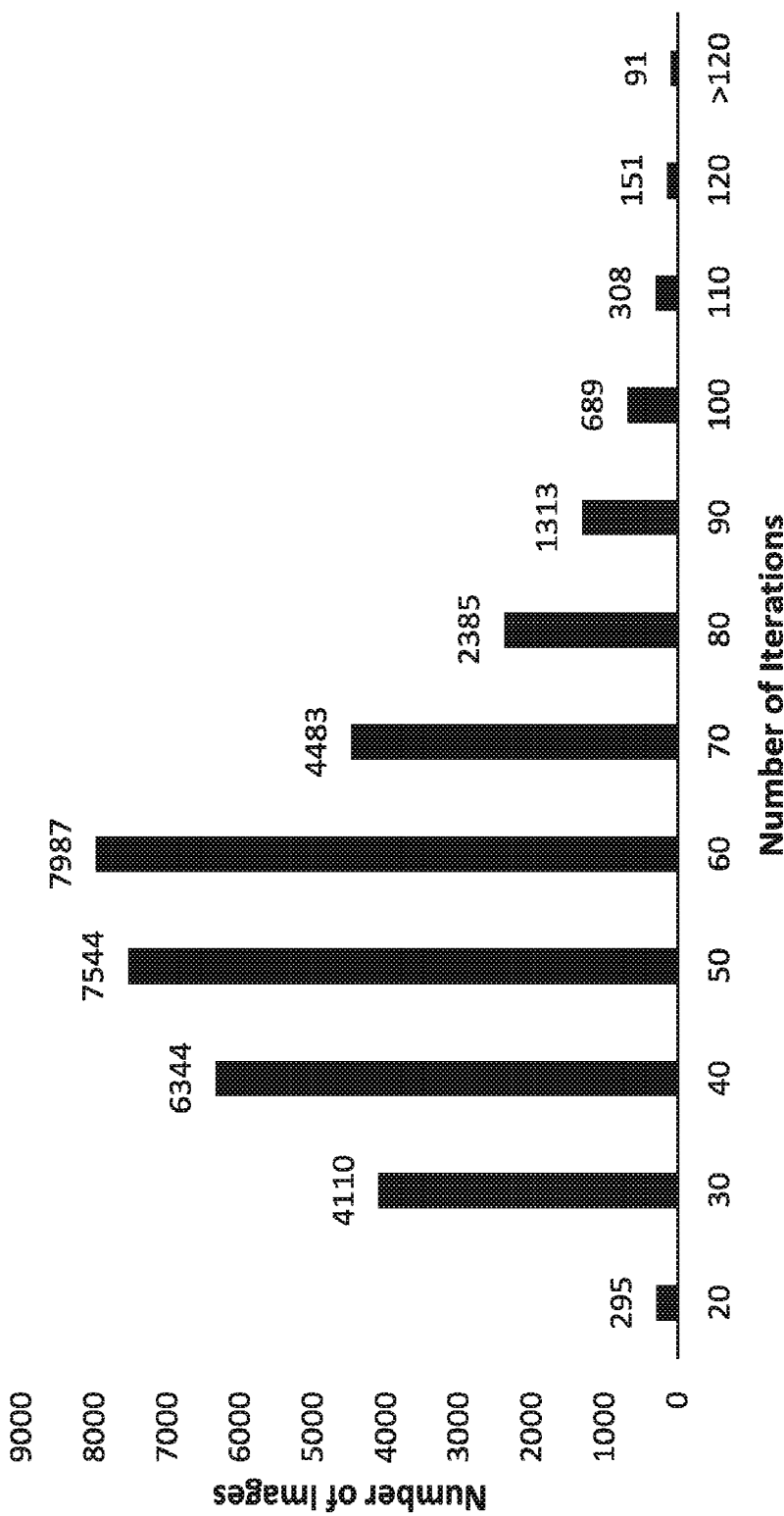
FIG. 15 shows a histogram of the number of R1PPnP iterations on all 35700 images.

FIG. 15 shows a histogram of the number of R1PPnP iterations on all 35700 images. As shown in FIG. 6, the iteration number includes iterations with the re-weighting mechanism that obtained the best results in RANSAC trials, and the subsequent refinement iterations without re-weighting. The average number of required iterations is 51.3.

Thus, the disclosure provides a fast and robust P n P solution named R1PPnP for tackling the outliers issue. We integrate a soft re-weighting method into an iterative PnP process to distinguish inliers and outliers, and employ the 1-point RANSAC scheme for selecting the control point. The number of trials is greatly reduced compared to conventional RANSAC+P3P or P4P methods; hence, it is much faster. Synthetic and real world experiments demonstrated its feasibility. Another advantage of R1PPnP is that its code implementation is relatively easy because all steps of R1PPnP involve only simple calculations. For example, its minima avoidance mechanism only requires to compute the determinant of the rotation matrix and to make $\lambda_{new}=1/\lambda_{old}$. Appropriate situations to replace conventional RANSAC+P3P methods with R1PPnP can include when the percentage of outliers and/or the image white noise is large. R1PPnP is more appropriate for large point clouds because of its low time complexity and the requirement to try control points.

The above-described framework can be applied to a variety of applications. As one non-limiting example, the above framework may be used in an environment that undergoes non-rigid motion or movement. For example, the environment may include that provided by a two-dimensional stereo video-based 3D reconstruction of tissue surfaces.

To overcome the difficulty in registering the multimodal images, 3D information can be extracted from 2D optical videos, which is still an open problem and is especially challenging when the surface texture is low. The systems and methods provided herein can be used to reconstruct textured 3D models of tissue surfaces from stereo optical videos in real-time. The textures on the reconstructed tissue surface models have the same resolution as the input video frames, which can greatly facilitate surgical navigation for the following reasons: (1) During surgery, only a small area of the target tissue may be exposed and landmarks that can be automatically recognized are often invisible. In addition, blood or surgical smoke may occlude the target tissue. Hence, it is important to provide high resolution textures to help the clinicians to recognize the tissue from the reconstructed models and then perform manual registration. (2) Intuitive visual feedback as part of a surgical navigation system is also very important for tumor localization. And with high resolution textures, clinicians are able to visualize the in vivo scene from different angles intuitively.

Stereo optical imaging modalities have been widely used in the operating room to provide depth perception to the surgeon. In the past decade, many efficient stereo matching methods have been proposed to estimate depths of image pixels by establishing pixel-to-pixel correspondences between the stereo images, the results of which can be further refined to generate fine 3D models. Stereo matching methods can be roughly classified into global and local methods. Global methods use constraints on scan-lines or the whole image, which are able to handle low texture regions by using explicit or implicit interpolation. However, global methods have high computational complexity and are inappropriate for real-time applications. In contrast, local methods only use constraints on a small number of pixels surrounding the pixel of interest, which are fast but are difficult to handle low texture regions. In this disclosure, we propose effective outliers removal, hole filling and smoothing methods as the post-processing steps for the local stereo matching methods, which have low computational complexity low and are appropriate for graphics processing unit (GPU) parallel computation.

Stereo matching-based 3D reconstruction is highly dependent on the texture of the observed object. However, the surface texture of tissues, such as lung and liver, is not rich enough to be observed at a distance due to the limited camera resolution and poor illumination condition. Another important reason to use a small camera-tissue distance is that the baseline of stereo imaging modalities is usually short, which result in large uncertainties when estimating large depths. However, due to the limited field of view, a small camera-tissue distance will lead to only a small area of the surface that can be reconstructed from the pair of stereo images, which is insufficient to perform accurate registration between pre- and intraoperative 3D models. To solve the contradiction between the accuracy of 3D reconstruction and registration, we propose to scan the tissue surface at a close distance and perform stereo matching on the acquired stereo images, then mosaick the 3D models at different time steps according to model alignment obtained by simultaneously localization and mapping (SLAM).

SLAM is one topics of substantial attention in the robotics navigation field. SLAM aims to estimate the camera motion and reconstruct the surrounding environment in real-time. To date, SLAM methods have proven effective in reconstructing large environments and estimating long motions, hence it seems to be a reasonable assumption that the accumulative errors of SLAM methods is minimal for the small in vivo environments. SLAM methods are often based on feature points matching to establish correspondences between video frames. However, for tissue surfaces with low and/or repeating texture under varying illumination conditions, feature matching is challenging and a large percentage of matching outliers may cause failure of the SLAM methods.

In order to overcome the difficulties in feature matching and improve the robustness of mosaicking, we first propose a novel histogram voting-based method to select possible inliers from the feature matching results. Then, using the selected possible inliers as the control points, we extend our previous work and propose a novel perspective-n-points (PnP) algorithm called as DynamicR1PPnP to estimate the camera motion, which can remove incorrect and build new matches dynamically. Finally, we propose to integrate feature matching and iterative closest points (ICP)-based costs into an optimization method to refine the camera motion estimation results. The main algorithms involved in our SLAM framework are implemented in CUDA C++ and run on the GPU.

The below sections are organized as follows. In the "Stereo Matching" section, we describe the process of the stereo matching method and provide the details of its GPU implementation. The SLAM-based model mosaicking method, including histogram voting-based inliers selection, DynamicR1PPnP and GPU-based BA+ICP, is introduced in the "Model Mosaicking" section. Evaluation results on ex vivo and in vivo data are presented in the "Experiments" section.

Optical video-based 3D reconstruction of tissue surfaces can improve the accuracy of intraoperative navigation. Stereo matching is one set of 3D reconstruction methods in surgical navigation applications, which estimates pixel disparities by comparing stereo images. Stereo matching is an active topic in the computer vision field and a large number of methods exist. Stereo matching methods can be roughly classified into global and local methods. Global stereo matching, such as dynamic programming and graph cuts, exploit nonlocal constraints to reduce sensitivity to regions that fail to match due to low texture and occlusions, which make explicit smoothness assumptions to solve an optimization problem. However, the high time complexity makes global stereo matching difficult to be real-time, hence most current real-time 3D reconstruction systems are based on local stereo matching.

Local stereo matching methods estimate disparities of pixels by computing matching matrices between small and local image patches. There exist many metrics to evaluate the similarity between two image patches. The most straightforward one is window-based matching costs, which compare the differences of squared image windows. Zero-mean normalized cross-correlation (ZNCC) is one of the most effective window-based costs due to its good robustness to illumination changes. However, such squared window-based methods cannot handle pixels near object edges because they may belong to different surfaces. To overcome this problem, non-parametric matching costs, such as rank and census methods and ordinal measures, were proposed to handle object boundaries. Another class of effective methods is based on support window methods, such as PatchMatch, which uses varying shape of the matching window. To achieve better accuracy, researchers propose to dynamically update the weights of pixels within the support window. For our task, the needs of handling tissue edges or occlusion are not high because usually only one target tissue needs to be reconstructed and the surgeons may simply remove the instrument during the scan. Hence we use ZNCC matching in our method, which is fast on the GPU. Our main contribution of the stereo matching part is that we propose several effective post-processing steps to address the low texture problem, which can also be used for the refinement of other local stereo matching methods.

Many real-time stereo matching systems are based on ZNCC. To achieve real-time performance, it is essential to reduce the number of candidate disparities for local stereo matching methods. For example, one group proposed a disparities searching strategy by first generating disparities for all pixels randomly, and then iteratively replacing the disparity of a pixel with that of its neighboring pixel if the new value suggests a better ZNCC matching. Another group matched a sparse set of salient regions using stereo Lucas-Kanade and propagated the disparity around each matched region. They reported a 10 Hz updating rate for images with 360×240 resolution. The development of GPU or FPGA based parallel computational algorithms can greatly accelerate the image patch matching process. One group reported a 100 Hz update rate for stereo images with 1280×1024 resolution using a NVIDIA Titan X GPU. Our CUDA C++ implementation achieves a 200 Hz updating rate for the 960×540 resolution and 100 candidate disparities, which is sufficient for our surface reconstruction system.

3D models generated by stereo matching are limited to the field of view, which may be too small for surgical guidance. Structure-from-motion (SfM) or simultaneously localization and mapping (SLAM) methods are able to align video frames at different time steps and generate a much larger synthetic field of view, which have been employed for 3D reconstruction of tissues. For example, one group proposed to expand the field of view based on SLAM. Most SfM and SLAM methods only reconstruct sparse feature points, which poorly describe the surgical scene.

Dense SLAM methods have also been developed to generate dense tissue models in real-time. Some have proposed an EKF-SLAM-based method for dense reconstruction. EKF-SLAM suffers from low accuracy and is difficult for representing loop closing. Recently, others proposed a monocular vision-based dense tissue 3D reconstruction method by using ORB-SLAM to estimate the camera motion. However, because ORB-SLAM is based on ORB features and RANSAC+P3P for camera motion tracking and loop closing, its robustness is not satisfying with low texture scenes. In this disclosure, we propose novel camera motion tracking algorithms and a more robust SLAM framework to improve the robustness of camera pose estimation with low texture surfaces.

Another way to perform real-time dense reconstruction is to combine sparse SLAM and stereo vision, the idea of which is closely related to the famous KinectFusion work, which merges the raw depth map provided by Microsoft Kinect to generate the fine models. It is a natural idea to replace the depth map with the results of stereo matching. However, the most difficult part is to align the depth map by SLAM, and KinectFusion is based on the ICP method. However, due to the narrow field of view and the smooth surface of tissue, ICP-based alignment cannot achieve accurate registration in the tangential directions.

Stereo Matching

After stereo camera calibration, physical depths of stereo image pixels can be directly computed from the disparities. We used the Matlab Computer Vision Toolbox to calibrate the stereo laparoscope and our C++ code to convert image disparities to physical depths is equivalent to the Matlab 'reconstructScene' function. For local stereo matching methods, the estimation of disparities at low texture regions is difficult due to the lack of direct corresponding information between left and right images. However, low texture regions are common on tissue surfaces due to tissue optical properties, limited image resolution, poor image quality and poor illumination conditions. Most stereo matching methods rely on interpolation to propagate information from highly textured regions to low texture regions. For example, by interpolating between edges, a textureless flat wall can be reconstructed accurately. However, tissue surfaces have more complex shapes, and interpolation-based methods may not be accurate at distant regions. Hence, we do not seek to estimate disparities of all pixels in the stereo matching step, but rely on the subsequent mosaicking step to generate more complete and larger models of tissue surfaces.

Figures 16A, 16B:
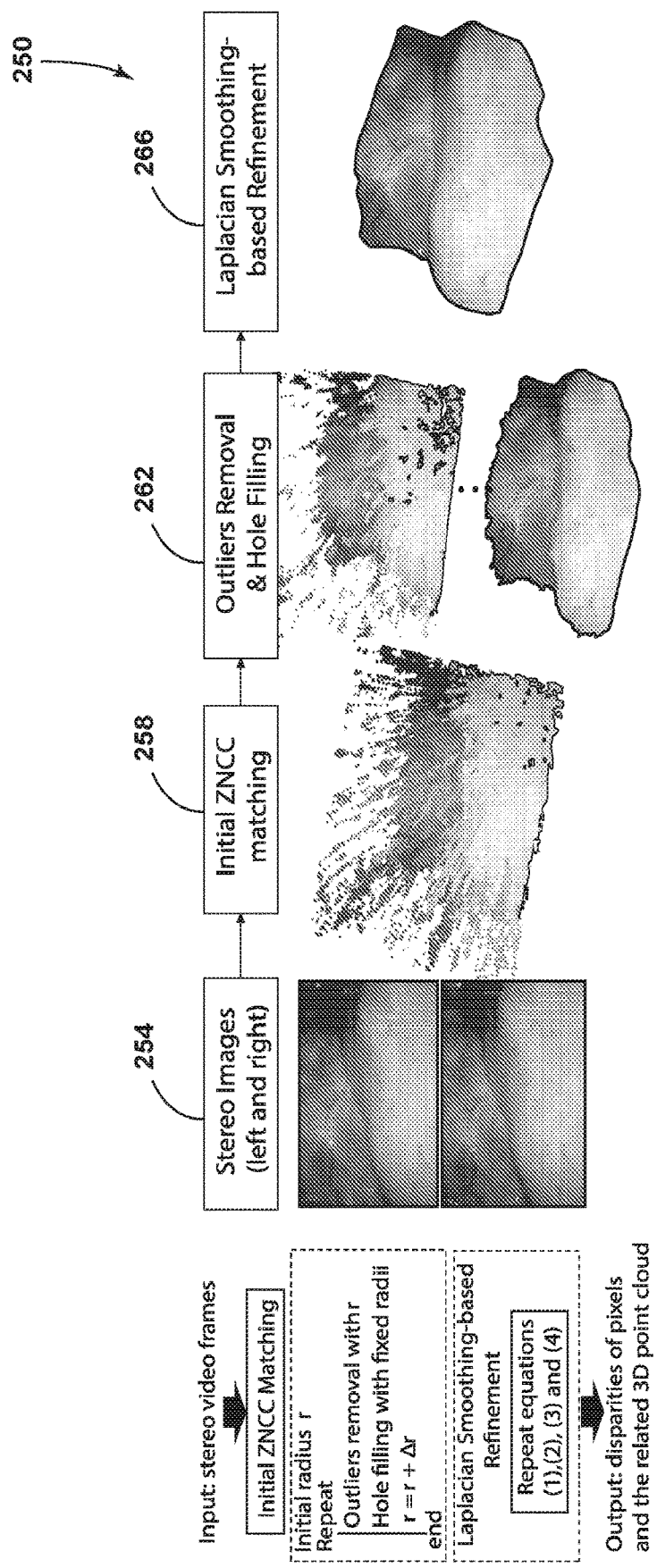
FIG. 16A is exemplary pseudocode of a stereo matching method.
FIG. 16B is a flowchart a stereo matching process with a pair of stereo laparoscopic images captured during a lung surgery at a hospital.

FIG. 16A shows exemplary pseudocode of a stereo matching method. FIG. 16B shows an example of a stereo matching process 250 with a pair of stereo laparoscopic images captured during a lung surgery at a hospital. Images are shown at various steps in the process 250 to represent the step. The texture on the tissue surface is low. At 254, two stereo images are input. At 258, the stereo matching process matches the stereo images suing zero-mean normalized cross correlation (ZNCC). At 262, the stereo matching process removes outliers and fills holes iteratively based on the matched stereo images. At 266, the stereo matching process refines the outlier-removed and hole-filled image output at 262 using a Laplacian Smoothing-based technique.

To overcome the high time complexity drawback of global stereo matching methods and difficulty to handle low texture regions of local stereo matching methods, we propose a novel stereo matching framework as shown in FIG. 16 to enlarge the radius of constraints of local stereo matching. First (at 258), we employed the zero-mean normalized cross correlation (ZNCC) metric to evaluate similarities between local image patches to estimate disparities of pixels. Then, we developed a robust outliers removal and hole filling method to refine (at 262) the ZNCC matching results. The first two steps provide discrete initial disparity values that are from the candidate disparities pool for the final refinement step (at 266), where we integrate the ZNCC metrics and the smoothing cost into a modified Laplacian smoothing framework. This method is able to build large connections among pixels when minimizing the cost function, and is easier to compute than conventional Gauss-Newton (GN) or Levenberg-Marquardt (LM) algorithms. It is worth clarifying that we are not implying that ZNCC is the best metrics, however since our stereo matching methods are mostly post-processing steps, it is easy to replace ZNCC with other local matching metrics. The algorithms in our stereo matching method work in parallel with respect to each pixel, and are highly appropriate for GPU parallel computing.

ZNCC-Based Local Matching

The local stereo matching method first generates disparities for all pixels randomly, and then iteratively replaces the disparity of a pixel with that of its neighboring pixel if the new value suggests a better matching. This process has demonstrated high efficiency and even CPU-based serial computation can be real-time (2-3 Hz). Another advantage is that this type of method implicitly takes into account smoothing among pixels. However, in practice we found that this method is not suitable for the case of smooth tissue surface because pixels that have the same disparity are often distributed in a narrow belt, which makes it difficult to propagate a correct disparity value and many iterations are needed. In addition, these methods cannot make full use of the GPU parallel computing ability, because the propagation process can only be parallelized to W and H threads alternatively, where W and H are image width and height respectively.

Our stereo matching method is based on the ZNCC metrics to evaluate similarities between local image patches. In non-limiting experiments we used a window size of 11×11 pixels. To make full use of GPU parallel computing ability, we developed a brute force way by launching GPU threads for each pixel to test the candidate disparity values. To achieve higher computational speed, in the matching window we only use every other pixel values, which is distributed as a chessboard. The details of our GPU implementation are briefly described as follows: For images with a resolution of W×H, our CUDA implementation launches H CUDA blocks and each CUDA block has W threads. We cache neighboring image rows into the GPU shared memory for each CUDA block to avoid the slow I/O speed of global memory. With a 960×540 resolution and 100 candidate disparity values, the runtime of our GPU-based ZNCC matching method is around 5 ms.

Outliers Removal and Hole Filling

The initial ZNCC matching may result in a large amount of outliers. Our outliers removal and hole filling method is under a reasonable assumption that the tissue surface is relatively smooth. Hence, an inlier should have sufficient number of neighboring points that has smooth change of disparities. Denoting r as the detection radius, we detect along each 8-radial directions within radius r and check if the disparity of two neighboring points is smaller than a pre-defined threshold (=2.5 in our experiments). If none of the 8-radial directions satisfies this smooth disparity assumption, the point will be recognized as an outlier and removed.

We developed two hole filling methods. For a left-image pixel that cannot find its corresponding right-image pixel, the first method searches along the pixel's 8-radial directions and the second method searches within a radius of the pixel. In our experiment the two radii for the hole filling methods are fixed, which are 50 and 20 pixels respectively. If sufficient number of neighboring points have a valid disparity value, then disparity of this pixel is filled according to interpolation. In the hole-filling step the iterations are performed within a radius, which avoids interpolation at distant areas.

However, when removing outliers, it is difficult to pre-define a radius r for all cases. A small r may keep too many outliers and a large r may remove inliers. To removal outliers and preserve as many inliers as possible, we propose to use an iterative process that alternately performs outlier removal and hole filling, as shown in FIG. 16A. In this process we gradually enlarge r with a step $\Delta r$ when detecting outliers. Hence, disparities that are removed may then be filled, and neighboring inliers will not be removed with larger r. In our experiments, the number of outliers removal and hole filling iterations is 3; the radius r is 10 pixels initially and increases at a step of $\Delta r=10$ pixels.

Improved Laplacian Smoothing-Based Refinement

Further step to refine the estimated disparities is necessary because (1) the initial disparities after the first two steps are discrete values that are directly selected or interpolated from the candidate disparities and (2) relationships among pixels are not fully considered. Our refinement method is based on Vollmer's improved Laplacian smoothing method, which is able to avoid model shrinking compared with standard Laplacian smoothing. We integrate a cost function that consists of the ZNCC metrics and the smoothing cost into this improved Laplacian framework to allow for dynamically updating the disparities. The details of our refinement step are as follows:

We denote the discrete disparity of a pixel i as $o_i$, which initially is equal to the disparity value after the first two steps. The smoothed disparities at the kth iteration are denoted as $d_i^{(k)}$. After an initialization $d_i^{(0)}:=o_i$, the refinement method performs the following steps in the kth iteration:

$$d_i^{(k)} := \text{average}(o_j), \quad (28)$$

where j is the index of neighboring pixels of point i within a pre-defined radius, and we use the smoothing radius of 15 pixels in our experiments.

$$b_i = d_i^{(k)} - \alpha o_i - (1-\alpha) d_i^{(k-1)}, \quad (29)$$

where $b_i$ is introduced to avoid model shrinking. $\alpha \in [0,1]$ is a weighting coefficient and $\alpha=0.1$ in our experiment. And then $$d_i^{(k)} := d_i^{(k)} - \text{average}(b_j). \quad (30)$$

Equations (28), (29) and (30) are derived from Vollmer's Laplacian smoothing method, which generate continuous disparities $d_i$ by smoothing discrete disparities $o_i$. We further propose to update the discrete disparities $o_i$ in each iteration according to the minimization of a cost function that consists of the ZNCC metrics and the smoothing cost. Specifically, with an updated disparity $d_i^{(k)}$ in the iteration, we search within a disparity range $[d_i^{(k)}-5, d_i^{(k)}+5]$, and update the $o_i$ to the disparity value that minimizes $$o_i := \underset{o_i^*}{\text{argmin}}\, f_{zncc}(o_i^*) + \eta f_{smooth}(o_i^* - d_i), \quad (31)$$

where $f_{zncc}(o_i^*)$ is the ZNCC matching cost, which equals to the reciprocal of the ZNCC matching value when using a disparity $o_i^* \cdot f_{smooth}(o_i^*-d_i)=(o_i^*-d_i)^2$ is the smoothing cost because $d_i$ is the smoothed value of neighboring $o_j$. $\eta$ is a coefficient. The size of matching window affects $f_{zncc}(o_i^*)$, and with a 11×11 pixels window, we use $\eta=0.01$ in our experiments.

Some advantages of using this improved Laplacian smooth framework manifest in an able to naturally make use of the dynamically updated discrete disparities. This method is highly parallel to each pixel and suitable for GPU computation.

Model Mosaicking

Figure 17:
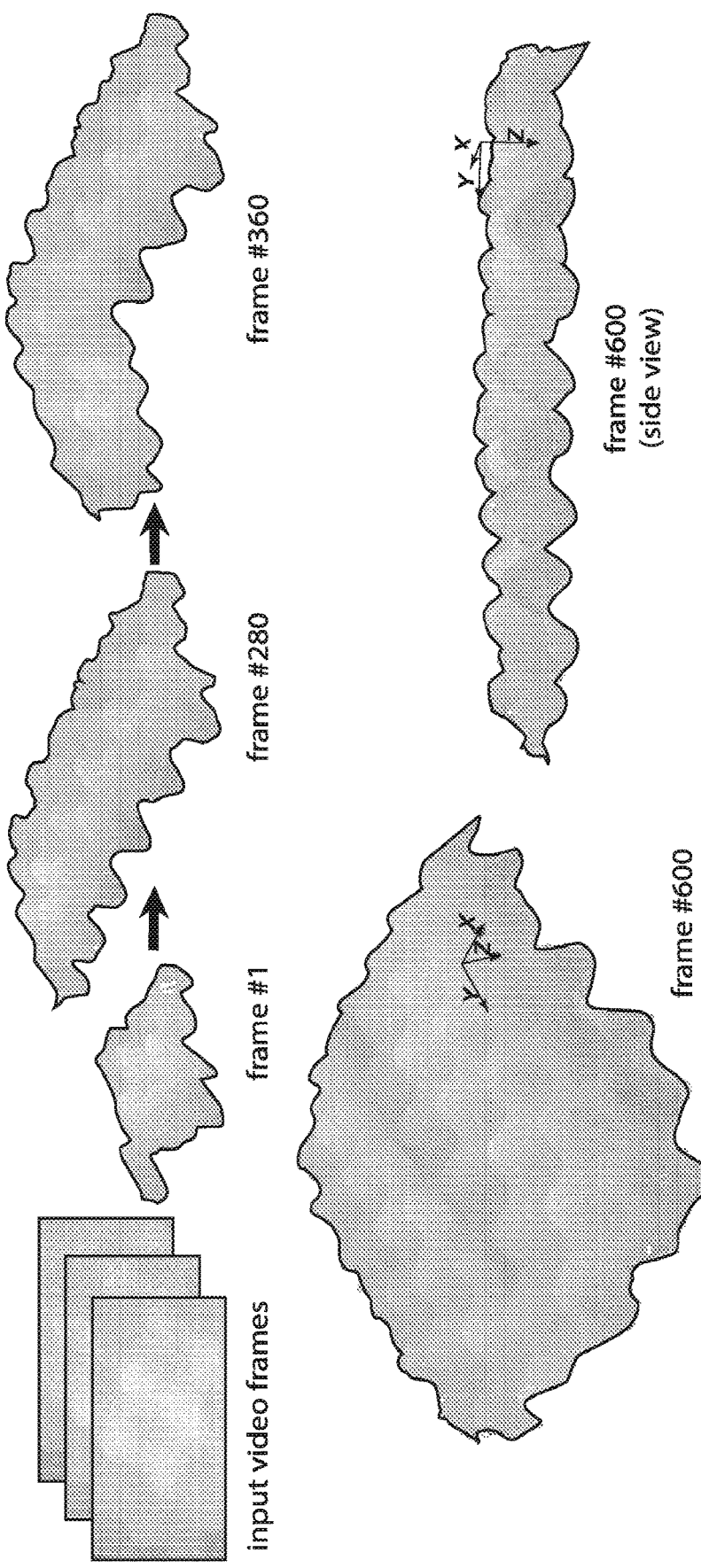
FIG. 17 is an example of a model mosaicking process with a phantom.

We employ the truncated signed distance field (TSDF) method to mosaic the raw 3D point cloud generated from pixel disparities results of stereo matching and the camera calibration parameters to obtain the extended 3D model of the tissue surface, as shown in FIG. 17, which shows an example of our model mosaicking process with a phantom. The prerequisite to perform TSDF is to align the raw 3D point cloud accurately, which is equivalent to the estimation of camera motion in this video-based 3D reconstruction problem. Conventional iterative closest points (ICP)-based model alignment is difficult to handle smooth tissue surfaces. Another way to align models is based on image feature points matching. However, due to the low texture and varying illumination condition, feature matching is challenging and a large amount of outliers may exist. To overcome these problems, we propose a novel SLAM method that consists of fast and robust algorithms to handle the large percentage of feature matching outliers in real-time.

Figure 18A:
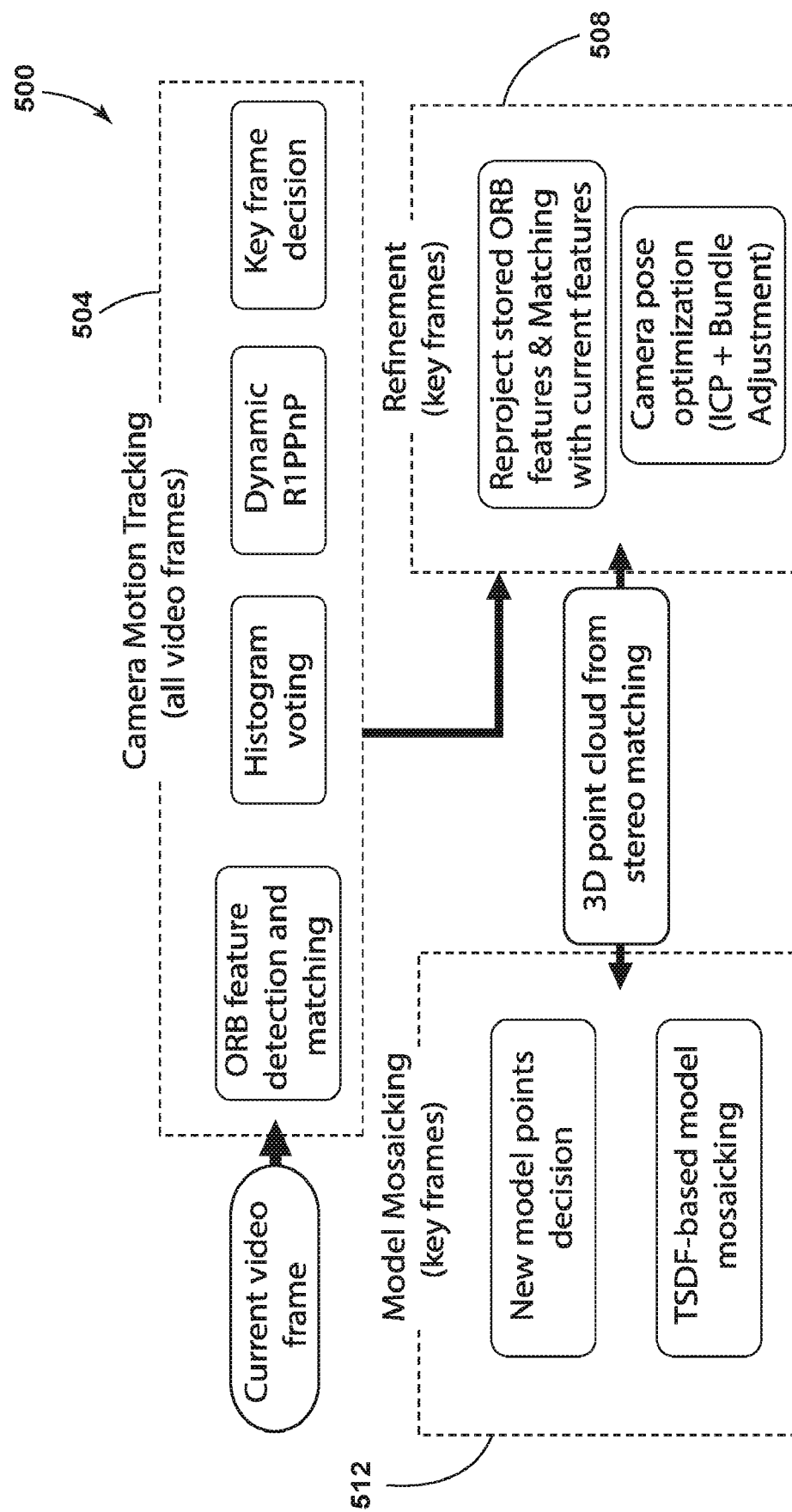
FIG. 18A is a flow chart of a three dimensional reconstruction method.
Figure 18B:
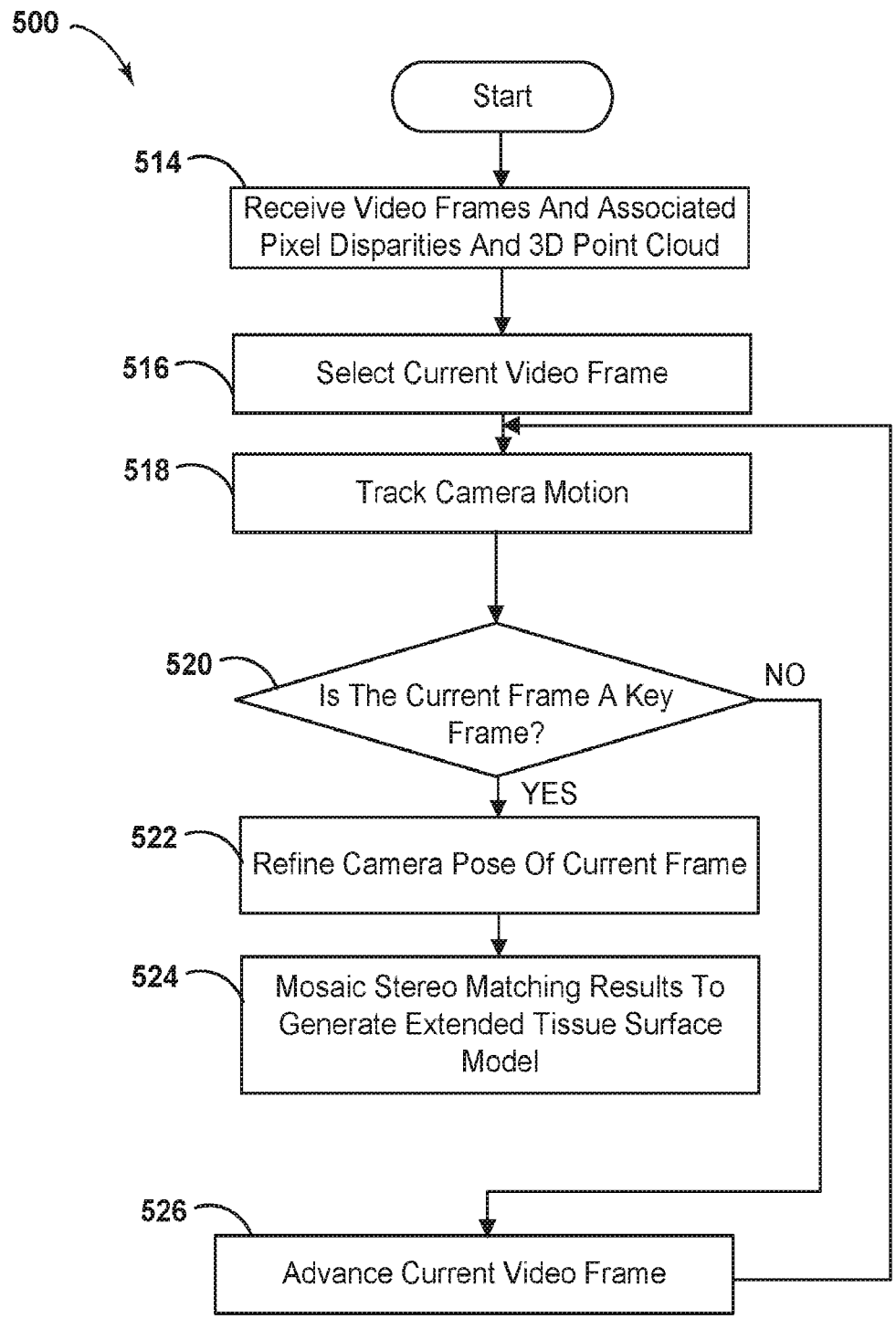
FIG. 18B is another flow chart of the three dimensional reconstruction method shown in FIG. 18A.
Figure 19A:
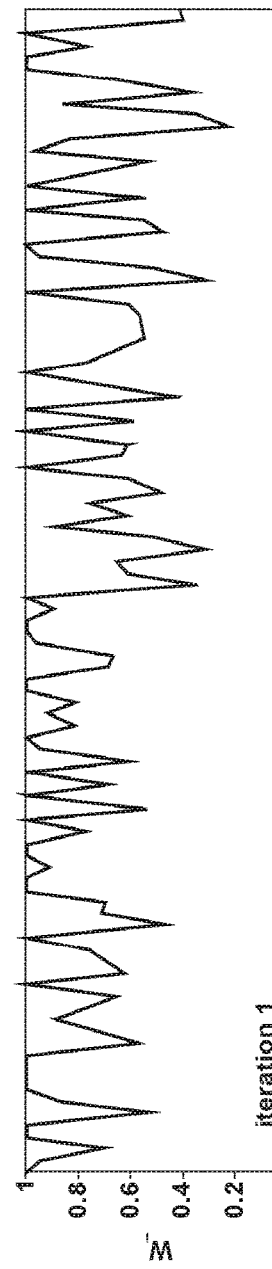
FIG. 19A is a graph of example changes of weights $w_i$ in R1PPnP iterations at first iteration.
Figure 19B:
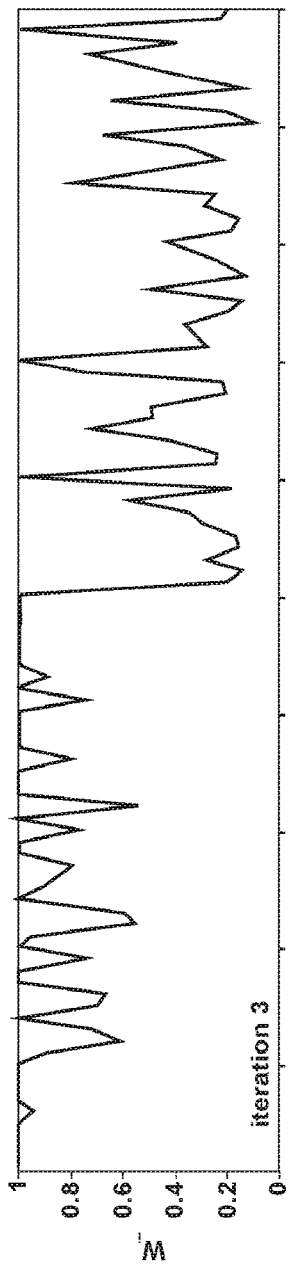
FIG. 19B is a graph of example changes of weights $w_i$ in R1PPnP iterations at third iteration.
Figure 19C:
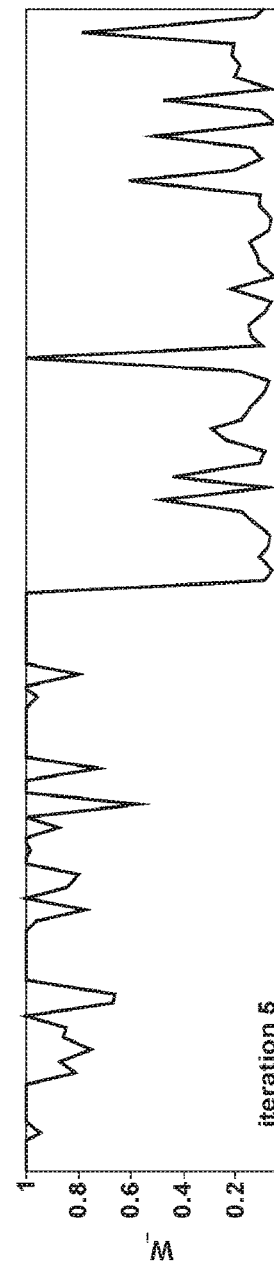
FIG. 19C is a graph of example changes of weights $w_i$ in R1PPnP iterations at fifth iteration.
Figure 19D:
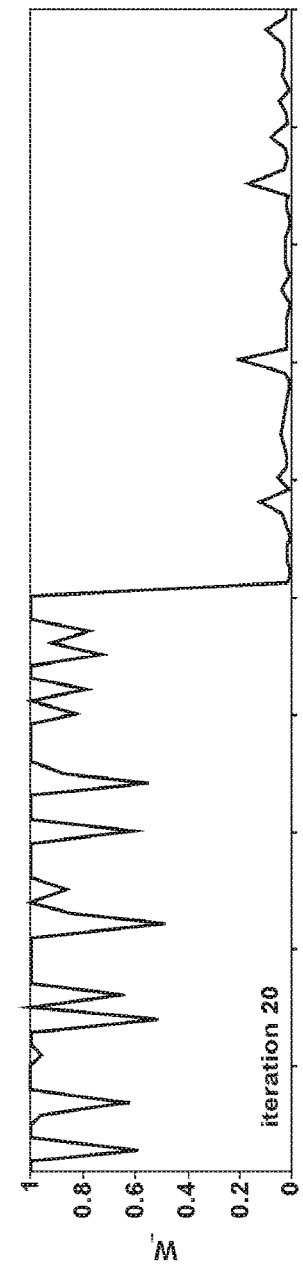
FIG. 19D is a graph of example changes of weights $w_i$ in R1PPnP iterations at twentieth iteration.

A flow chart of a 3D reconstruction method 500, which is based on SLAM as well as DynmaicR1PPnP, which will be explained below. is shown in FIG. 18A, which mainly consists of three modules. A first module 504 tracks the camera motion between adjacent video frames according to ORB feature matching, which is mainly based on a novel and robust PnP algorithm called DynamicR1PPnP. A second module 508 aims to refine the camera motion estimation results at key frames and eliminate the accumulative error, which is based on the minimization of ICP and bundle adjustment (BA) costs. A third module 512 performs TSDF-based model mosaicking and manages feature points. In the following section, we will introduce the details of the involved algorithms included in the modules 504-512. FIG. 18B shows another flow chart of the 3D reconstruction method 500, and will be described further below.

Histogram Voting-Based Matching Inliers Preselection

The 3D reconstruction method 500 is based on the ORB feature, which is much faster to detect and match than the conventional SURF feature, and has been widely used in real-time SLAM systems, such as the ORB-SLAM method.

However, the low and/or repeating texture of the tissue surface and varying illumination condition may result in a large amount of incorrect feature matches. In practice we observed that the percentage of outliers may be larger than 85%, making the traditional RANSAC+P3P-based outliers removal method slow. In addition, the small number of correct matches also decreases the accuracy of camera motion estimation. Hence, it is necessary to design algorithms to handle the large percentage of matching outliers.

ORB matching is performed between two adjacent video frames for camera motion tracking. Under a reasonable assumption that the camera motion, especially the roll angle, between adjacent video frames is minimal during the surface scan, we propose to utilize the displacements of matched ORB features between two adjacent images to roughly distinguish correct and incorrect ORB matches. Specifically, we denote the image coordinates of matched ORB features at two images as $[u_i^{(1)}, v_i^{(1)}]$ and $[u_i^{(2)}, v_i^{(2)}]$, i=1, . . . , N, where u and v are the x- and y-image coordinates in pixels. A correct match k should have a similar displacement $[u_i^{(2)}-u_i^{(1)}, v_i^{(2)}-v_i^{(1)}]$ with other correct matches. Hence, we first generate the histogram of $[u_i^{(2)}-u_i^{(1)}, v_i^{(2)}-v_i^{(1)}]$, and then consider the ORB matches that are close to bins with large histogram value more likely to be inliers, which will be assigned with higher priority to be the control points for the subsequent DynamicR1PPnP algorithm. It should be clarified that this histogram voting-based inliers preselection step may not be 100% correct, but it is fast and able to remove a large amount of outliers fast for the subsequent steps of the SLAM method.

DynamicR1PPnP

PnP methods, which aim to estimate the position and orientation of a calibrated camera from n known matches between 3D object points and their 2D image projections, have been widely used in SLAM systems for camera motion estimation. We propose to modify and improve our previous R1PPnP work to handle the problem of small number of matching inliers in the task of tissue surface reconstruction. In this section, we first briefly introduce the original version of R1PPnP and then introduce our modification.

R1PPnP is based on a pin-hole camera model, which is $$u_i = f\frac{x_i^c}{z_i^c}, v_i = f\frac{y_i^c}{z_i^c}, \quad (32)$$

where f is the camera focal length, $x_i=[u_i, v_i, f]^T$ is the image homogeneous coordinate in pixels, and $X_i^c=[x_i^c, y_i^c, z_i^c]^T$ is the real-world coordinate with respect to the camera frame. Hence, we have $$X_i^c = \lambda_i^* x_i, \quad (33)$$

where $\lambda_i^* = z_i^c/f$ is the normalized depth of point i.

The relationship between the camera and world frame coordinate of point i is $$X_i^c = RX_i^w + t, \quad (34)$$

where $R \in SO(3)$ is the rotation matrix and $t \in R^3$ is the translation vector. R and t are the variables that need to be estimated in the PnP problem. Selecting a point o as the control point, we have $$X_i^c - X_o^c = R(X_i^w - X_o^w), i \neq o. \quad (35)$$

Denoting $S_i = X_i^w - X_o^w$, then, according to Equation (33) and Equation (35), $$\lambda_i^* x_i - \lambda_o^* x_o = RS_i. \quad (36)$$

We divide both sides of Equation (36) by the depth of the control point $\lambda_o^*$, and rewrite Equation (36) as $$\lambda_i x_i - x_o = \mu RS_i, \quad (37)$$

where $\lambda_i = \mu \lambda_i^*$ and $\mu = 1/\lambda_o^*$ is the scale factor. We have $$t = 1/\mu x_o - RX_o^w. \quad (38)$$

which suggests that t can be computed from R and μ.

The geometrical relationships of R1PPnP is shown in FIG. 2. R1PPnP combines a re-weighting strategy and the 1-point RANSAC framework to reduce the effects of outliers. The 1-point RANSAC framework randomly selects one match as the control point o and then alternatively update R, μ and $\lambda_i$ to minimize the cost function $$f(R, \mu, \lambda_i) = \Sigma_{i=1, i \neq o}^N w_i \|\lambda_i x_i - x_o - \mu RS_i\|^2, \quad (39)$$

where $w_i$ is the weight of point i and is dynamically updated in the iteration process according to $$w_i = \begin{cases} 1.0 & \text{if } e_i \leq H \\ H/e_i & \text{if } e_i > H \end{cases} \quad (40)$$

where $e_i$ suggests the reprojection error of point i with the current R and μ during iteration. H is the inliers threshold that points with final reprojection errors smaller than H are considered as inliers, and in our experiments we use H=5 pixels. The reweighting rule Equation (40) suggests that a point with a large reprojection error will have a small weight during the estimation of camera pose, as shown in FIG. 19.

FIGS. 19A-D are graphs of example changes of weights $w_i$ in the R1PPnP iterations at first, third, fifth, and twentieth iterations respectively. In this example, the first 50 matches are inliers and the others are outliers. With the iteration, the weights of outliers decreases and their effects on camera motion estimation are reduced. Our experimental results (described above) showed that R1PPnP has state-of-the-art performance compared with conventional RANSAC+P3P methods to handle matching outliers.

The 3D reconstruction method 500 uses the preselected matches according to the histogram voting results as the control points o in the R1PPnP algorithm. However, when the number of feature matching inliers is small, R1PPnP or conventional RANSAC+P3P methods cannot estimate the camera motion accurately. Compared to obtaining correct matches, detecting consistent sets of feature points from two overlapped images is relatively easier. Based on this observation, we modified the R1PPnP method to dynamically update the feature matching relationships as follows: The camera pose is updated in an iterative process and the re-projection of stored feature points is updated accordingly. When the distance between a current feature point i and the re-projected stored feature point j is small, it should be considered as a possible correct match and we will add this candidate match dynamically, and the weight $w_{i,j}$ is updated according to $$w_{i,j} = \min(H/e_{i,j}, 1) \text{ if } e_{i,j} < \eta H \quad (41)$$

where $\eta > 1$ is a coefficient and in our experiments we use $\eta = 2.0$. Then, we perform normalization by $$w_{i,j} = w_{i,j}/(\Sigma_j w_{i,j} + w_i), \quad (42)$$

where $w_i$ is the weight of the original matches provided by ORB feature matching.

In order to reduce or eliminate incorrect matches that happen accidently in the iteration process, we decrease the weight $w_{i,j}$ if it is a newly observed candidate correspondence $$w_{i,j} = \min((k-k_0)/T, 1) w_{i,j} \quad (43)$$

where k is the current iteration index, $k_0$ is the first iteration index when this candidate correspondence is observed. T is a pre-defined number and in our experiments we use T=5.

Key Frame Decision

A frame is recognized as a key frame if it satisfies the following conditions: (1) There are at least 50 correct ORB matches when using DynamicR1PPnP, and (2) It has been at least 10 frames since the last key frame, or the difference between the camera pose of this frame and the last key frame is larger than a threshold. The camera pose difference is defined as $$\|t_{diffence}\| + 20 \min(\|E_{diffence}\|, 2\pi - \|E_{diffence}\|, \quad (44)$$

where $E_{diffence}$ and $t_{diffence}$ are the differences between the Euler angles and translations respectively. In our experiments we may use different pose thresholds for different data because the number of video frames and the tissue scale varies. A large pose threshold suggests that key frames are distant from each other and due to illumination changes, the textures on the mosaic may not look very smooth, but in general this pose threshold that determines key frames is not sensitive.

Refinement of Camera Motion Estimation

In the camera motion tracking stage, the 3D coordinates of feature points are directly obtained from stereo matching. The estimated camera poses are not accurate enough and bundle adjustment (BA)-based refinement is necessary. We also take into account the ICP-based distance between current stereo matching model and the existing model to improve the robustness of the SLAM method because feature matching with previous key frames may fail due to low texture.

We first try to match the ORB features of current key frames with those of previous key frames to eliminate accumulative error. Our SLAM algorithm stores the feature points of previous key frames for reducing the accumulative error. With the camera motion tracking results, we select several previous key frames that have enough overlapped areas with the current key frame as the candidates. Then, we perform ORB matching with the candidate previous key frames and perform DynamicR1PPnP to detect correct matches.

Then we apply the optimization method to refine the camera motion estimation results. At a key frame with index T, we refine the camera pose estimation results by minimizing the cost function $$f_{total}(R_t,t_t,x_i)=f_{BA}(R_t,t_t,x_i)+\beta f_{ICP}(R_T,t_T), t\in\Omega \quad (45)$$

where $\Omega$ is the set of indices of video frames, which includes the current key frame T, all frames between the last key frame and current key frame T, and the matched previous key frames. $R_t$ and $t_t$ are the camera rotation and translation at video frame t respectively. $x_i$ is the coordinate of feature point i. $\beta$ is a weighting coefficient, which is dynamically adjusted according to the ratio of the number of feature points and ICP points. In our experiment we use $\beta=0.1\times$ number of feature points/number of ICPpoints.

The first term of Equation (45), $f_{BA}(\cdot)$, is the standard local BA cost that aims to minimize the re-projection error, which only considers video frames that are included in $\Omega$. In this term, we fix the pose of the last key frame and the feature points observed in the last key frame to avoid scale drift.

Figure 20:
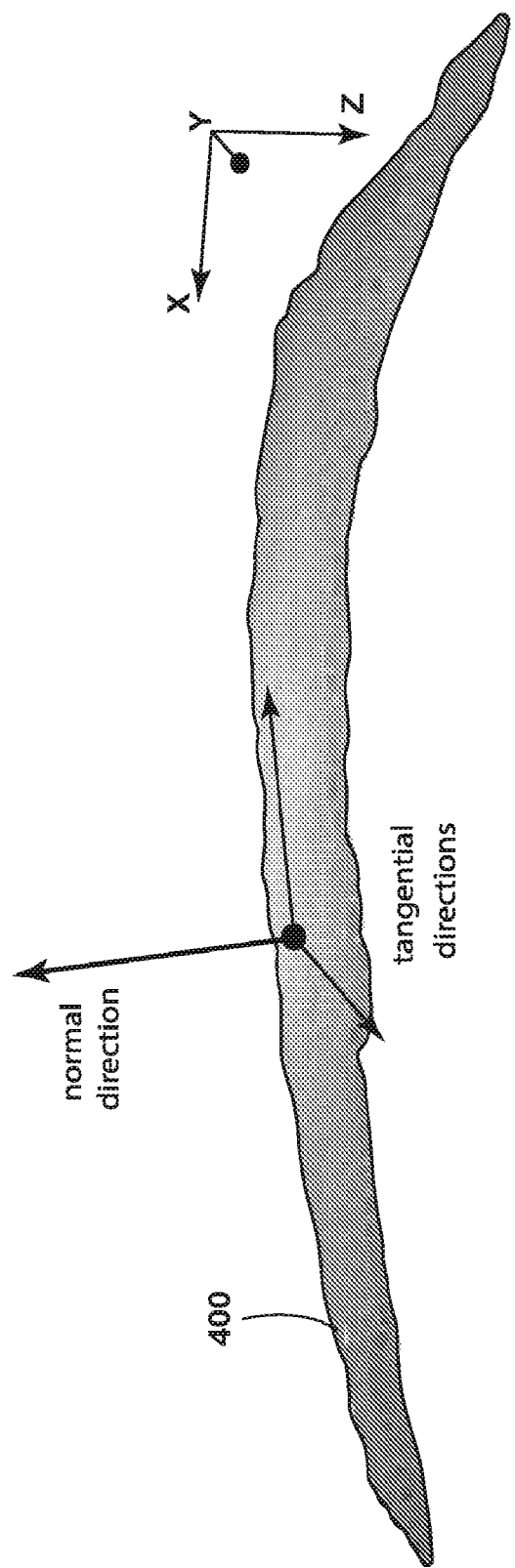
FIG. 20 is a graph of reconstructed 3D point cloud including normal and tangential directions in relation to a point included in the point cloud.

The second term of Equation (45), $f_{ICP}(\cdot)$, aims to minimize the distance between the existing 3D model and the current stereo matching model at key frame T, which is $$f_{ICP}(R_T,t_T)=\Sigma_i \rho \psi(n_i(R_T p_i+t_T-q_i)), \quad (46)$$

where $p_i$ are points of the existing model, and $q_i$ are points of the current stereo matching model that has the same re-projection pixel coordinate with $R_T p_i+t_T$. $\psi(\cdot)$ is Tukey's penalty function to handle outliers. $\rho=1$ if $q_i$ has a valid depth, otherwise $\rho=0$. $n_i$ is the normal direction of $q_i$ obtained from the stereo matching point cloud, which allows the template to 'slide' along the tangent directions, as shown in FIG. 20, which shows normal and tangential directions in relation to a point included on a reconstructed 3D point cloud 400.

To minimize the cost function Equation (45), a GPU-based parallel Levenberg-Marquardt (LM) algorithm is developed. The equation in the standard LM algorithm to update the variables is $$(J^T J+\lambda \operatorname{diag}(J^T J))x=J^T b, \quad (47)$$

where x is the vector of variables, J is the Jacobian matrix and b is the residual vector. $\lambda$ is a parameter that controls the updating step.

According to Equation (45), the variables to be estimated consist of camera poses and coordinates of feature points. Since a feature point may exist in most of the recent video frames, the structure of the whole Jacobian matrix j is large and dense. In order to accelerate the computation, we split the variables into two parts in our LM implementation and update the two parts of variables alternatively.

To update the coordinates of feature points, because each feature point is independent with respect to each other when the camera poses are fixed, we launch one GPU thread for each feature point and calculate the related Jacobian matrix and the residual re-projection errors.

We update the camera poses of different frames separately. Because only the camera pose at key frames considers the ICP term Equation (46), hence the main parameters of Equation (47) at key frames can be split to $$J^T J=J_{BA}^T J_{BA}+\beta^2 J_{ICP}^T J_{ICP}, \quad (48)$$

and $$J^T b=J_{BA}^T b_{BA}+\beta^2 J_{ICP}^T b_{ICP}. \quad (49)$$

We launch multiple parallel GPU threads to compute each row off. Then, we perform Cholesky decomposition to solve Equation (47).

GPU-Based TSDF Mosaicking

The basic idea of TSDF is to take the average value of the 3D coordinates of an area if it is observed multiple times, which is more accurate than the results of a single observation. Raw 3D point cloud can be obtained from key video frames by using our stereo matching method. We incrementally mosaic the stereo matching results to generate the extended tissue surface model based on the camera motion estimation results of SLAM. The extended tissue surface models are also in the form of 3D point clouds. Because we aim to obtain high resolution textures to provide better surgical navigation, the extended surface model usually include millions of points and traditional volume-based TSDF method may take too large amount of computer memory. To avoid this problem, we store the 3D coordinate and the RGB color for each point in the GPU memory without using volume grids. To build correspondences between the extended surface model and the current stereo matching results, we project the extended surface model to the current imaging plane according to the camera pose estimation results. This rasterize process is performed by using GPU parallel computation and is fast. For each pixel with a valid depth value in the stereo matching results, the related point in the extended surface model is merged with the stereo matching results by using the TSDF method. Pixels that are not covered by the reprojection are considered as new points and will be added to the extended surface model.

Since the light source is often equipped at the tip of the imaging modality, hence the image edge is often darker than the central area. In order to generate smooth texture of the model, we also use TSDF-like merging to update the RGB color of points. During RGB color merging, the TSDF updating weight is 1.0 if the point is at the center area of the image, and decreases as it approaches the image edge.

Referring now to FIG. 18B, another flow chart of the 3D reconstruction method 500 is shown. At 514, the method 500 can receive video frames, as well as disparities of pixels and a 3D point cloud associated with each video frame. The disparities of pixels and the 3D point cloud can be determined using a stereo matching method such as the stereo matching method 250 described above. The method 500 can then proceed to 516.

At 516, the method 500 can select a current video frame. The current video frame can be the first video frame in the video frames received at 514. The method 500 can then proceed to 518.

At 518, the method 500 can track camera motion. The method 500 can perform ORB feature matching and select inliers using a histogram-based voting process as described in the "Histogram Voting-based Matching Inliers Preselection" subsection, as well as estimate a camera pose including position and orientation using DynamicR1PPnP as described in the "DynamicR1PPnP" subsection. The method 500 can then proceed to 520.

At 520, the method 500 can determine whether or not the current frame is a key frame as described in the "Key Frame Decision" subsection. If the method 500 determines the current frame is a key frame (i.e., "YES" at 520), the method 500 can proceed to 522. If the method 500 determines the current frame is a not key frame (i.e., "NO" at 520), the method 500 can proceed to 526.

At 522, the method 500 can refine the camera pose of the current frame as described in the "Refinement of Camera Motion Estimation" subsection. The method 500 can then proceed to 524.

At 524, the method 500 can mosaic stereo matching results to generate an extended tissue surface model. The method 500 can generate the extended tissue surface model based on the camera pose of the current frame and the 3D point cloud associated with the current frame received at 514 as described in the "GPU-based TSDF Mosaicking" subsection. The method 500 can then proceed to 526.

At 526, the method 500 can advance the current video frame. The method 500 can set the current video frame to be the next chronological video frame of the video frames received at 514. If there is not a next chronological video frame, the method 500 can end.

Experiments

The source code was implemented in CUDA C++ and executed on a Dell desktop with an Intel Xeon X54723.00 GHz CPU and NIVIDA Titan X GPU. We used OpenCV to read the recorded videos and the results were visualized by the Visualization Toolkit (VTK). We collected ex- and in vivo stereo videos for the evaluation of our method, and details of the videos are provided in Tables 1 and 2, which includes the video length, number of frames, average tissue-camera distance, average camera motion speed, size of the tissue and the number of points of the reconstructed models.

Ex Vivo Experiments

TABLE 1

Parameters of Qualitative Experiments

|  | Ex vivo stomach | Ex vivo phantom | Ex vivo liver1 | Ex vivo liver2 | In vivo neuro-surgery (FIG. 22) | In vivo kidney (FIG. 23) | In vivo urethral (Third set of experiments) | In vivo spine (FIG. 24) | In vivo Hamlyn (Last set of experiments) |
|---|---|---|---|---|---|---|---|---|---|
| video length(s) | 19.5 | 48.3 | 15.5 | 28.7 | — | 3.4 | 12.4 | 6.1 | 35 |
| number of frames | 293 | 725 | 232 | 430 | 5 | 86 | 186 | 91 | 961 |
| resolution (pixels) | 960 × 540 | 960 × 540 | 960 × 540 | 960 × 540 | 720 × 480 | 1024 × 768 | 960 × 540 | 960 × 540 | 320 × 240 |
| average tissue-camera distance (mm) | 87.3 | 129 | 67.2 | 71.6 | 76.0 | 92.0 | 97.7 | 95.3 | 49.9 |
| average speed (mm/s) | 10.7 | 10.0 | 6.2 | 4.4 | — | 17.2 | 6.4 | 27.3 | 3.2 |
| bounding box length (mm) | 199 | 274 | 137 | 164 | 80 | 153 | 161 | 252 | 125 |
| number of model points (× $10^6$) | 2.1 | 2.6 | 1.9 | 1.8 | 0.8 | 1.1 | 1.2 | 2.2 | 0.2 |
| key frames threshold (Equation (44)): | 10.0 | 10.0 | 10.0 | 10.0 | 1e−6 | 5.0 | 10.0 | 10.0 | 3.0 |

TABLE 2

Parameters of Quantitative Experiments

Figure 21B:
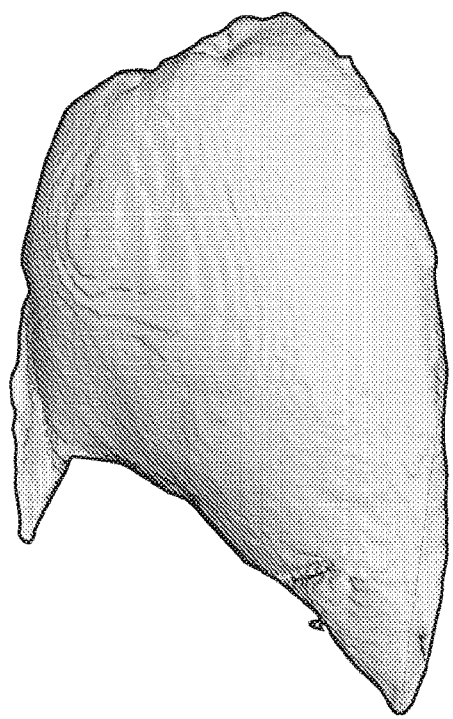
FIG. 21B is a computed tomography (CT) image segmentation of the procine liver of FIG. 21A.
Figure 21D:
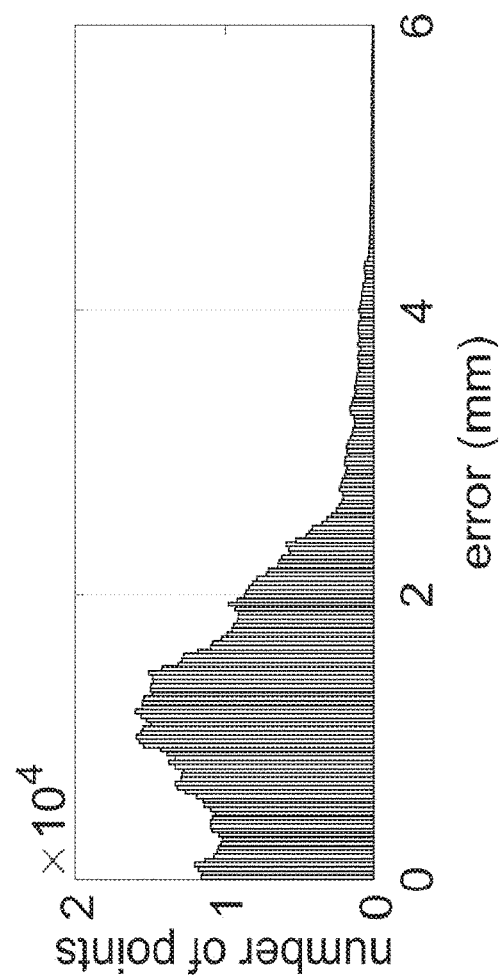
FIG. 21D is a histogram of errors between the 3D reconstruction in FIG. 21A and the CT image segmentation of FIG. 21B.
Figure 21A:
FIG. 21A is a 3D reconstruction of a porcine liver using a 3D reconstruction method.
Figure 21C:
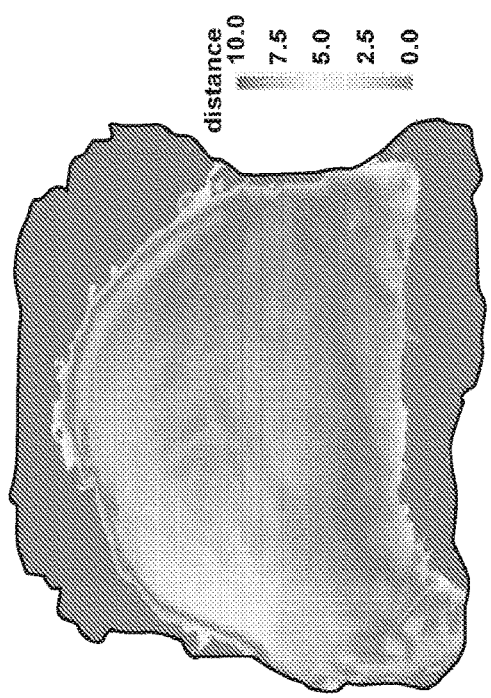
FIG. 21C is a distance map of the distance between the 3D reconstruction in FIG. 21A and the CT image segmentation of FIG. 21B.
Figure 21F:
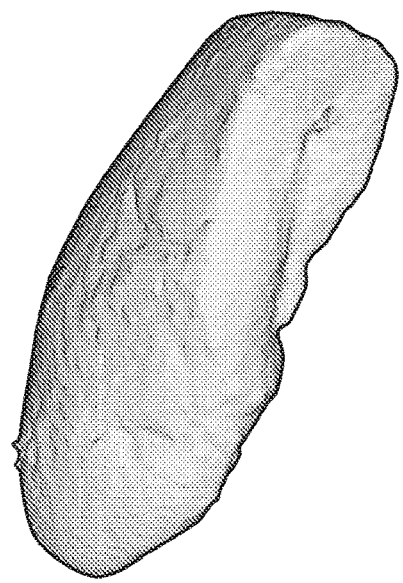
FIG. 21F is a CT image segmentation of the procine kidney of FIG. 21E.
Figure 21H:
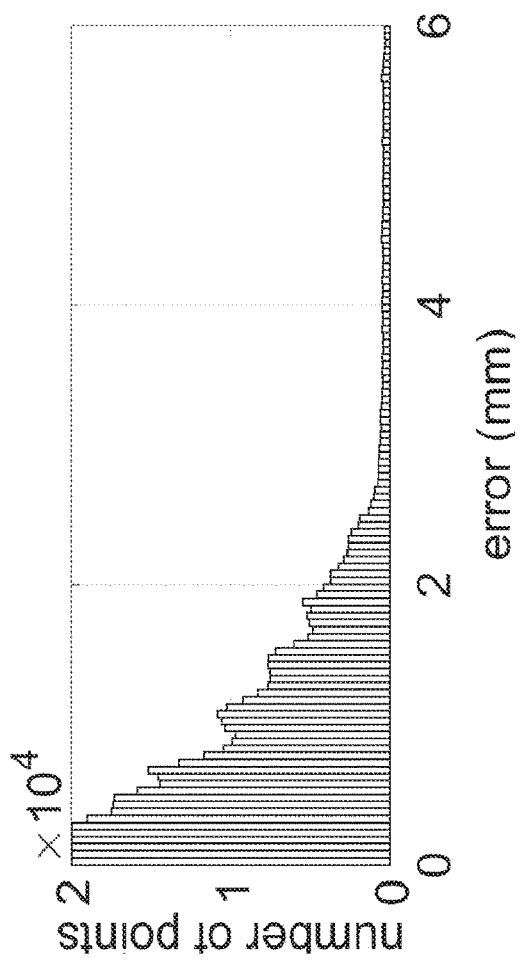
FIG. 21H is a histogram of errors between the 3D reconstruction in FIG. 21E and the CT image segmentation of FIG. 21F.
Figure 21E:
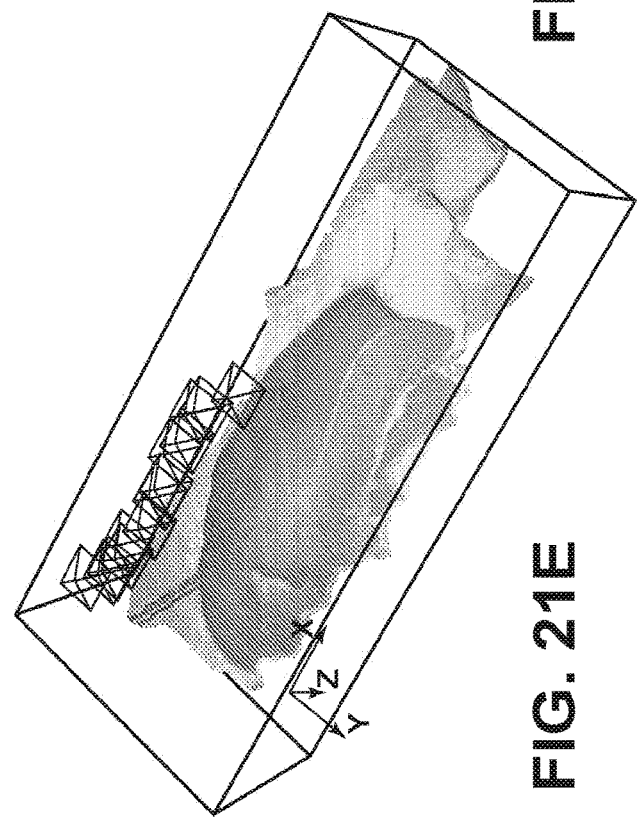
FIG. 21E is a 3D reconstruction of a porcine kidney using the 3D reconstruction method used in FIG. 21A.
Figure 21G:
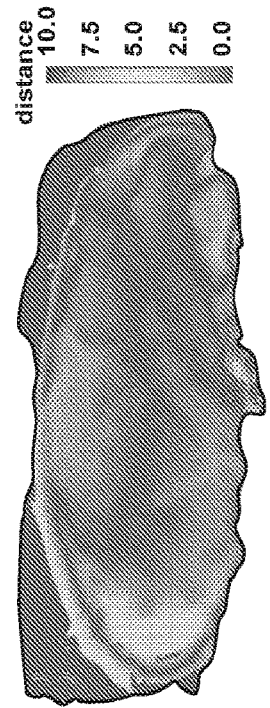
FIG. 21G is a distance map of the distance between the 3D reconstruction in FIG. 21E and the CT image segmentation of FIG. 21F.
Figure 21J:
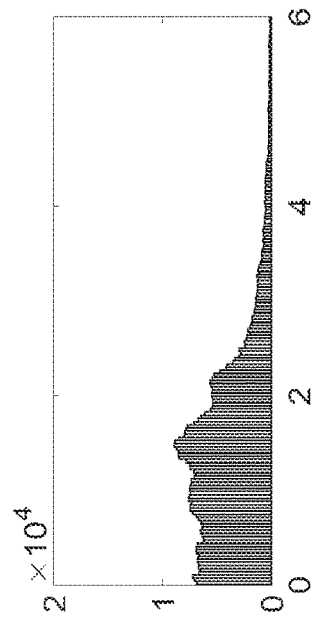
FIG. 21J is a histogram of errors between a 3D reconstruction and a CT image segmentation of a third porcine liver.
Figure 21L:
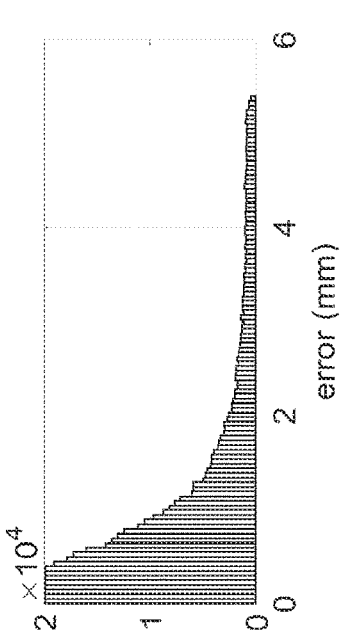
FIG. 21L is a histogram of errors between a 3D reconstruction and a CT image segmentation of a second porcine kidney.
Figure 21I:
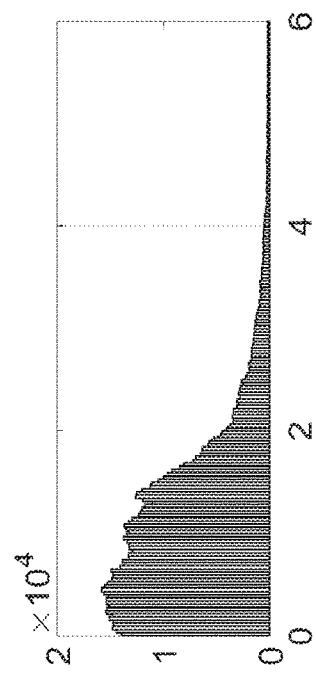
FIG. 21I is a histogram of errors between a 3D reconstruction and a CT image segmentation of a second porcine liver.
Figure 21K:
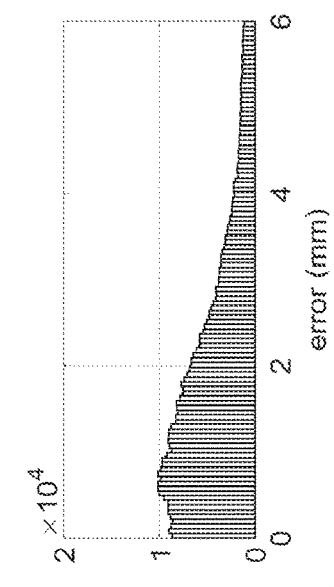
FIG. 21K is a histogram of errors between a 3D reconstruction and a CT image segmentation of a fourth porcine liver.
Figure 21M:
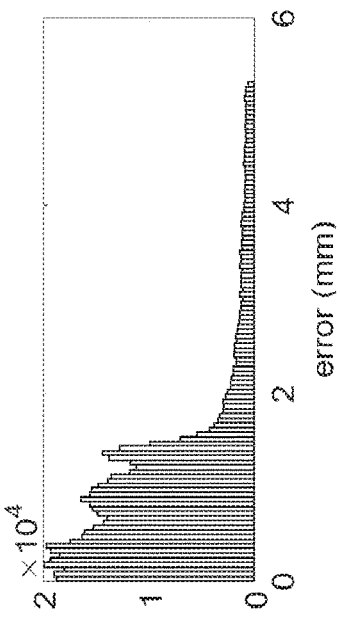
FIG. 21M is a histogram of errors between a 3D reconstruction and a CT image segmentation of a second porcine kidney.

|  | liver1 (FIG. 21A-D) | liver2 (FIG. 21I) | liver3 FIG. 21J) | liver4 FIG. 21K) | kidney1 (FIG. 21E-H) | kidney2 FIG. 21L) | kidney3 FIG. 21M) |
|---|---|---|---|---|---|---|---|
| video length(s) | 25.2 | 14.3 | 10.9 | 15.7 | 7.3 | 6.2 | 4.3 |
| number of frames | 378 | 215 | 164 | 236 | 109 | 93 | 64 |
| resolution (pixels) | 960 × 540 | 960 × 540 | 960 × 540 | 960 × 540 | 960 × 540 | 960 × 540 | 960 × 540 |
| average tissue-camera distance (mm) | 107.9 | 82.7 | 77.1 | 173.5 | 84.5 | 85.9 | 87.8 |
| average speed (mm/s) | 3.5 | 8.5 | 6.4 | 4.7 | 8.6 | 5.2 | 6.9 |
| bounding box length (mm) | 163 | 136 | 121 | 249 | 181 | 137 | 134 |

TABLE 2-continued

| | Parameters of Quantitative Experiments | | | | | | |
|---|---|---|---|---|---|---|---|
| | liver1 (FIG. 21A-D) | liver2 (FIG. 21I) | liver3 FIG. 21J) | liver4 FIG. 21K) | kidney1 (FIG. 21E-H) | kidney2 FIG. 21L) | kidney3 FIG. 21M) |
| number of model points (× $10^6$) | 1.2 | 1.2 | 0.9 | 0.7 | 0.7 | 0.7 | 0.7 |
| key frames threshold (Equation (44)): | 10.0 | 10.0 | 10.0 | 10.0 | 10.0 | 10.0 | 10.0 |
| RSME | 1.3 | 1.1 | 1.4 | 2.0 | 1.0 | 1.0 | 1.1 |

We first qualitatively tested 3D reconstruction method 500 on phantoms and ex vivo tissues, including porcine stomachs and livers. We used a KARL-STORZ stereo laparoscope (model number TipCam 26605AA) with a resolution of 960×540 to capture stereo videos and performed the 3D reconstruction method 500 on the videos. The candidate disparity values for performing ZNCC matching are between −20 and 80 pixels. Details of the videos are provided in Table 1. Since down-sampling is not included in the reconstruction process, the obtained 3D models have the same resolution as the input image, which usually include millions of points and are able to provide rich details of the surface texture. Our results qualitatively look promising and accurate. We also employed ORB-SLAM2 for comparison, which is one of the most famous open-source SLAM methods. In order to handle low texture, the key parameters of ORB-SLAM2 were set as follows: the number of feature points is 3000 per image, and the threshold for detecting FAST corner is 1. In testing, ORB-SLAM2 tracking failure occurred in cases certain cases (that the 3D reconstruction method 500 succeeded in) due to low texture.

In order to evaluate the quantified accuracy of the 3D reconstruction method 500, we used the CT imaging of tissues as the gold standard. In this experiment, CT scans of four ex-vivo porcine livers and three kidneys were obtained (Siemens Somatom, Erlangen Germany) with a 0.6 mm resolution at a hospital, and we used the 3D Slicer software to segment the tissue models from the CT images. We captured stereo videos of the tissues with the KARL-STORZ stereo laparoscope, the details of which are in Table 2. Surfaces of livers and kidneys are very smooth and have low textures, but the proposed method was still able to reconstruct the 3D models, as shown in FIG. 21. To quantify accuracy, we registered the 3D reconstructed model with the CT segmentation results by first manually selecting landmarks, such as tissue tips, edge points and other recognizable points, and then refining the registration with the ICP algorithm. As shown in Table 2, the root mean square errors (RMSE) with the liver cases are 1.3, 1.1, 1.4 and 2.0 mm respectively. The fourth liver case has a relatively larger error because we used an entire piece of liver and the video was captured at a larger camera-tissue distance. The results on porcine kidneys are shown in Table 2, the RMSE of which are 1.0, 1.0 and 1.1 mm respectively.

FIG. 21A shows a 3D reconstruction of a porcine liver using the 3D reconstruction method 500. FIG. 21B shows a CT image segmentation of the procine liver of FIG. 21A. FIG. 21C shows a distance map of the distance between the 3D reconstruction in FIG. 21A and the CT image segmentation of FIG. 21B. FIG. 21D shows a histogram of errors between the 3D reconstruction in FIG. 21A and the CT image segmentation of FIG. 21B.

FIG. 21E shows a 3D reconstruction of a porcine kidney using the 3D reconstruction method 500. FIG. 21F shows a CT image segmentation of the procine kidney of FIG. 21E. FIG. 21G shows a distance map of the distance between the 3D reconstruction in FIG. 21E and the CT image segmentation of FIG. 21F. FIG. 21H shows a histogram of errors between the 3D reconstruction in FIG. 21E and the CT image segmentation of FIG. 21F.

FIG. 21I shows a histogram of errors between a 3D reconstruction and a CT image segmentation of a second porcine liver (liver2 in Table 2). FIG. 21J shows a histogram of errors between a 3D reconstruction and a CT image segmentation of a third porcine liver (liver3 in Table 2). FIG. 21K shows a histogram of errors between a 3D reconstruction and a CT image segmentation of a fourth porcine liver (liver4 in Table 2). FIG. 21L shows a histogram of errors between a 3D reconstruction and a CT image segmentation of a second porcine kidney (kidney2 in Table 2). FIG. 21M shows a histogram of errors between a 3D reconstruction and a CT image segmentation of a second porcine kidney (kidney3 in Table 2).

The histograms shown in FIGS. 21A, 21E, and 21I-M show that most points have an error of less than 2 mm. It is worth noting that there are multiple sources of errors, including 3D reconstruction error, CT resolution error, CT segmentation error and registration error that contribute to the obtained RMSE in this experiment. In addition, because the livers and kidneys were placed on a textureless plastic sheet and part of the sheet were also included in the 3D reconstructed model, which is difficult to be totally removed, so the quantified error may also include a small amount of the background. Therefore, it is a reasonable assumption that the actual error of the 3D reconstruction method 500 is smaller than the reported RMSE.

In Vivo Experiments

To further evaluate the performance of the 3D reconstruction method 500 in real-world surgical scenarios, we obtained intraoperative videos from various stereo imaging modalities during surgeries performed in a hospital and online videos. The details of the videos are provided in Table 1. The videos were captured under an Institution Review Board approved protocol. Patient consent was waived since the analysis was performed retrospectively and no clinical decisions were affected.

For the first set of experiments, we obtained intraoperative stereo microscope images during a neurosurgery case. The dual channel output from a Carl-Zeiss microscope was captured using an Epiphan video capture card (DVI2PCI Duo) using the 3D Slicer software. Five image frames with resolution 720×480 with small overlap between the frames were used to create a high-resolution mosaic of the surgical cavity. The results of the stereo reconstruction and mosaicking algorithms are shown in FIG. 22.

Figures 22A, 22B, 22C:
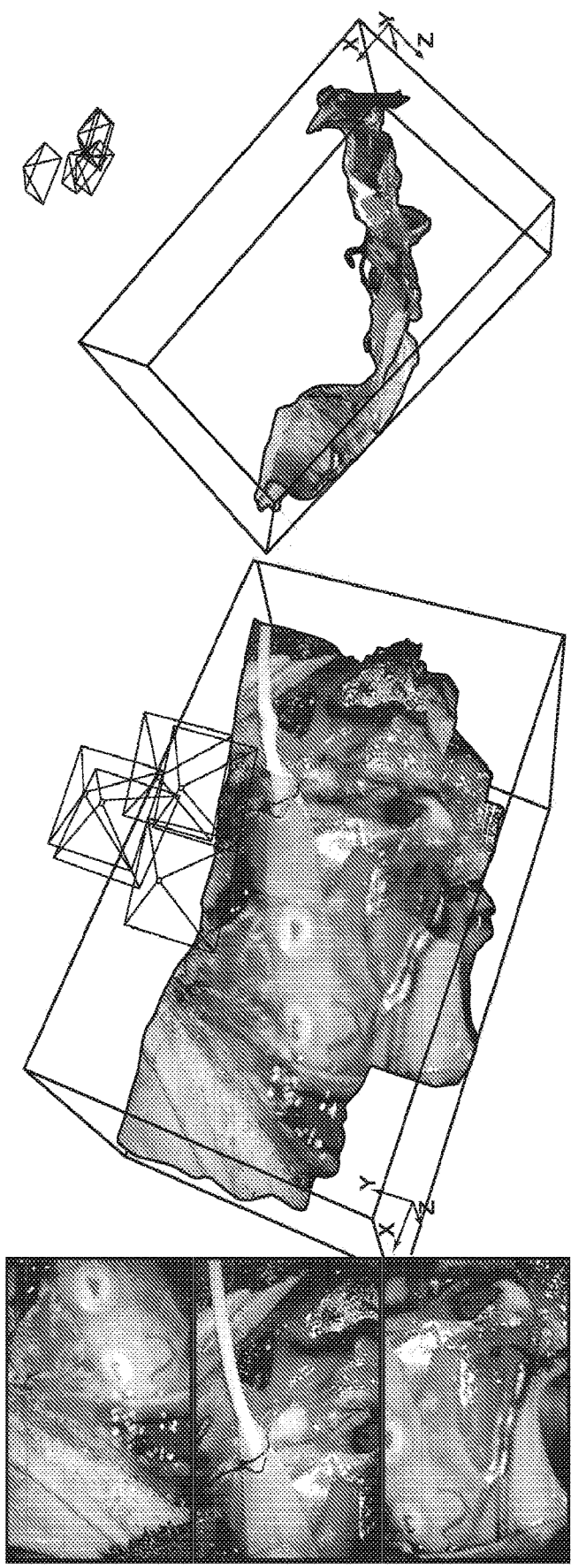
FIG. 22A is samples of 2D input images taken using a stereoscopic camera during neurosurgery, and only images from the left camera of the stereoscopic camera are shown.
FIG. 22B is reconstruction results of tissue surface viewed from a first angle.
FIG. 22C is the reconstruction results of the tissue surface viewed from a second angle.

FIG. 22A shows samples of 2D input images taken using a stereoscopic camera during neurosurgery, and only images from the left camera of the stereoscopic camera are shown. FIG. 22B shows reconstruction results of tissue surface viewed from a first angle. The reconstruction results were generated using video frames including the 2D input images shown in FIG. 22A. FIG. 22C shows the reconstruction results of the tissue surface viewed from a second angle.

Figures 23A, 23B, 23C, 23D:
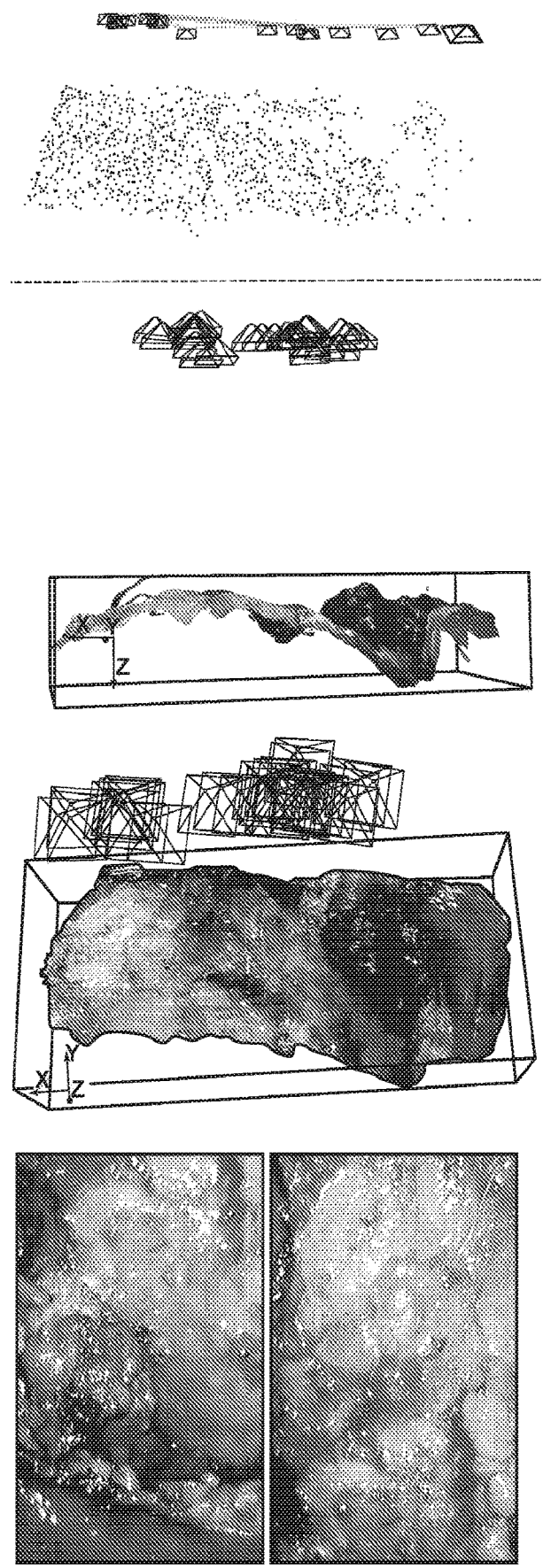
FIG. 23A is samples of 2D input images taken using a stereoscopic camera during neurosurgery, and only images from the left camera of the stereoscopic camera are shown.
FIG. 23B is reconstruction results of kidney surface viewed from a first angle. The reconstruction results were generated using video frames including the 2D input images shown in FIG. 23A.
FIG. 23C is the reconstruction results of kidney surface viewed from a second angle.
FIG. 23D is results of ORB-SLAM2 reconstruction of the kidney surface using the same 2D input images.
Figure 24D:
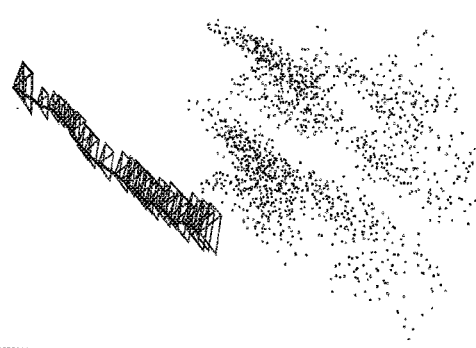
FIG. 24D shows results of ORB-SLAM2 reconstruction of the spinal surface and surrounding tissue surface using the same 2D input images.
Figure 24C:
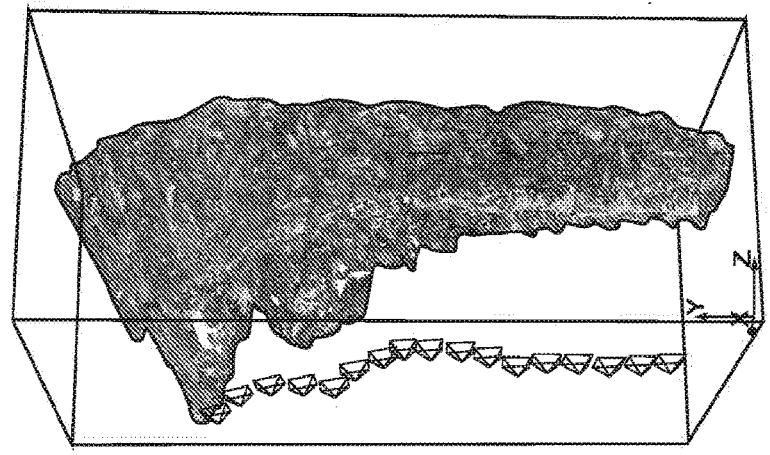
FIG. 24C shows the reconstruction results of the spinal surface and surrounding tissue surface viewed from a second angle.
Figure 24B:
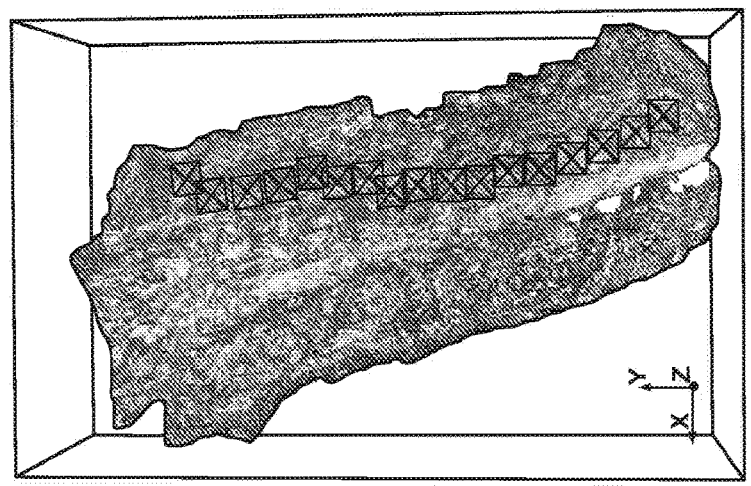
FIG. 24B shows reconstruction results of spinal surface and surrounding tissue surface viewed from a first angle. The reconstruction results were generated using video frames including the 2D input images shown in FIG. 24A.
Figure 24A:
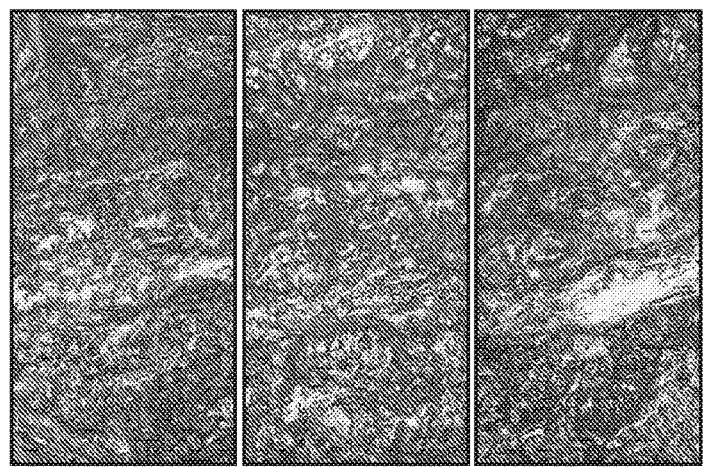
FIG. 24A shows samples of input left camera images from the stereo laparoscope.

FIG. 23 shows results of experiments on stereo laparoscopy videos captured during a robotic surgery of a kidney. Due to respiration, the camera motion with respect to the kidney is more complex. The surface of the kidney and a tumor are shown in the images. FIG. 23 A shows samples of 2D input images taken using a stereoscopic camera during neurosurgery, and only images from the left camera of the stereoscopic camera are shown. FIG. 23B shows reconstruction results of kidney surface viewed from a first angle. The reconstruction results were generated using video frames including the 2D input images shown in FIG. 23A. FIG. 23C shows the reconstruction results of kidney surface viewed from a second angle. FIG. 23D shows results of ORB-SLAM2 reconstruction of the kidney surface using the same 2D input images.

In this experiment, we simply set the pose threshold to determine key frames to a small number hence all five images were used as key frames. Such a high-resolution mosaicking of the neurosurgery cavity could conceivably be used to register the intraoperative or diagnostic MRI to the mosaicked stereo reconstruction of the surgical cavity to identify remnant brain tumor during surgery. Due to the too small number of images, we did not run ORB-SLAM2 for this case.

For the next set of experiments, we obtained high resolution stereo laparoscopy images of the kidney during a robot-assisted partial nephrectomy case. The video was obtained from the dual channel DVI output of the master console of the Intuitive da Vinci Xi robot. The video has the resolution of 1024×768, and was captured using two Epiphan video capture cards (DVI2PCI Duo) and a simple video capture program implemented using OpenCV. Prior to tumor resection, the surgeon scanned the exposed kidney surface using a stereo laparoscope. The 3D reconstructed model of the kidney surface and the tumor is shown in FIG. 23. This model could further be registered to the diagnostic CT or MRI to plan the extent of surgical resection intraoperatively. This experiments also showed that the 3D reconstruction method 500 can handle non-rigid motion, such as tissue motion caused by respiration, which is because respiration often cause the entire tissue to move but the deformation is relatively minimal. Since the time to scan the tissue surface is short, the tissue motion may not significant.

In the third set of experiments, we obtained intraoperative stereo laparoscopy images from a uretheroplasty procedure. Prior to resecting the urethral constriction, the urethra was exposed to identify the extent of the constriction. Thereafter, the authors scanned the exposed surgical area using a stereo laparoscope (Karl Storz Inc., model TipCam 26605AA) by moving the laparoscope slowly along the urethra. The interlaced video was captured and recorded using a video capture program in OpenCV. The surface mosaicking algorithms of the exposed urethra resulted in a high-resolution 3D mosaicked surface model of the urethra and the surrounding structures.

The fourth set of experiments were conducted with the same stereo laparoscope and the data was collected during a spine surgery, as shown in FIG. 24. FIG. 24A shows samples of input left camera images from the stereo laparoscope. FIG. 24B shows reconstruction results of spinal surface and surrounding tissue surface viewed from a first angle. The reconstruction results were generated using video frames including the 2D input images shown in FIG. 24A. FIG. 24C shows the reconstruction results of the spinal surface and surrounding tissue surface viewed from a second angle. FIG. 24D shows results of ORB-SLAM2 reconstruction of the spinal surface and surrounding tissue surface using the same 2D input images. The ORB-SLAM2 method failed to track the camera motion during the scan during the spinal surgery.

The spine bone was scanned by the Karl Storz stereo laparoscope after it was exposed. The estimated camera trajectories are smooth, which qualitatively prove that the 3D reconstruction method 500 is accurate.

The last in-vivo experiment was conducted on the Hamlyn data (available at http://hamlyn.doc.ic.ac.uk/vision/data/Dataset1/stereo.avi), which was captured within a porcine abdomen by using a stereo laparoscope. The length of this video is longer (≈35 s) than other videos, and the camera trajectory was shown to be qualitatively smooth, demonstrating that the 3D reconstruction method 500 is able to work on such relatively long videos.

We also tested ORB-SLAM2 on the collected in vivo data, which performed well on most cases because the texture is generally richer than the ex vivo data. However, in the spine experiment we observed that ORB-SLAM2 failed to track the camera motion during the scan (see FIG. 24).

Experiments with in-vivo data demonstrated that the 3D reconstruction method 500 can be applied to stereo optical videos obtained from different types of imaging modalities, and has potential for the 3D reconstruction of different types of tissues in varying lighting and surgical conditions. The reconstructed surface could be used for further registration to diagnostic or intraprocedural volumetric CT/MRI imaging.

Runtime

We report the average runtime of the main steps of the proposed 3D reconstruction method in Table 3, which is the average results of 1,000 key frames on 960×540 laparoscopy videos. The average computational time to process a key frame is 76.3 ms, which suggests that the proposed method is real-time.

TABLE 3

| Average Runtime of 3D Reconstruction(ms) | |
| --- | --- |
| video reading | 12.7 |
| stereo matching | 15.9 |
| ORB matching and histogram voting | 15.2 |
| DynamicR1PPnP | 6.1 |
| Refinement | 24.6 |
| TSDF | 2.2 |
| Total | 76.3 |

In this disclosure, we have proposed a series of algorithms to solve the problem of tissue surface reconstruction, and mainly addressed the difficulties caused by low texture. The main novelties of this disclosure are as follows: (1) We have proposed effective post-processing steps for the local stereo matching method to enlarge the radius of constraint, and these steps are appropriate for GPU computation. (2) We have combined a histogram voting-based inliers pre-selection method and a novel DynamicR1PPnP algorithm that is robust to feature matching outliers to handle the camera motion tracking problem in the SLAM system. Traditional SLAM systems, such as ORB-SLAM, usually utilize RANSAC+P3P methods for camera motion tracking, which cannot work robustly when the number of inliers is too small. The methods proposed in this disclosure can greatly improve the robustness of the SLAM system. Experimental results on ex- and in vivo videos captured using different types of imaging modalities have demonstrated the feasibility of our methods, and the obtained models have high quality textures and the same resolution as the input videos. We have also introduced the CUDA implementation details to accelerate the computation with the GPU and enable real-time performance.

As further extensions of the above-describe concepts, an approach is introduced to recover the deformation of tissue surface from stereo optical videos in real-time.

In recent years, several groups have investigated methods to recover tissue deformation from optical videos, and most methods are based on the minimization of non-rigid matching and smoothing costs. For example, one group proposed a monocular vision-based method that first generated the tissue template and then estimated the template deformation by matching the texture and boundaries with a non-rigid iterative closet points (ICP) method. In this method, the non-rigid ICP-based boundary matching algorithm significantly improves the accuracy. However, during surgery, only a small area of the target tissue may be exposed and the boundaries are often invisible, which makes it difficult to match the template. Object deformation recovery in the computer vision field is also a suitable approach to recover tissue deformation. For example some have proposed to generate the template from an RGB-D camera and then track the deformation by minimizing non-rigid ICP, color and smoothing costs. Others have developed a novel deformation recovery method that does not require the initial template and uses sparse control points to represent the deformation. Forward and backward $L_0$ regularization has been used to refine the deformation recovery results.

To date, most deformation recovery methods are based on the non-rigid ICP alignment to obtain matching information between the template and the current input, such as monocular/stereo videos or 3D point clouds from RGB-D sensors. However, non-rigid ICP suffers from a drawback that it cannot track fast tissue deformation and camera motion, and obtain accurate alignment in the tangential directions on smooth tissue surfaces. During surgery, the endo/laparoscope may move fast or even temporally out of the patient for cleaning, which makes non-rigid ICP difficult to track the tissue. In addition, smoke and blood during the surgery may cause significant occlusion and interfere with the tracking process. Hence, the ability to match the template and the input video when non-rigid deformation exists is essential for intraoperative use of deformation recovery methods.

A natural idea to obtain additional information is to match the feature points between the template and the input video. Among many types of feature descriptors, ORB has been widely used in real-time applications due to its efficiency. To handle feature matching outliers, RANSAC-based methods have proven effective in rigid scenarios but are difficult to handle non-rigid deformation. Another common method to address outliers is to apply robust kernels to the cost function, which cannot handle fast motion. This portion of the disclosure presents a novel method that combines 1-point-RANSAC and reweighting methods to handle matching outliers in non-rigid scenarios. In addition, we propose a novel as-rigid-as-possible (ARAP) method based on dense connections to achieve better smoothing performance with limited number of iterations.

Method

In this portion of the disclosure, we propose an approach to estimate the deformation of tissue surface from stereo videos in real-time, which is capable of handling occlusion, smooth surface and fast deformation. The method (which will be described in conjunction with FIG. 25) can use a stereo matching method such as the GPU-based stereo matching method 250 described above in conjunction with FIG. CCC 1A to extract depth information from stereo video frames and generate the tissue template, and then estimate the deformation of the obtained template by minimizing ICP, ORB feature matching and as-rigid-as-possible (ARAP) costs. The main novelties are twofold: (1) Due to non-rigid deformation, feature matching outliers are difficult to be removed by traditional RANSAC methods; therefore we propose a novel 1-point RANSAC and reweighting method to preselect matching inliers, which handles smooth surfaces and fast deformations. (2) We propose a novel ARAP cost function based on dense connections between the control points to achieve better smoothing performance with limited number of iterations.

In our system, the initial template of the tissue surface is generated by the stereo matching method 250, then we track the deformation of the template by representing the non-rigid deformation with sparse control points on the template, and estimating the parameters of the control points to make the deformed template match the output of the GPU-based stereo matching method. The algorithms are parallelized and run on the GPU. Similar to DynamicFusion, we employ dual-quaternion to represent deformation and each control point i is assigned a dual-quaternion $W_i^t$ to represent its warp function at time t, and the template points are deformed according to the interpolation of neighboring control points. Then, the deformation recovery problem is to estimate $W_i^t$, i=1, ..., N, and we use the Levenberg-Marquardt algorithm to minimize the following cost function $$f_{Total}(W_i^t) = f_{ICP} + w_{ORB} f_{ORB} + w_{ARAP} f_{ARAP}, \quad (50)$$

where $f_{ICP}$ and $f_{ORB}$ are based on non-rigid ICP and ORB matches between the template and the current stereo matching results respectively. The as-rigid-as-possible (ARAP) cost $f_{ARAP}$ smoothes the estimated warp functions $W_i^t$, which is especially important for the estimation of occluded areas. $w_{ORB}$ and $W_{ARAP}$ are user defined weights. In our experiments, we use $w_{ORB}$=10.0 and $W_{ARAP}$ is dynamically adjusted due to the varying number of valid points in $f_{ICP}$ and ORB matching inliers in $f_{ORB}$. We sum up the related weights of ICP and ORB terms for each $W_i^t$, and scale up or down $W_{ARAP}$ accordingly.

A GPU-based parallel Levenberg-Marquardt (LM) algorithm was developed to minimize the cost Equation (50). We update each $W_i^t$ independently in the LM iterations. For the computation of the Jacobian matrix J related to each $W_i^t$, multiple parallel GPU threads are launched to compute rows of J, then we perform Cholesky decomposition to update $W_i^t$, i=1, ..., N.

The non-rigid ICP term $f_{ICP}$ is determined by the distances between the deformed template and the stereo matching results. The Tukey's penalty function is employed to handle outliers. We have developed a rasterization process that re-projects the template points to the imaging plane to build correspondences between template points and the stereo matching results, which is parallelized to each template point and runs on the GPU. This rasterization step is faster than kd-tree-based closest points search in the 3D space. Only the distance component in the normal directions are considered, which avoids the problem that non-rigid ICP is inaccurate in the tangential directions when aligning smooth surfaces.

ORB Feature Matching and Inliers Pre-Selection

Figure 26B:
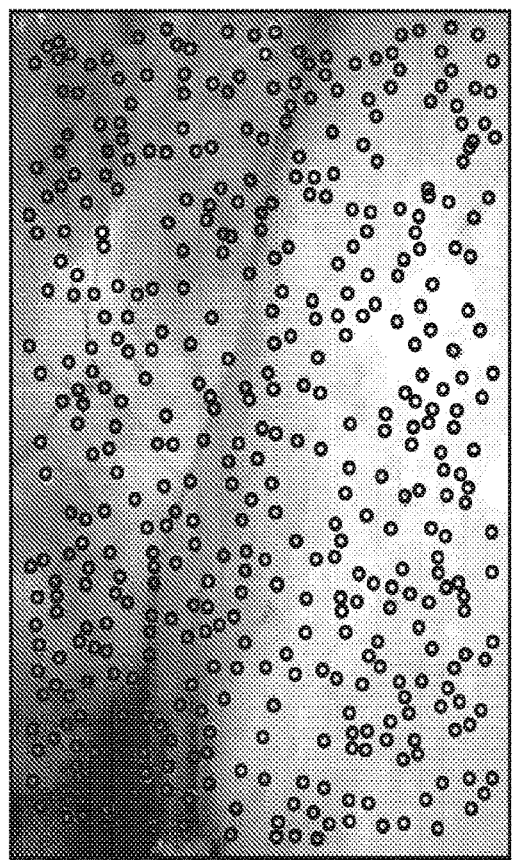
FIG. 26B is ORB feature detection results on laparoscopy images captured during a lung surgery using a novel method that can be included in a process 600 that will be described below.
Figure 26A:
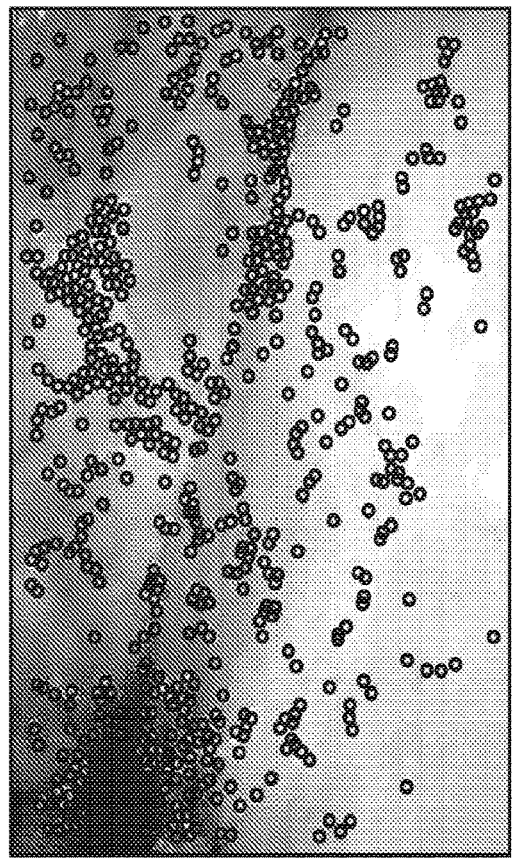
FIG. 26A is Oriented FAST and rotated BRIEF (ORB) feature detection results on laparoscopy images captured during a lung surgery using OpenCV.

As shown in FIG. 26A, standard ORB feature detection concentrates on rich texture areas, which may lead to the lack of matching information at low texture areas. Hence, we first develop a method to detect uniform ORB features to improve the accuracy of deformation recovery, which uses GPU to detect FAST corners and suppresses those if a neighboring pixel has larger corner response in parallel. Then, the ORB features of the initial template are matched to the live video frames. Two corresponding 3D point clouds are obtained, which may include incorrect matches.

Figure 26D:
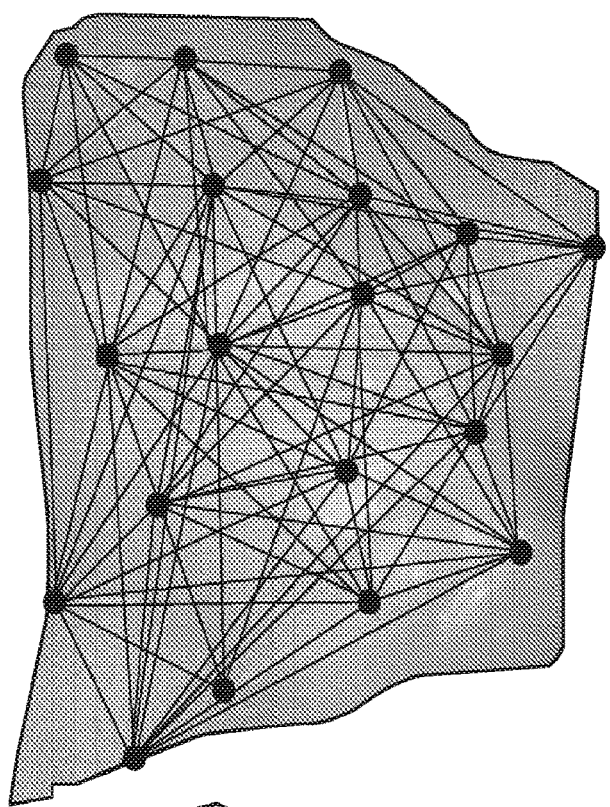
FIG. 26D is dense connections between control points with a silicon heart phantom.
Figure 26C:
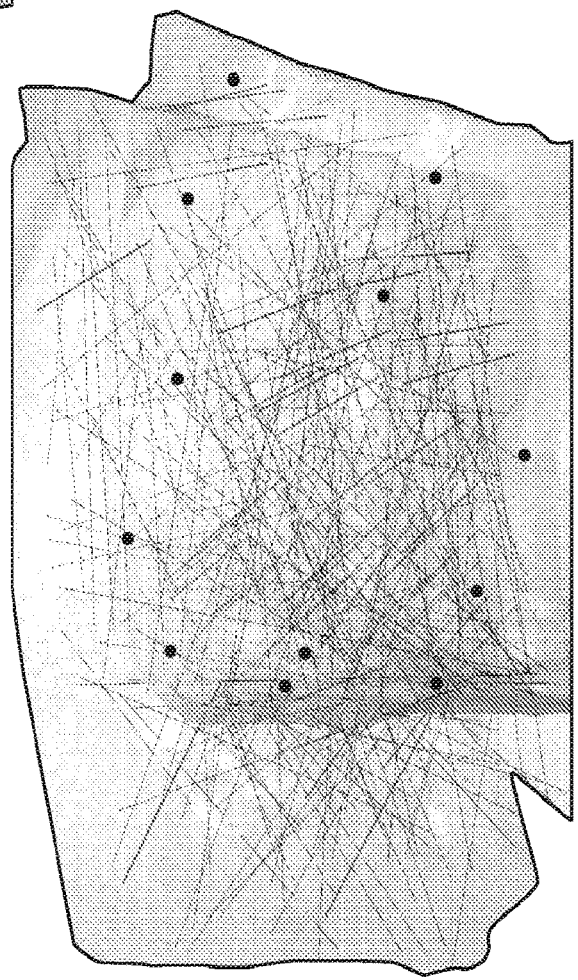
FIG. 26C is matching inliers pre-selection results with a deforming phantom including lines representing selected inliers and outliers.

Since at least three matches are needed to determine the rigid relative pose between two 3D point clouds, traditional RANSAC methods only work when the three matches are all inliers and have similar deformation. Another common method to handle outliers is to apply robust kernels to the cost function, which is effective but cannot handle fast camera motion or tissue deformation. Under a reasonable assumption that local deformations at small areas of the tissue surface are approximate to rigid transforms, we propose a novel 1-point-RANSAC and reweighting method to pre-select potential matching inliers, as shown in FIG. 26C. Denoting the two sets of corresponding 3D ORB features as $o_k^1$ and $o_k^2$, $k=1, \ldots, N$, a random match $k_0$ is selected as the reference, and rectify the coordinates with respect to $k_0$ by $$S_{k0}^l = [(o_1^l - o_{k0}^l, \ldots, o_N^l - o_{k0}^l)]_{3 \times N}, l=1,2. \quad (51)$$

For a reference $k_0$, we denote the local rigid transform as $o_{k0}^2 = R o_{k0}^1 + T$, where $R \in SO(3)$ is the rotation matrix and T is the translation vector. Rigid transform for a neighboring match inlier k should satisfy $$S_{k0}^2(k) \approx R S_{k0}^1(k), \quad (52)$$

where $S_{k0}(k)$ is the kth column of $S_{k0}$, and R can be obtained from matches that satisfy Equation (52). We propose a reweighting method to eliminate the impacts of other matches, that is $$d_k = \|S_{k0}^2(k) - R S_{k0}^1(k)\|, w_k = \min(H/d_k, 1), \quad (53)$$

where $d_k$ is the distance related to the kth match. $W_k$ is the weight of the kth ORB match and if the kth match is either an outlier, or an inlier that does not satisfy Equation (52), $w_k$ is small. H is a predefined threshold. With a selected reference $k_0$, we alternatively update R from weighted $S_{k0}^1$ and $S_{k0}^2$, and update $w_k$ according to Equation (53). In experiments we perform 10 iterations with each $k_0$. A small sum of $w_k$ suggests that few matches satisfy Equation (52) and $k_0$ may be an outlier, and we omit the results with reference $k_0$. In our experiments, we randomly select 30 different matches as the reference $k_0$.

FIG. 26A shows ORB feature detection results on laparoscopy images captured during a lung surgery using OpenCV. FIG. 26B shows ORB feature detection results on laparoscopy images captured during a lung surgery using a novel method that can be included in a process 600 that will be described below. FIG. 26C shows matching inliers pre-selection results with a deforming phantom including lines representing selected inliers and outliers. FIG. 26D shows dense connections between control points with a silicon heart phantom.

We first apply this 1-point-RANSAC+reweighting method to assign weights to ORB matches, the results of which will be used in the subsequent LM algorithm to minimize term $f_{ORB}$ in Equation (50). It should be clarified that we are not implying that this 1-point-RANSAC+reweighting method is able to find all inliers. To take into account all inliers, in the LM algorithm we assign the pre-selected matches the same weight as $w_k$, and assign other ORB matches weight according to $w_k = -1/(5H)d_k+1$, $w_k \in [0,1]$.

As-Rigid-As-Possible Smoothing

Traditional ARAP methods are based on sparse connections, such as triangular meshes. This type of connection is too sparse to propagate the smoothing impact fast enough, and in practice we found that it cannot perform well with the limited number of iterations in the LM algorithm. Hence, we propose to use dense connections as shown in FIG. 26D. The weights of connections in traditional ARAP methods are sensitive and need to be specifically designed based on the angles of the triangular mesh, hence the ARAP cost function has to be redesigned to handle the dense connections as follows:

$$f_{ARAP} = \Sigma_{i1,i2} w_{i1,i2}(f_{length,i1i2} + W_{angle} f_{angle,i1i2} + w_{rotation} f_{rotation,i1i2}) \quad (54)$$

where $i_1$ and $i_2$ are two control points. $w_{i1,i2}$ is the weight of connection between $i_1$ and $i_2$, and a smaller distance between points $i_1$ and $i_2$ at time 0 suggests larger $w_{i1,i2}$. We use $w_{angle}=20.0$ and $w_{rotation}=100.0$.

For control points $i_1$ and $i_2$, $$f_{length,i1i2} = (\|p_{i2}^t - P_{i1}^t\| - \|p_{i2}^0 - P_{i1}^0\|)^2$$

$$f_{angle,i1i2} = a\cos(W_{i1}^t(p_{i2}^0) - p_{i1}^t, p_{i2}^t - P_{i1}^t)$$

$$f_{rotation,i1i2} = \|W_{i1}^t(1,2,3,4) - W_{i2}^t(1,2,3,4)\|^2 \quad (55)$$

where $p_i^t$ is the coordinate of point i at time t. $f_{angle,i1i2}$ equals to the angle between the normalized vectors $W_{i1}^t(p_{i2}^0) - p_{i1}^t$ and $p_{i2}^t - p_{i1}^t$, where $W_{i1}^t(p_{i2}^0)$ suggest to apply $W_{i1}^t$ to $p_{i2}^0$. $f_{rotation,i1i2}$ is introduced because $W_i^t$ has 6-DoFs, which is determined by the differences between the first four components of dual-quaternion $W_{i1}^t$ and $W_{i2}^t$.

Experiments

FIG. 27 shows various qualitative experiments. First row: input video frames. Second row: the deformed template and the control points (dots).

Figure 27A:
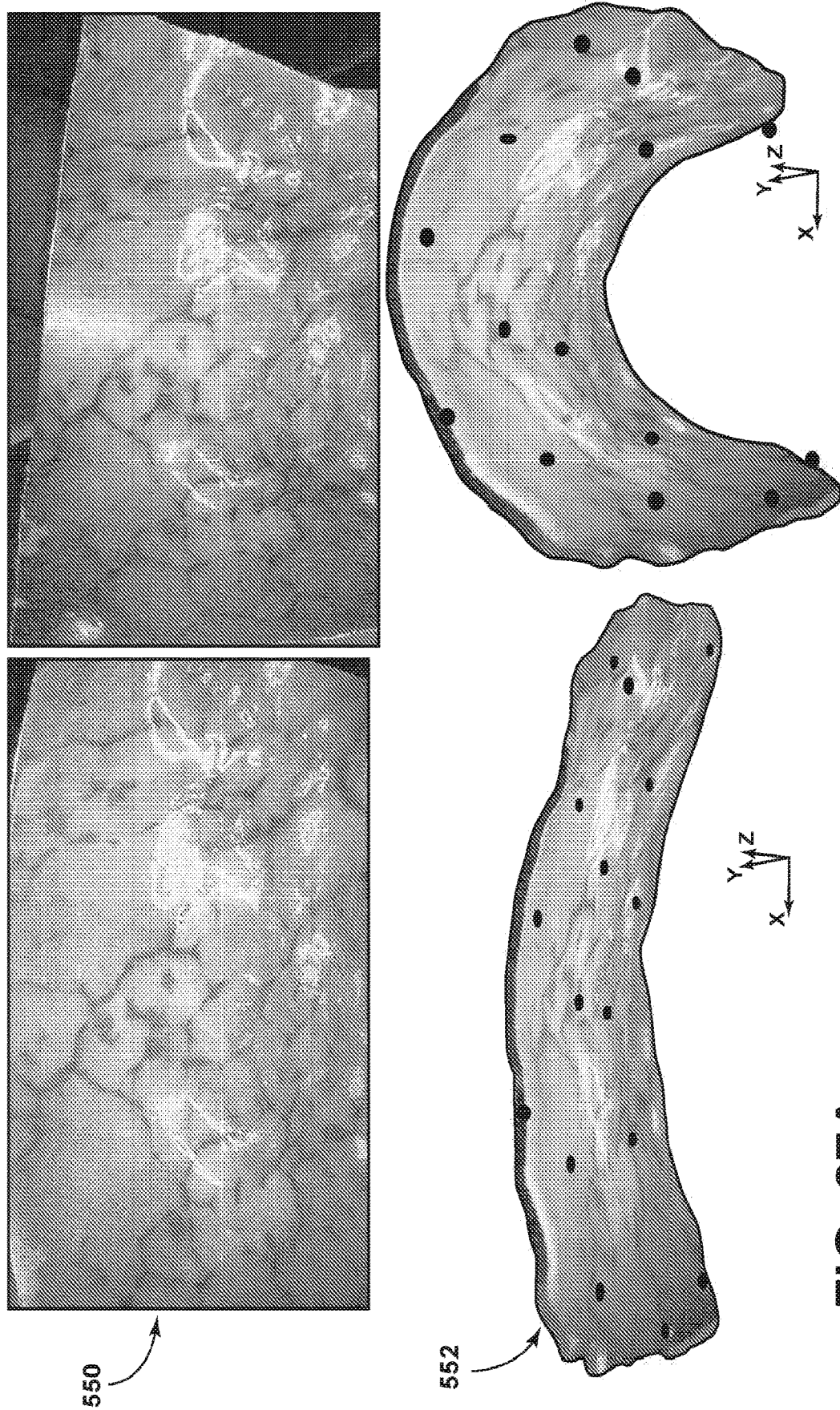
FIG. 27A is a set of input video frames of a phantom along with a corresponding set of deformed templates including dots representing control points.
Figure 27B:
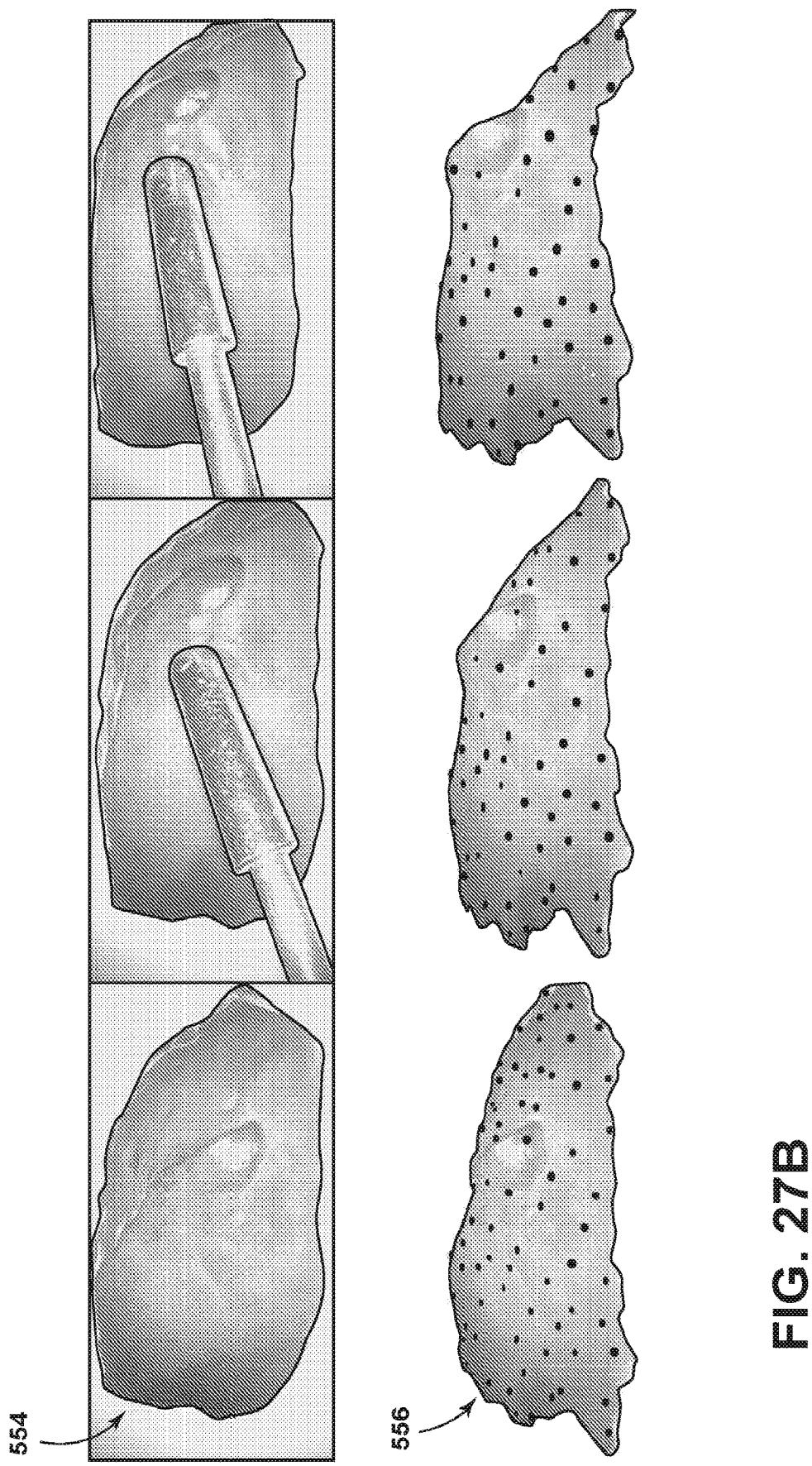
FIG. 27B is a set of input video frames of an ex vivo porcine liver along with a corresponding set of deformed templates including dots representing control points.
Figure 27C:
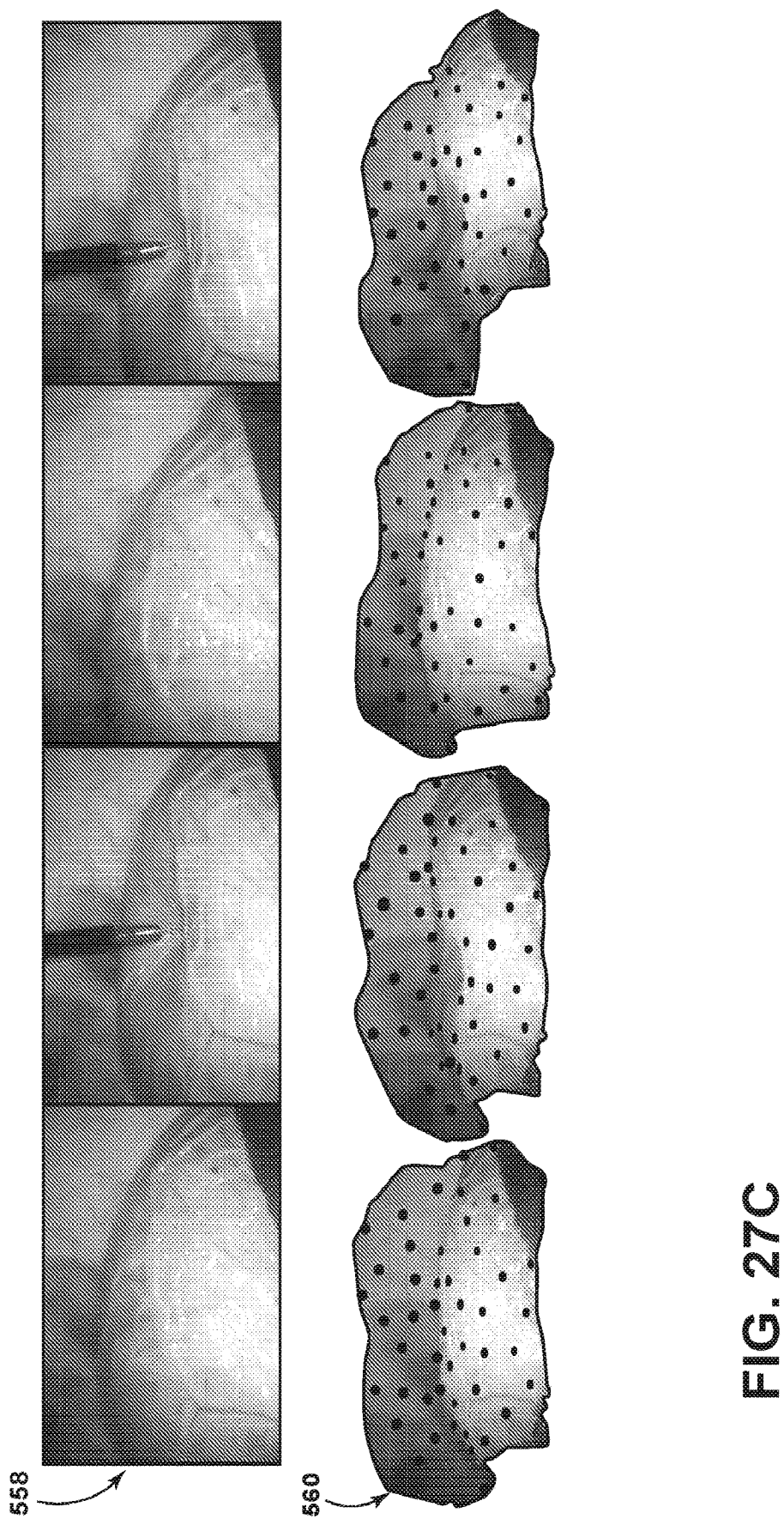
FIG. 27C is a set of input video frames of Hamlyn in vivo data with deformation caused by instrument interaction along with a corresponding set of deformed templates including dots representing control points.

FIG. 27A shows a set 550 of input video frames of a phantom along with a corresponding set 552 of deformed templates including dots representing control points. FIG. 27B shows a set 554 of input video frames of an ex vivo porcine liver along with a corresponding set 556 of deformed templates including dots representing control points. FIG. 27C shows a set 558 of input video frames of Hamlyn in vivo data with deformation caused by instrument interaction along with a corresponding set 560 of deformed templates including dots representing control points. FIG. 27D shows a set 562 of input video frames of Hamlyn in vivo data with respiration and heartbeat along with a corresponding set 564 of deformed templates including dots representing control points. FIG. 27E shows a set 566 of input video frames of in vivo kidney data with deformation caused by respiration along with a corresponding set 568 of deformed templates including dots representing control points.

Algorithms were implemented with CUDA C++ running on a desktop with Intel Xeon 3.0 GHz CPU and NVIDIA Titan X GPU. We first conducted qualitative experiments on ex- and in vivo data. As shown in FIG. 3A, we deformed a smooth phantom with lung surface texture and captured 960×540 stereo videos with a KARL STORZ stereo laparoscope. We removed intermediate video frames between the two frames in FIG. 3A to simulate fast deformation, and the process 600 is capable of tracking the large deformation. The second experiment was conducted with ex vivo porcine liver as shown in FIG. 27B. The deformation was caused by instrument interaction, and the process 600 is able to handle instrument occlusion. For the in vivo experiments shown in FIG. 27C-E, we used both the Hamlyn data and our data, in which the videos have camera motion and tissue deformation. We generated the tissue template before instrument interaction and then track the deformation of the template. The algorithm detected key inlier ORB features on the reconstructed surface and tracked these template features robustly in spite of respiratory and pulsatile motions, and instrument occlusions. These results highlight the robustness of tracking in spite of physiological motions and varying illumination.

Figure 28A:
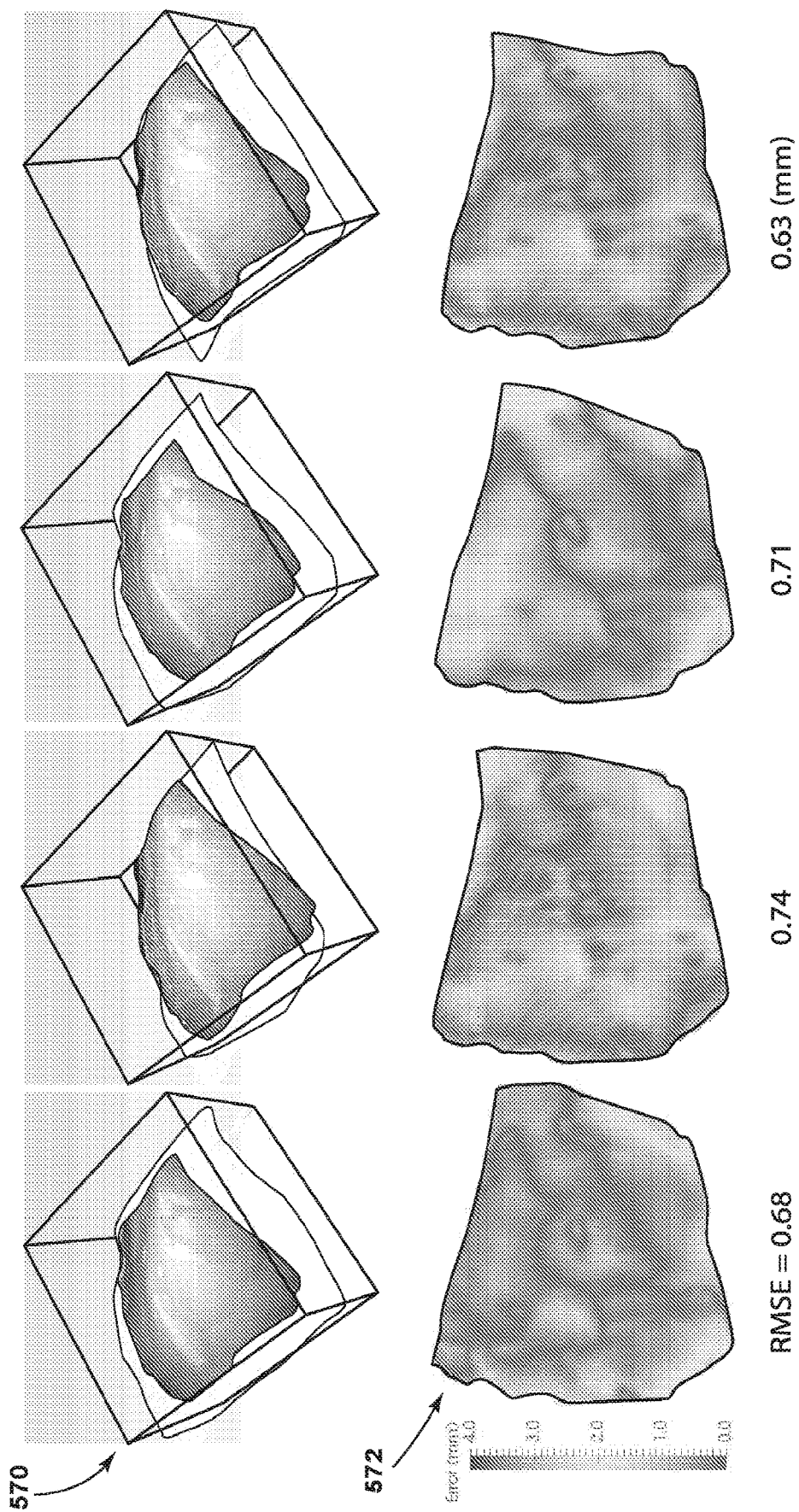
FIG. 28A is a set of deformed templates and a corresponding set of distance maps showing the distance between the deformed templates and a ground truth.
Figure 28B:
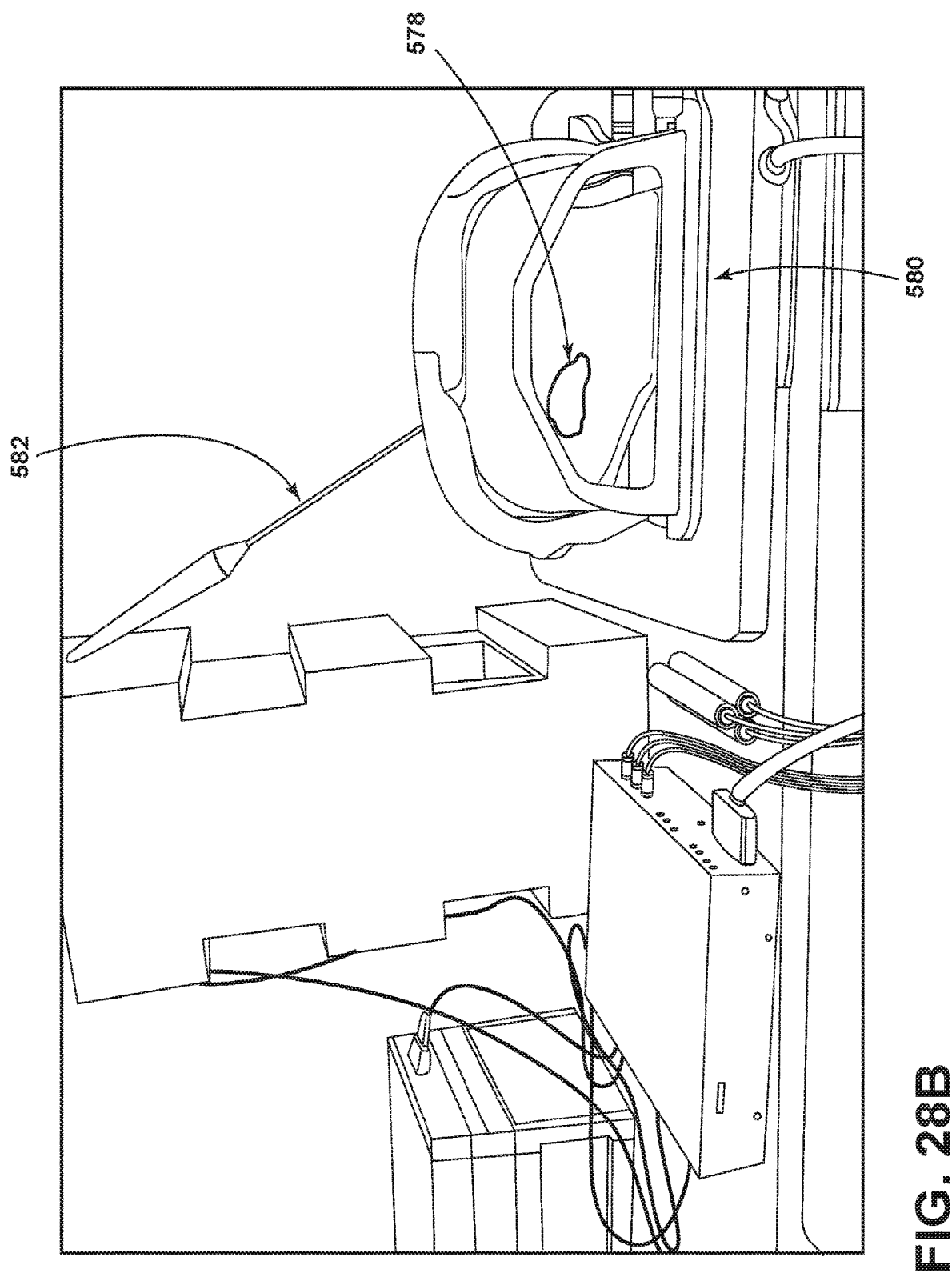
FIG. 28B is an illustration of hardware including an electromagnetic (EM) tracking system used in another experiment to generate the data in FIGS. 28C-D.
Figure 28C:
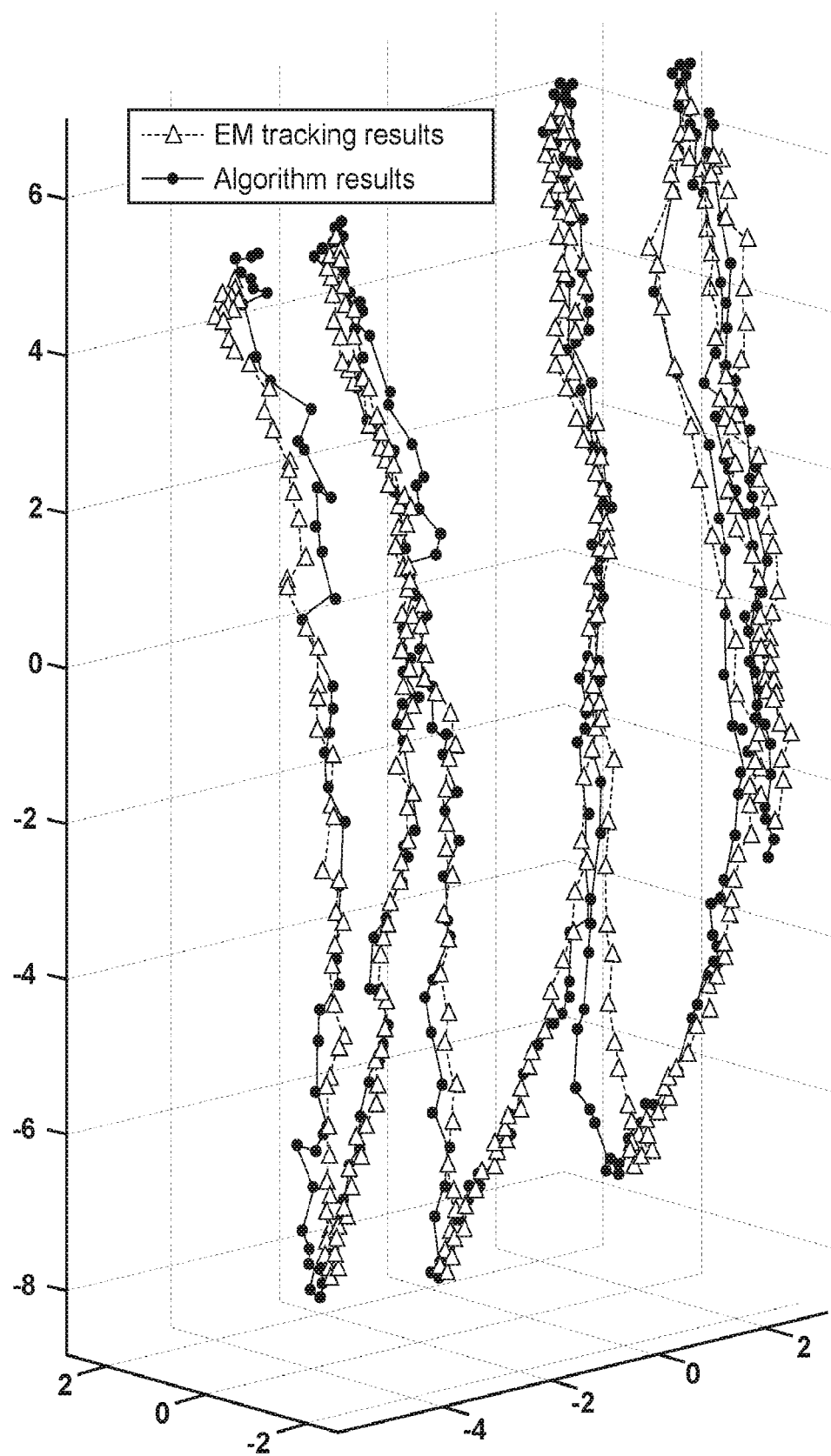
FIG. 28C shows 3D trajectories of the ground truth (EM tracking system) and the deformed templates.
Figure 28D:
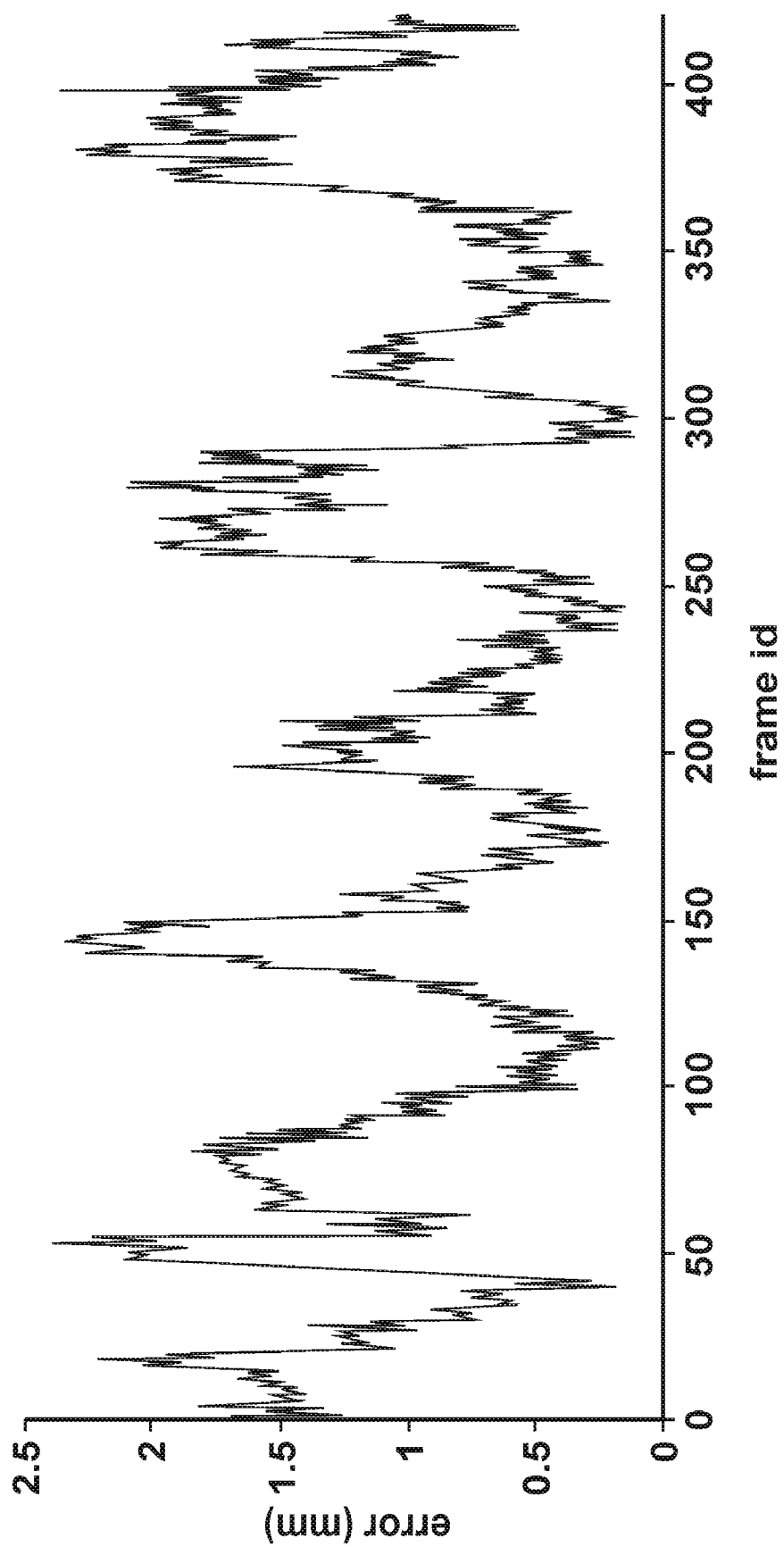
FIG. 28D shows error in millimeters by frame for the experiment in FIG. 28B.

We conducted two quantitative experiments. FIG. 28 shows quantitative experiments. FIG. 28A shows a set 570 of deformed templates and a corresponding set 572 of distance maps showing the distance between the deformed templates and a ground truth. FIG. 28B shows a porcine liver 578 and hardware including an electromagnetic (EM) tracking system 580 and a stereo laparoscope 582 used in another experiment to generate the data in FIGS. 28C-D. FIG. 28C shows 3D trajectories of the ground truth (EM tracking system) and the process 600 (algorithm results). FIG. 28D shows error in millimeters by frame.

The first experiment was conducted on Hamlyn data as shown in FIG. 28A. The Hamlyn data consists of stereo video images of a silicon phantom simulating heartbeat motion and corresponding ground truth was obtained using CT scan. The template was generated from the first video frame. Results show an RMSE of less than 1 mm and the average runtime of 32.7 ms per frame. In the second experiment, we used the EM tracking system (medSAFE Ascension Technologies Inc.) as the ground truth, as shown in FIG. 28B-D. The porcine liver was placed in an abdominal phantom (The Chamberlain Group) and a medSAFE EM sensor was attached to the liver surface. We deformed the liver manually and recorded the EM sensor measurements and compared it with that of the process 600. Deformation estimation results on 420 video frames (FIG. 28C-D) show a mean error of 1.06 mm and standard deviation of 0.56 mm. As shown in FIG. 28C, the maximum distance between the trajectory points is 15.7 mm. The average runtime was 63.0 ms per frame: stereo matching 17.6 ms, ORB feature detection and matching 11.6 ms, inliers pre-selection 3.1 ms, LM 30.7 ms.

Figure 25:
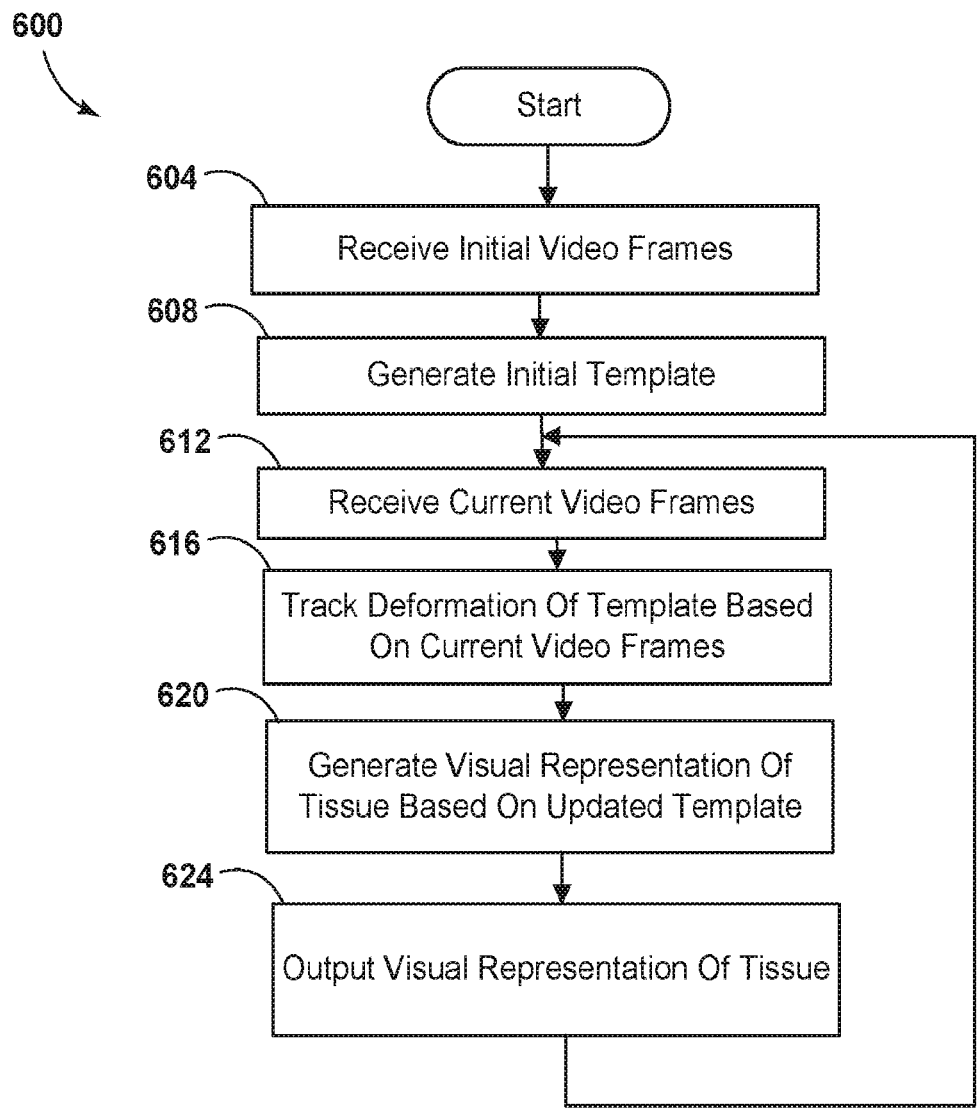
FIG. 25 is a flowchart of a process for determining tissue deformation.

FIG. 25 shows a process 600 for determining tissue deformation using at least some of equations (50)-(55) and a suitable stereo matching process. At 604, the process 600 can receive initial video frames including a video frame corresponding to a left camera included in a stereoscopic camera and another video frame corresponding to a right camera included in the stereoscopic camera. The stereoscopic camera can be included in a laprosocpe. The video frames can include views of at least a portion of a tissue. The process 600 can then proceed to 608.

At 608, the process 600 can initialize a template. The template can be generated using the stereo matching method 250. The process 600 can then proceed to 612. At 612, the process 600 can receive current video frames including a video frame corresponding to the left camera included in the stereoscopic camera and another video frame corresponding to the right camera included in the stereoscopic camera. The process 600 can then proceed to 616.

At 616, the process 600 can track deformation of the template based on the current video frames. The process 616 then updated the template. The process 600 can minimize the cost function Equation (50), perform ORB feature detection and matching, which may include using Equations (51)-(53), and perform ARAP smoothing using Equations (54)-(55) as described above in order to updated the template. The process 600 can then proceed to 620.

At 620 the process 600 can generate a visual representation of the tissue based on the template that was updated at 616. The visual representation can include a three-dimensional model. The process 600 can then proceed to 624. At 624, the process 600 can output the visual representation to at least one of a display and/or a memory. A medical practitioner may view the visual representation on the display. The process can then proceed to 612. Thus, a novel deformation recovery method that integrates the ORB feature, which is able to handle fast motion, smooth surfaces and occlusion is provided.

Feature matching is the foundation of many computer vision applications, such as simultaneously localization and mapping (SLAM), structure-from-motion (SfM) and image registration. The problem of detecting key points and extracting their descriptors from the input images has been studied for decades and many effective methods have been proposed, such as SURF and ORB. In recent years, deep learning-based methods have also been developed to improve the performance of feature detection and description. Correspondences between these feature points can be built according to the computed descriptors. However, due to noise, illumination change, camera motion and object deformation, incorrect matches, or outliers, are unavoidable. To remove outliers from the correct matches is essential for the feature-based applications, and the related methods can be roughly classified into parametric and non-parametric methods.

The parametric methods assume that there exists a simple analytical transformation between two point clouds, which include affine, homography, epipolar geometry and so on. For example, some have proposed an algorithm to extract the planar homography matrix from the matches, which is fast and accurate but requires the observed objects to be approximately planar or the camera rotates at a fixed location. To handle more general transformations, the most common method is random sample consensus (RANSAC), which has many modified versions. The RANSAC methods estimate the transformations from small sets of randomly selected control points, and select the transformation supported by the most number of matches as the final results. RANSAC is efficient in handling parametric transformations, but is difficult to handle non-parametric transformations, such as non-rigid deformation. To solve this problem, we propose a reasonable assumption that the non-rigid deformation can be approximately represented by multiple locally rigid transformations. However, traditional RANSAC methods have low efficiency under this assumption, because the selected sets of control points need to (1) be inliers and (2) can fit into the same rigid transformation. In this portion of the disclosure, we propose a novel re-weighting and 1-point RANSAC-based method (R1P-RNSC), which naturally satisfies the second condition because only one control point is needed in each trial. Hence, R1P-RNSC has high efficiency in handling non-rigid deformation while removing outliers in the feature matches.

Compared with parametric methods, non-parametric methods are more efficient in removing matching outliers when non-rigid deformation exists, which is an ill-posed problem. Most non-parametric methods are explicitly or implicitly based on the assumption that the deformation is smooth in local areas, and they recognize a match as an outlier if it is not consistent with its neighbors. For example, one group used the isometric deformation prior that assumed the distances between matches are preserved under deformations. Another group proposed a method to estimate the vector field from the matches, which achieved high performance in terms of speed and accuracy. That group further proposed to use machine learning methods to exploit the consensus of local neighborhood structures. Hence, the representation of the local smoothing information is essential for the accuracy of the non-parametric methods. In this portion of the disclosure, we propose an algorithm called as EMDQ based on dual quaternion to generate the smooth deformation field. Dual quaternion is widely used in the computer graphics field to generate smooth interpolations among 6-DoF rigid transformations. To reduce the impact of outliers, we integrate the dual quaternion-based interpolation process into the expectation maximization (EM) algorithm.

The method proposed in this portion of the disclosure includes two key steps, which are R1P-RNSC and EMDQ. The two algorithms compensate for the drawbacks of each other. The accuracy of R1P-RNSC is limited due to the lack of ability to take into account smoothing information. However, R1P-RNSC is fast and able to extract the candidate rigid transformations from the matches, which is essential for the initialization of the EMDQ algorithm. The experimental results show that the combination of the two algorithms has the highest accuracy compared with other state-of-the-art methods, and the speed is sufficient for real-time applications.

This portion of the disclosure is organized as follows. In the "Re-weighting and 1-point RANSAC (R1P-RNSC)" section, we give the details of R1P-RNSC, including the re-weighting strategy and the termination conditions of the RANSAC framework. The details of the EMDQ algorithm are given in the "Expectation Maximization and Dual Quaternion (EMDQ)" section, in which we also provide the strategy of initialization based on the results of R1P-RNSC. Evaluation results are presented in the "Experiments" section.

Related Works

Building correct correspondences between two point clouds in the presence of noise, outliers and deformation is a fundamental problem in the computer vision field, and the related research directions mainly include point clouds registration and feature matching.

Point Clouds Registration

This portion of the disclosure is related to the registration problem between point clouds or mesh models, which has been studied for decades with many effective solutions. The goal of point clouds registration is to assign correspondences between two sets of points and/or to recover the transformation that maps one point set to the other. The most popular point clouds registration method is iterative closet points (ICP), which has many variants. ICP iteratively assigns correspondences based on a closest distance criterion and finds the least-squares transformation between the two point clouds. To eliminate the impact of outliers, robust kernel functions can be applied. The ICP methods are sensitive to the initial alignment. To overcome this drawback, some works propose to use the soft-assignment strategy. For example, the robust point matching (RPM) algorithm uses a soft assignment matrix to represent the corresponding relationships. Another representative work is coherent point drift (CPD), which is based on the expectation maximization (EM) algorithm to calculate the probabilities of the correspondences between points. CFD considers one point set as the Gaussian Mixture Model (GMM) centroids, and the other one as the data points. Then, CFD fits the GMM centroids to the data to maximize the likelihood. Inspired by CPD, we have also employed the EM algorithm to obtain the probabilities of the matches according to the error distances to reduce the impacts of outliers.

To provide initial values and improve the robustness of point cloud registration, some methods proposed to extract descriptors of key points from the point clouds and build correspondences. For example, one group proposed a deep learning-based method called LORAX to describe the geometric structure of each point cloud with a low-dimensional descriptor. The obtained correspondences may include mismatches and an efficient method to remove these mismatches is needed.

Feature Matching and Outliers Removal

Feature matching is often a two-steps work. The first step detects feature points and builds matches. For example, there are many effective methods to detect key points and extract the descriptors from images, such as SIFT, SURF, ORB, A-SIFT and LIFT. There are also many works that aim to develop more robust and efficient matchers, such as FLANN. However, mismatches are often unavoidable after the first step, hence a following step to remove the mismatches is necessary. The problems in the first step have been studied for many years but little attention has been given to identifying outliers in the obtained matches.

It is very common that the correct matches in the images have a non-rigid deformation, because even when observing a rigid three-dimensional (3D) object from different angles and positions, the displacements of different parts of the object on the two-dimensional (2D) images are often non-rigid. It is difficult to pre-define a transform model to handle the non-rigid deformation when the 3D structures of the object are unknown. Hence, non-parametric methods are more flexible in handling the non-rigid deformation. For example, some have proposed the ICF algorithm based on a diagnostic technique and SVM to learn correspondence functions that mutually map one point set to the other. Then mismatches are identified according to the consistence with the estimated correspondence functions. Some have proposed a SIM algorithm that achieves affine invariance by computing the shape interaction matrices of two corresponding point sets. SIM detects the mismatches by removing the most different entries between the interaction matrices. Basically, these methods interpolate a non-parametric function by applying the prior condition, in which the motion field associated with the feature correspondence is slow-and-smooth. Similarly, another recent work proposed a regression algorithm based on as-smooth-as-possible piecewise constraints to discover coherence from the input matches.

Graph matching is another type of feature matching methods, which uses the nodes and edges to represent features and connections respectively. For example, some have proposed a spectral approach that uses weighted adjacency matrix to represent pairwise agreements between matches. Another group proposed a graph matching optimization technique to minimize the energy function defined by the appearance and the spatial arrangement of the features. Yet another group proposed a graph-based method to handle multiple patterns. Still others have proposed a method based on hierarchical agglomerative clustering. The graph matching methods are flexible to multiple types of transformations but suffer from the NP-hard nature.

Re-Weighting and 1-Point RANSAC (R1P-RNSC)

Under a reasonable assumption that a non-rigid deformation can be approximatively represented by multiple locally rigid transformations, we propose a method based on the re-weighting and 1-point RANSAC (R1P-RNSC) strategy to handle matching outliers when non-rigid deformation exists. Compared with traditional RANSAC methods that are based three or four control points, the ability to use only one control point to estimate the rigid transformations can naturally satisfy the requirement that all control points should have similar rigid transformations. The R1P-RNSC method is fast and can provide good initial values for the subsequent refinement step.

Re-Weighting

Matches between two point clouds may include outliers. Denote the two coordinates of the ith match as $x_i \in \mathbb{R}^D$ and $y_i \in \mathbb{R}^D$, i=1,2, ... N, where D=2 or 3 is the dimension of the point clouds. The rigid transformation between $x_i$ and $y_i$ can be represented by $$y_i = \mu(Rx_i + t), \quad (56)$$

where $R \in SO(D)$ is the rotation matrix, $t \in \mathbb{R}^D$ is the translation vector and $\mu \in \mathbb{R}$ is the scale factor.

In the R1PRNSC algorithm, we randomly select a match o as the control point, then the coordinates of other matches with respect to match o are $$y_i - y_o = \mu R(x_i - x_o), i=1,2,\ldots,N, \quad (57)$$

which suggests that a rigid transform can be represented by R, $\mu$, $x_o$ and $y_o$. Because $x_o$ and $y_o$ are constants, only R and $\mu$ are needed to be estimated. According to Ref., R and $\mu$ can be obtained from $x_i$ and $y_i$, i=1,2, ... N, by $$[U,\Sigma,V^T]=svd(YX^T), R=UV^T, \quad (58)$$

$$\mu=\|vector(Y)\|/\|vector(X)\|, \quad (59)$$

where $$X=[(x_1-x_o)\ldots x_N-x_o)]_{D\times N}, \quad (60)$$

$$Y=[(y_1-y_o)\ldots y_N-y_o)]_{D\times N} \quad (61)$$

Because match outliers exist and not all match inliers can fit into the local rigid transform of match o, the estimation of the rigid transformation represented by R and $\mu$ may be incorrect. We propose a re-weighting method to dynamically update the weights of matches i=1,2, ... N by $$d_i=\|y_i-y_o-\mu R(x_i-x_o)\|, \quad (62)$$

$$w_i=\min(H/d_i, 1), \quad (63)$$

where $d_i$ is the error distance of match i with the estimated R and $\mu$, H is a pre-defined threshold that when the error distance $d_i<H$, match i is recognized as an inliers.

With the obtained weights of matches $w_i$, i=1,2, ... N, the related items of matrices X and Y are adjusted according to the weights. Small weights $w_i$ will be assigned to the match inliers that cannot fit into the same rigid transformation of match o and the match outliers, hence the estimation of R and $\mu$ in Equation (58) and Equation (59) will not be interfered.

We perform the re-weighting strategy within an iterative process. With a randomly selected match o as the control point, we set the initial values of weights as $w_i=1$ for all matches. Then, we alternatively update R and $\mu$ according to Equation (58) and Equation (59), and update the weights of matches $w_i$, i=1,2, ... N, according to Equation (62) and Equation (63). In practice we find this iteration process only need a small number of iterations to converge, and we choose the number of iterations to be three in the experiments.

At the end of the iteration process, we recover the translation t by $$t=y_o/\mu-Rx_o, \quad (64)$$

which is not needed by R1P-RNSC for removing outliers, but the subsequent EMDQ algorithm need the estimation results of rigid transformations represented by R, t and $\mu$ to generate the initial dual quaternions.

Modified RANSAC

Traditional RANSAC methods aim to find the consensus that is supported by the most number of input data, and other consensuses are simply abandoned. It is difficult to use a single parametric transformation to represent the non-rigid deformation. To solve this problem, we propose to use multiple rigid transformations. In the R1P-RNSC algorithm, the rigid transformations are obtained in different RANSAC trials with different control points o. Hence, it is necessary to modify the standard RANSAC methods to reserve the obtained rigid transformations and design a new termination condition.

Results

Within the RANSAC framework, we randomly try different matches as the control point o. With a control point o, some matches may have small error distances $d_i$ as in Equation (62) and can be considered as the candidate inliers. Denote the number of candidate inliers detected with control point o as $T_o$, we omit the results if $T_o<T_{min}$, where $T_{min} \in \mathbb{R}$ is a threshold. A small $T_o$ suggests that the selected match o may be an outlier and the results obtained from it is incorrect. If $T_o \geq T_{min}$, we add the candidate inliers to the final inliers detection results, and update the inliers ratio by $$\gamma=N_{inliers}/N, \quad (65)$$

where $N_{inliers}$ is the total number of detected inliers.

In our algorithm, the control point o is only selected from the matches that are not considered as inliers so far, which aims to avoid repeatedly find the same rigid transformation.

RANSAC Termination

The standard termination condition of RANSAC is determined by the number of trials and the largest number of detected inliers in one trial, which needs to be modified for the R1P-RNSC algorithm. The basic idea of the modified RANSAC termination condition is to terminate the RANSAC process when inliers are unlikely to exist in the remaining matches.

$T_{min}$ is the minimal number of inliers detected by one trial that can be reserved. Assuming that there exist a set of $T_{min}$ inliers in the remaining matches, then the possibility that a selected control point o belongs to this set of inliers is $T_{min}/(N-\gamma N)$. Then, the possibility that after k trials of different control point o, the possibility that the a set of $T_{min}$ inliers is not found is $(1-T_{min}/(N-\gamma N))^k$, which equals to $1-p$. p is the widely used RANSAC parameter, which suggests the desired probability that the RANSAC algorithm provides a useful result after running and in our algorithm we set p=0.95. Hence, the termination of our 1-point RANSAC framework is $$k > \frac{\log(1-p)}{\log(1-T_{min}/(N-\gamma N))}, \quad (66)$$

where k is the number of RANSAC trials.

Sparse Implementation

The R1P-RNSC algorithm computes the rigid transformations by re-weighting all matches. A more efficient way is to use a small number of sample points $N_{sparse}<N$ to compute the rigid transformations, and then apply the obtained rigid transformations back to all matches to determine inliers and outliers. This sparse implementation is less accurate because it may miss possible rigid transformations to represent the non-rigid deformation, but is faster due the smaller number of matches involved in the re-weighting process.

The proposed R1P-RNSC algorithm is a parametric method that is efficient in estimating rigid transformations from the matches when outliers exist. However, R1P-RNSC suffers from a problem that it cannot take into account the smoothing information. For example, neighboring matches should have similar rigid transformations, but the estimated rigid transformations by R1P-RNSC are independent with different control points. Hence the accuracy is limited especially when repeating pattern exists. The repeating pattern may cause the feature points of a pattern be incorrectly matched to another pattern. These matching outliers are consistent with each other and are recognized as inliers by R1P-RNSC, because the number of outliers that satisfy with the same rigid transformation may larger than the threshold $T_{min}$. To solve this problem, we propose a non-parametric algorithm called as EMDQ as the refinement step.

Expectation Maximization and Dual Quaternion (EMDQ)

We propose a non-parametric algorithm called as EMDQ to handle matching outliers by generating the smooth deformation field. Denote a deformation field as f, $f(x_i)$ is the displacement of $x_i$ caused by f. Matching inliers should be consistent with the deformation field f, which suggest $$y_i \approx f(x_i), \quad (67)$$

for inliers.

According to Equation (67), the proposed EMDQ algorithm distinguishes inliers and outliers according to the error distances between $y_i$ and $f(x_i)$, i=1,2, . . . N. The ability to generate the smooth deformation field f from the matches with outliers is essential, and we employ dual quaternion to solve this problem.

Dual Quaternion-Based Deformation Field

We assign discrete transforms $g_i$, i=1,2, . . . N to all matches, and the smooth deformation field f is generated by interpolating among $g_i$. According to Equation (56), a transform $g_i$ consists of the rotation $R_i$, the translation $t_i$ and the scale $\mu_i$, which moves coordinate $x_i$ to $y_i$ by $$y_i=g_i(x_i)=\mu_i(R_i x_i + t_i). \quad (68)$$

Then, the value of f at a location is equal to the weighted average value of neighboring $g_i$. In this outliers removal problem, we mainly focus on the values of f at the locations of the matches $x_i$, i=1,2, . . . N, that is $$f_{x_i}=\Sigma_{j=1}^{N} w_j^i g_j, \quad (69)$$

where $w_j^i$ is the weight that suggests the impact from match j to i. $f_{x_i}$ is the value of f at the coordinate $x_i$. This weighted average strategy Equation (69) suggests that only when the transformations of neighboring matches are consistent with that of a match i, then match i can be recognized as an inlier according to Equation (67).

However, when performing interpolation according to Equation (69), the use of the rotation matrices and translation vectors as in Equation (68) may lead to inaccurate results. To overcome this difficulty, we introduce a mathematics tool called as dual quaternion (DQ).

A DQ is a 8-dimension vector that can represent a 3D rotation and a 3D translation simultaneously. A 2D transform can be considered as a 3D transform that is restricted at the z=0 plane, and 4 out of the 8 components of a DQ is always zero. To improve the efficiency, we only compute the 4 non-zero components in our EMDQ implementation when D=2. Hence, $q_i$ is a 4- or 8-dimension vector for D=2 or 3 respectively. Denote a dual quaternion related to match i as $q_i$, we have $$y_i=g_i(x_i)=\mu_i q_i(x_i), \quad (70)$$

where $q_i(x_i)$ suggests to apply $q_i$ to the coordinate $x_i \in \mathbb{R}^D$ to obtain a transformed coordinate.

According to Equation (69) and Equation (70), the deformation field f at the location $x_i$ is determined by the weighted average value of $\mu_j$ and $q_j$, that is $$f_{x_i}=\bar{\mu}_i \bar{q}_i \quad (71)$$

where $$\bar{q}_i=\Sigma_{j=1}^{N}(w_j^i q_j)/\|\Sigma_{j=1}^{N}(w_j^i q_j)\|_{dq}, \quad (72)$$

$$\bar{\mu}_i=\Sigma_{j=1}^{N}(w_j^i \mu_j)/\Sigma_{j=1}^{N}(w_j^i), \quad (73)$$

where $\|\cdot\|_{dq}$ is the norm of the dual quaternion. Many works in the computer graphics field have proven the feasibility and efficiency of using the linear combination of DQ as in Equation (72) to generate smooth interpolations. For example, by using DQ-based interpolation from skeletons, the motion of the skin surface of a mesh model can be generated. However, due to the existence of outliers, the interpolation process Equation (72) and Equation (73) may be incorrect. One way to reduce the impacts of outliers is to assign a small weight $w_j^i$ when match j is an outlier. Hence, we employ the expectation maximization (EM) algorithm to dynamically update the weights $w_j^i$ in the EM iteration process.

EM Algorithm

The EM algorithm is an iterative process that alternatively performs two steps. In the M-step, the probabilities that matches are inliers are computed, and the weights $w_j^i$ are further updated. In the E-step, the deformation field f is updated according to the weights $w_j^i$. The details of the EM algorithm is as follows.

M-Step

We consider the outliers removal problem as a classification problem according to the error distances between $y_i$ and $f(x_i)$, i=1,2, . . . N. With a deformation field f, we have $$p(i|\text{inlier}) = \frac{1}{2\pi\sigma^2}\exp\left(\frac{\|y_i - f(x_i)\|^2}{2\sigma^2}\right) \quad (74)$$

where σ is the standard variation.

We consider the outliers follow an uniform distribution, that is $$p(i|\text{oulier}) = a, \quad (75)$$

where a is a constant.

Denote γ as the inliers ratio, we have p(inlier)=γ and p(outlier)=1−γ. According to Bayes' theorem, we have $$p(\text{inlier}|i) = \frac{p(i|\text{inlier})p(\text{inlier})}{p(i|\text{inlier})p(\text{inlier}) + p(i|\text{outlier})p(\text{outlier})} \quad (76)$$

$$= \frac{\exp(\|y_i - f(x_i)\|^2/2\sigma^2)}{\exp(\|y_i - f(x_i)\|^2/2\sigma^2) + 2\pi\sigma^2\frac{(1-\gamma)}{\gamma}a}$$

p(inlier|i) suggests the probability that match i is an inliers. We adjust the weight $w_j^i$, which is the influence of match j to match i, according to p(inlier|j). Taking into account the distances between matches, $w_j^i$ is determined by two parts, that is $$w_j^i = w_{j,distance}^i p(\text{inliers}|j), \quad (77)$$

where $w_{j,distance}^i$ is determined by the distance between match i and j, that is $$w_{j,distance}^i = \max\left(\exp\left(\frac{\|y_i - y_j\|^2}{2r^2}\right), \exp\left(\frac{\|x_i - x_j\|^2}{2r^2}\right)\right) \quad (78)$$

where r∈ ℝ is a pre-defined radius. Because $w_{j,distance}^i$ does not contain variables, we only compute it at the initial phase.

E-step

According to the updated weight $w_j^i$, we update $\bar{q}_i$ and $\bar{\mu}_i$ for each match i according to Equation (72) and Equation (73) respectively, which represent the value of the deformation field f at $x_i$, or $f_{x_i}$.

The standard variation σ is updated by $$\sigma^2 = \Sigma_{i=1}^N (p(\text{inlier}|i)\|y_i - f(x_i)\|^2)/\Sigma_{i=1}^N p(\text{inlier}|i). \quad (79)$$

Finally, we update $q_i$ and $y_i$ to keep the transformation $g_i$ close to the deformation field $f_{x_i}$ by $$\Delta q_i = \text{trans2}dq((y_i - f(x_i))/\bar{\mu}_i), \quad (80)$$

$$q_{i,new} = q_{i,old}\Delta q_i, \quad (81)$$

$$\mu_{i,new} = \bar{\mu}_i. \quad (82)$$

Equations (80)-(82) aim to keep Equation (70) stands and make the transforms $g_i$ more smooth, and trans2dq represents the conversion of the transform to the DQ representation.

The termination condition of the EM algorithm determined by the change p(inlier|i), that is $$\frac{1}{N}\left(\sum_{i=1}^N |p(\text{inlier}|i)^{(k)} - p(\text{inlier}|i)^{(k-1)}|\right) < \theta \quad (83)$$

where θ is a threshold. k suggests the value of the kth iteration in the EM algorithm. After termination, matches with p(inlier|i)>$p_{min}$ and $y_i - f(x_i)$<H are considered as inliers, where $p_{min}$ is a threshold and H is the same threshold used in the R1P-RNSC algorithm.

Initialization from R1P-RNSC Results

There are mainly three variables in the EMDQ algorithm that need to be initialized, which include the DQ $q_i$, the scale factor $\mu_i$ and the weights between matches $w_j^i$. According to Equation (77), $w_j^i$ is determined by $w_{j,distance}^i$ and p(inliers|j), and $w_{j,distance}^i$ is constant in the EM iterations. The initial values of the three variables determine the initial deformation field f according to Equation (69), and we use the results of R1P-RNSC for the initialization.

The proposed R1P-RNSC algorithm detects multiple rigid transformations. If a match i is considered as an inlier with a rigid transformation detected by R1P-RNSC, then the related $q_i$ and $\mu_i$ will be initialized according to the results. A match i may satisfy multiple rigid transformations, and we use the one that has the most number of matches for EMDQ initialization. This initialization is important because as the examples shown in FIG. 29, there may exist multiple smooth deformations between two matches. Hence, if the $q_i$ and $\mu_i$, i=1,2, ... N are randomly initialized, the deformation field f may vary because it is generated by interpolating the $q_i$ and $\mu_i$ of neighboring matches. Hence, to remove this uncertainty, EMDQ relies on the results of R1P-RNSC for the initialization of $q_i$ and $\mu_i$, i=1,2, ... N.

Figure 29A:
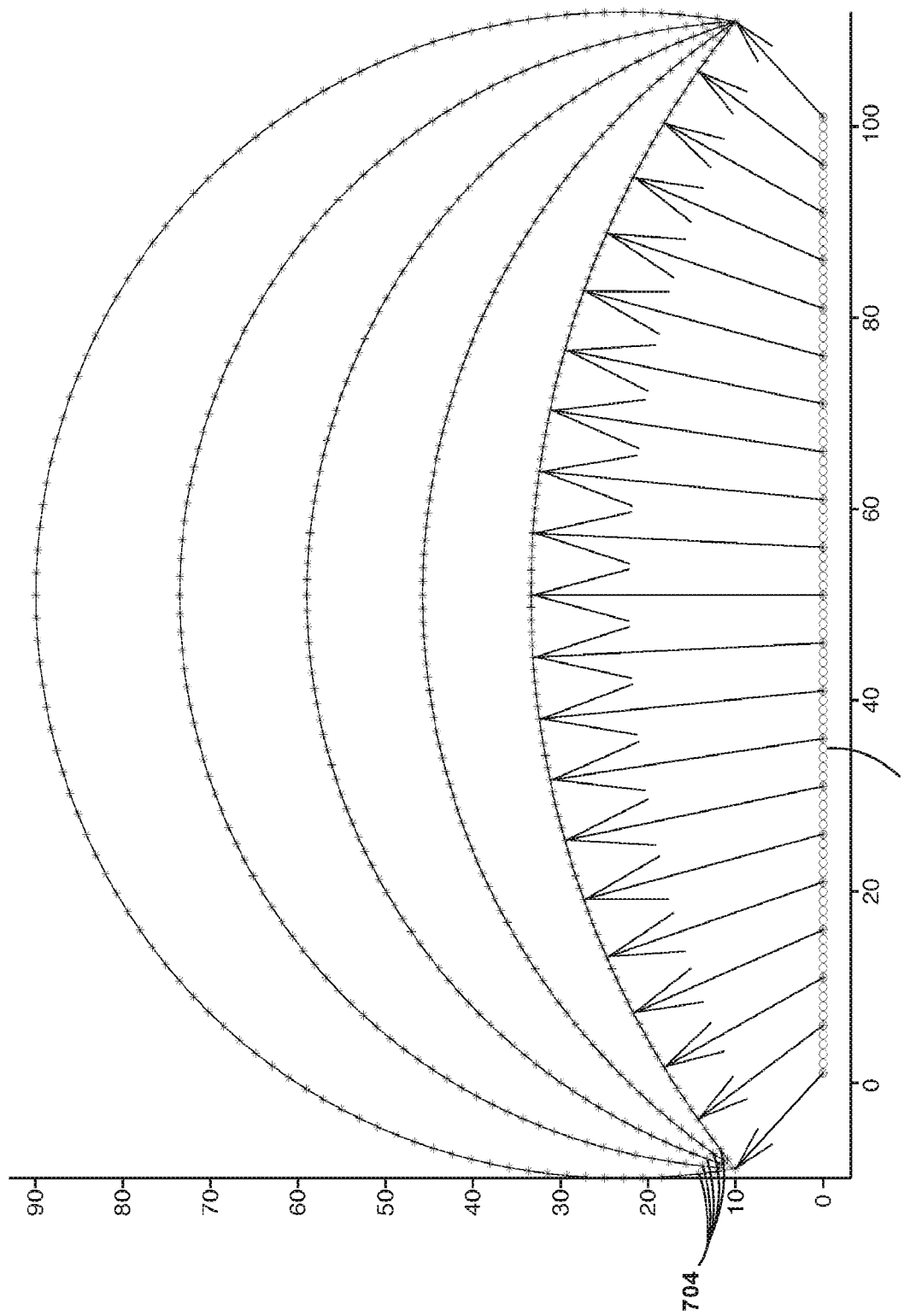
FIG. 29A is an example of a graph of uncertainty of smooth interpolation in 2D space.
Figure 29B:
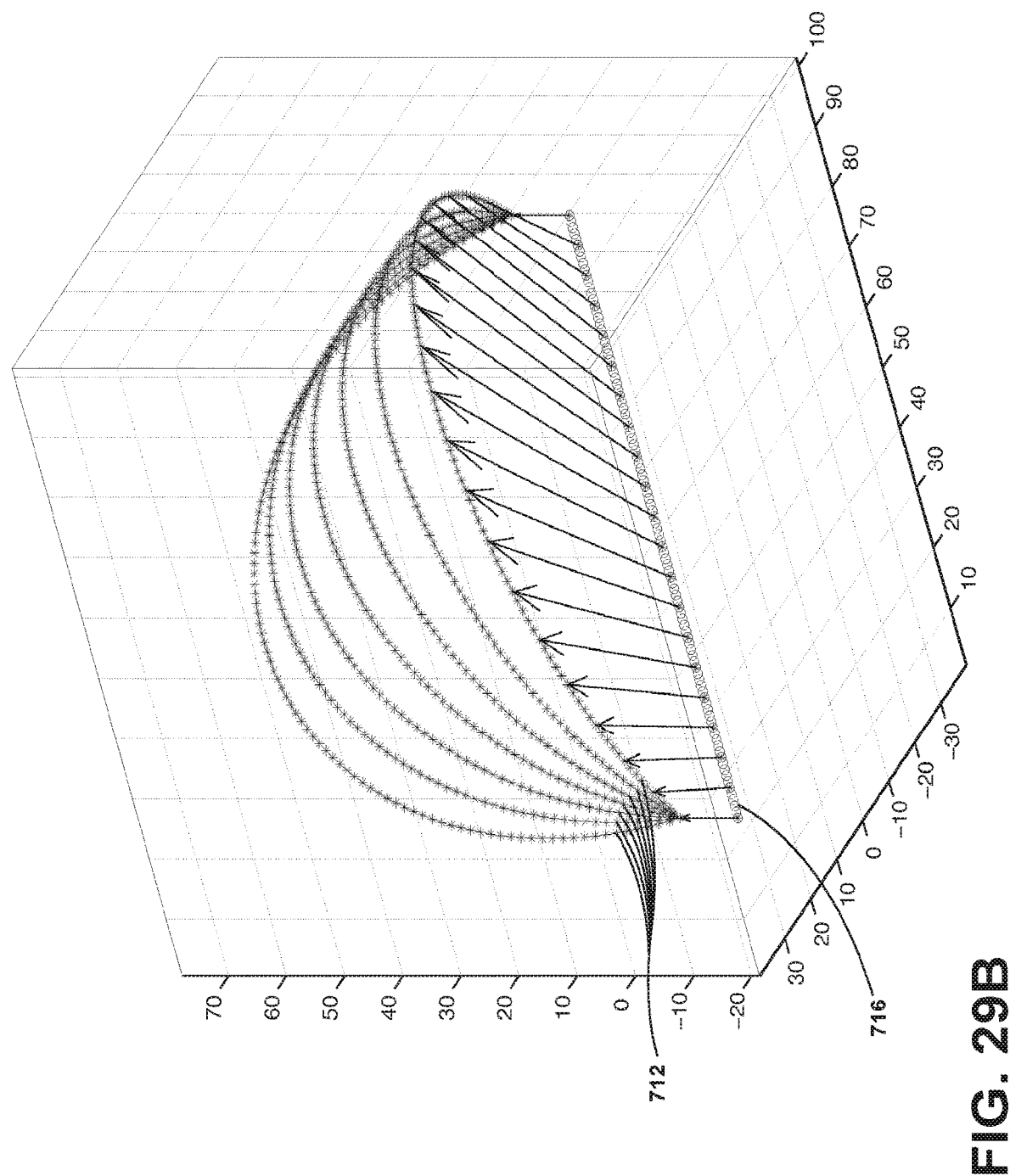
FIG. 29B is an example of a graph of uncertainty of smooth interpolation in 3D space.

FIG. 29A shows an example of uncertainty of smooth interpolation in 2D space, with curved lines 704 representing deformed point clouds and straight line 708 representing original point clouds. FIG. 29B shows an example of uncertainty of smooth interpolation in 3D space, with curved lines 712 representing deformed point clouds and straight line 716 representing original point clouds. Two end points are assigned with multiple different sets of dual quaternions, and other points are moved according to dual quaternion-based interpolation according to Equation (72) (in these examples we keep the scale μ=1). Although the sets of dual quaternion assigned to the end points result in the same displacements of the end points, the generated deformation of the point clouds may be different. All different deformations are smooth and may exist in reality, hence it is important to eliminate the uncertainty of interpolation and we use the results of R1P-RNSC to initialize the dual quaternion assigned to the matches.

The initial values of p(inliers|i) are important for reducing the impact of outliers when generating the initial deformation field f. The natural idea is to initialize p(inliers|i)=1 if match i is recognized as an inlier by R1P-RNSC, or p(inliers|i)=0. However, we found that this initialization cannot handle the repeating pattern very well, because at some local areas, there may be more false positives than true positives in the R1P-RNSC results, and the generated deformation field f yields false positives. We propose a simple method to overcome this problem according to the uncertainty of the detected rigid transformations provided by R1P-RNSC. With match o as the control point, R1P-RNSC may find different number of inliers, which is denoted as $T_o$. It is intuitive that when $T_o$ is large, the results are more reliable. Hence, we initialize p(inliers|i)=$T_o$ if match i is recognized as an inlier with match o as the control point. This allows that f is initially generated from the most reliable matches.

Experiments

The performance of the proposed algorithms was evaluated against state-of-the-art matching outliers removal methods. The source code was implemented in MATLAB and executed on a computer with an Intel Core i72.60 GHz CPU. In our MATLAB implementation, we used the vlfeat open source library for generating the kd-tree to obtain the neighboring matches.

The EMDQ algorithm requires R1P-RNSC for initialization. Hence, in this section, EMDQ reports the final accuracy and runtime results of the R1P-RNSC and EMDQ algorithms combined, while the sEMDQ reports the results when using the sparse implementation of R1P-RNSC.

2D Experiments

For 2D cases, the parameters of the R1P-RNSC algorithm are as follows: H=20 pixels is the inliers threshold; $T_{min}$=5 is the least number of inliers found by one R1P-RNSC trial that will be added to the final R1P-RNSC results. We used a large H and a small $T_{min}$, which aims to find as many rigid transformations as possible to represent the non-rigid deformation. Many outliers may be mis-recognized as inliers by R1P-RNSC, and we mainly rely on the subsequent EMDQ algorithm to remove these mis-recognized outliers. The parameters of the EMDQ algorithms are as follows: r=50 pixels is the radius to compute $w_{j,distance}^i$ between matches; a=1e−5 is used for computing p(i|outlier); $p_{min}$=0.5 is the threshold for EMDQ to determine inliers and outliers; θ=0.005 is threshold used in the termination condition of EMDQ iterations; $N_{neighbor}$=16 is the number of neighboring matches that are considered in the EMDQ algorithm, which are found by kd-tree.

The 2D experiments were mainly conducted on the DTU robot image data, which provides images and the related 3D point cloud obtained by structured light scan. The camera was fully calibrated and the true values of the camera positions and orientations are known. Images have a resolution of 800×600. Datasets numbered 1 to 30 were used. In each dataset, images were captured under nineteen different illumination situations and from one hundred and nineteen camera positions. We randomly selected 10 out of 19 illumination situations. Hence, a total of 30×10×119=35700 images were included in this evaluation. Following the instruction, for each dataset and illumination situation, we used the image numbered 25 as the reference image and performed SURF matching between the reference image and other images. By re-projecting the 3D point clouds to the images according to the true values of camera positions and orientations, we consider matches that have a re-projection error smaller than 10 pixels as inliers.

The outliers handling methods for comparisons include AHC, LPM, LMR, SIM and VFC. All the introduced methods were proposed in recent years and can reflect the state-of-the-art performances. It is worth noting that we did not introduce the traditional RANSAC+3 or 4 control points methods for comparison because they cannot handle the non-rigid cases, which is a key focus of this portion of the disclosure. In our experiments, we did not change the parameters of these methods. VFC has a fast version and a sparse version, which are referred to as fVFC and sVFC in this section. AHC is a very fast method for removing the matching outliers, which focuses on 3×3 projective transformations, namely planar homographies. However, for the DTU dataset, the images were captured with rotating 3D objects, hence the planar homographies assumption may not stand. LMR is based on machine learning to solving the two-class classification problem, and we use the trained neural network model provided by the authors as the classifier in this experiments.

The total number of matches and the percentage of outliers varied with objects, illumination situations and camera poses. Although clear comparisons require that only one factor be different, this kind of variable-controlling is difficult for the evaluation on real-world data because SURF matching results are unpredictable. In experiments we found that the accuracy of outliers removal algorithms was mainly affected by the percentage of outliers, and the runtime was mainly affected by the total number of matches. Therefore, in this section, we report the accuracy and runtime evaluation results by comparing the statistical results at each percentage of outliers and range of total number of matches respectively.

For accuracy evaluation, we report four metrics, which include the number of errors, F-score, recall and precision. The number of errors suggests the total number of differences between the ground truth and the inliers-outliers recognition results. F-score is widely used for statistical analysis of binary classification, and F-score=2Recall·Precision/(Recall+Precision).

Figure 30A:
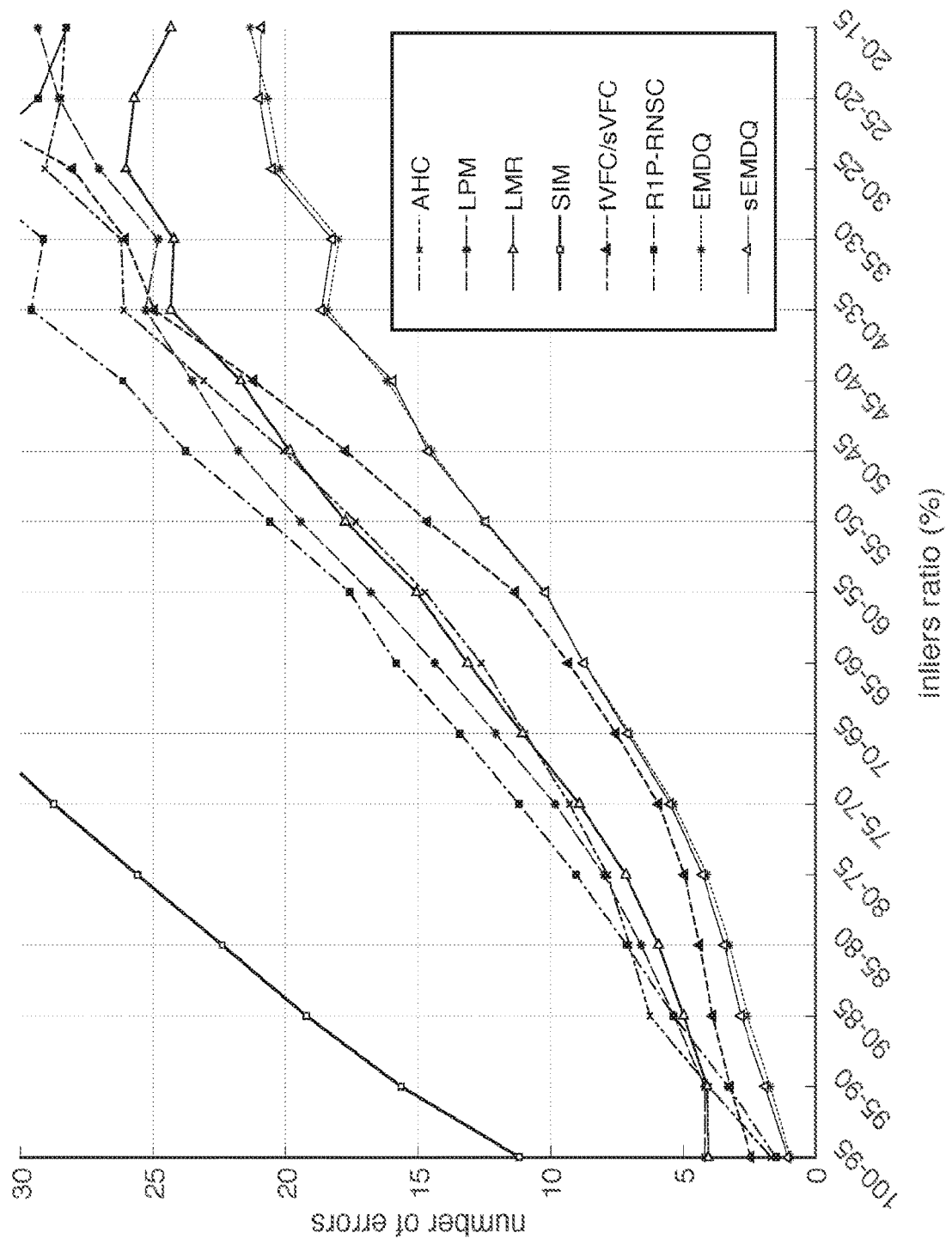
FIG. 30A is a graph of number of errors vs. inliers ratio for various matching methods used on Technical University of Denmark (DTU) data.
Figure 30B:
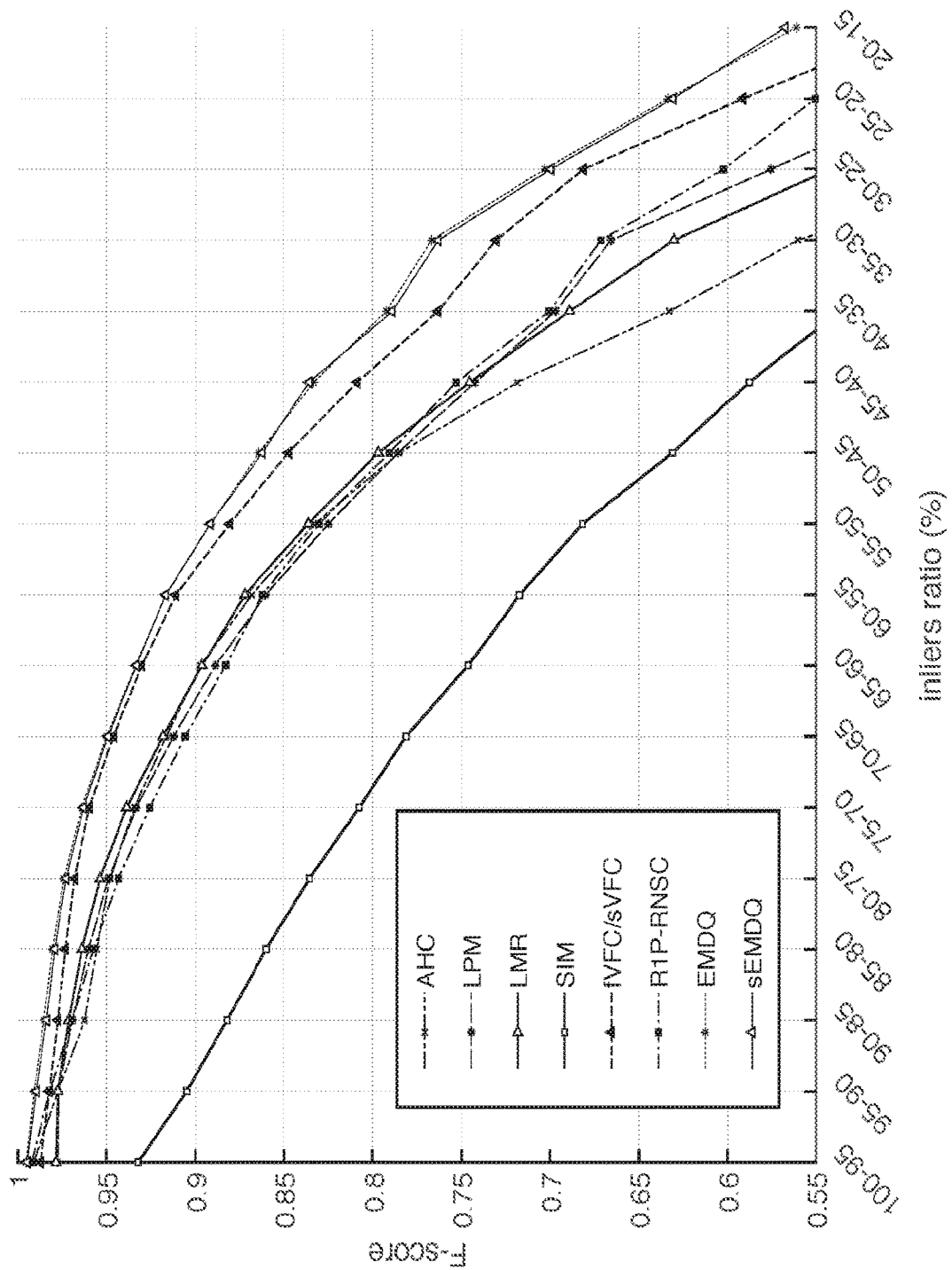
FIG. 30B is a graph of F-score vs. inliers ratio for various matching methods used on the DTU data.
Figure 30C:
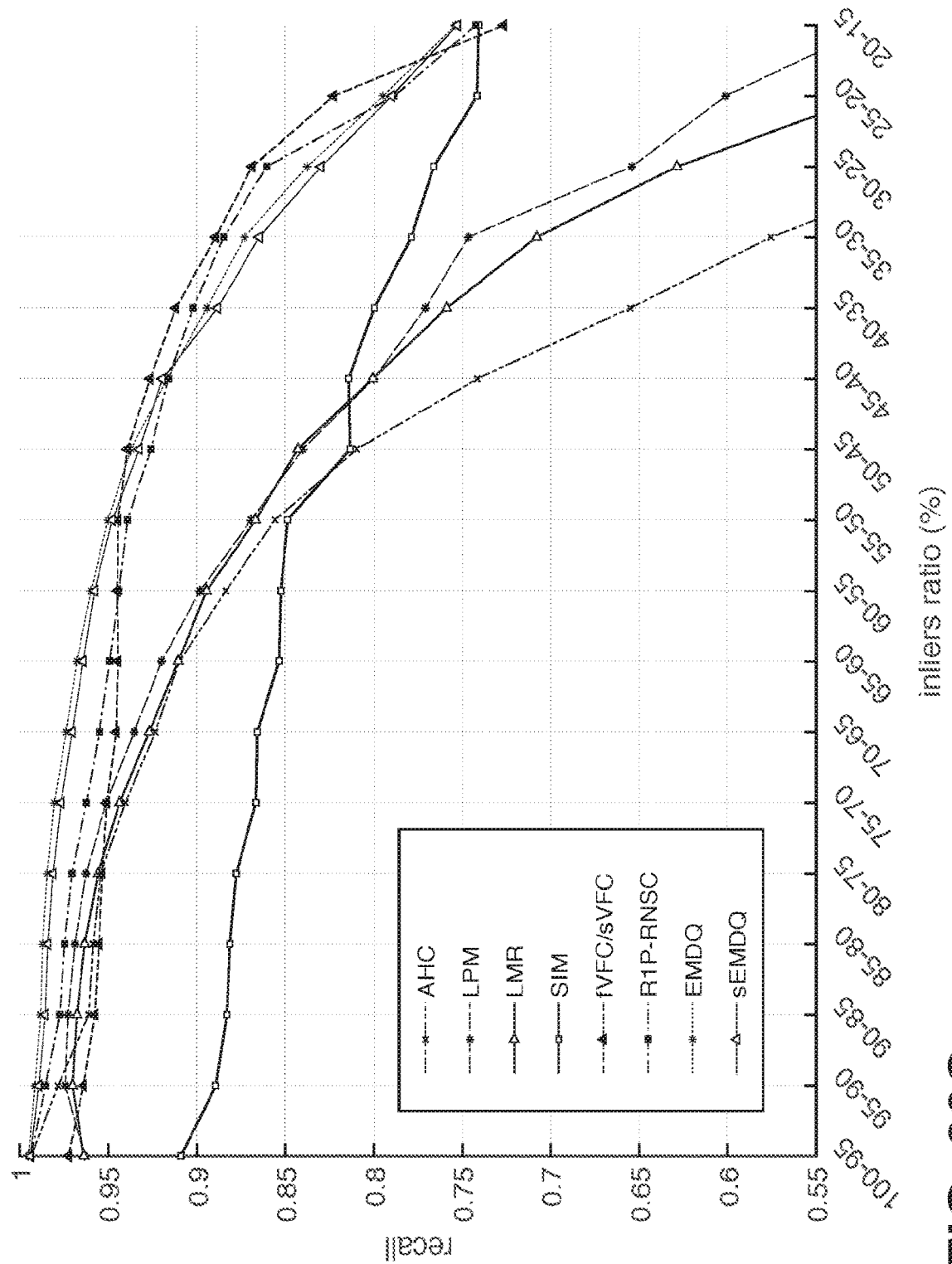
FIG. 30C is a graph of Recall vs. inliers ratio for various matching methods used on the DTU data.
Figure 30D:
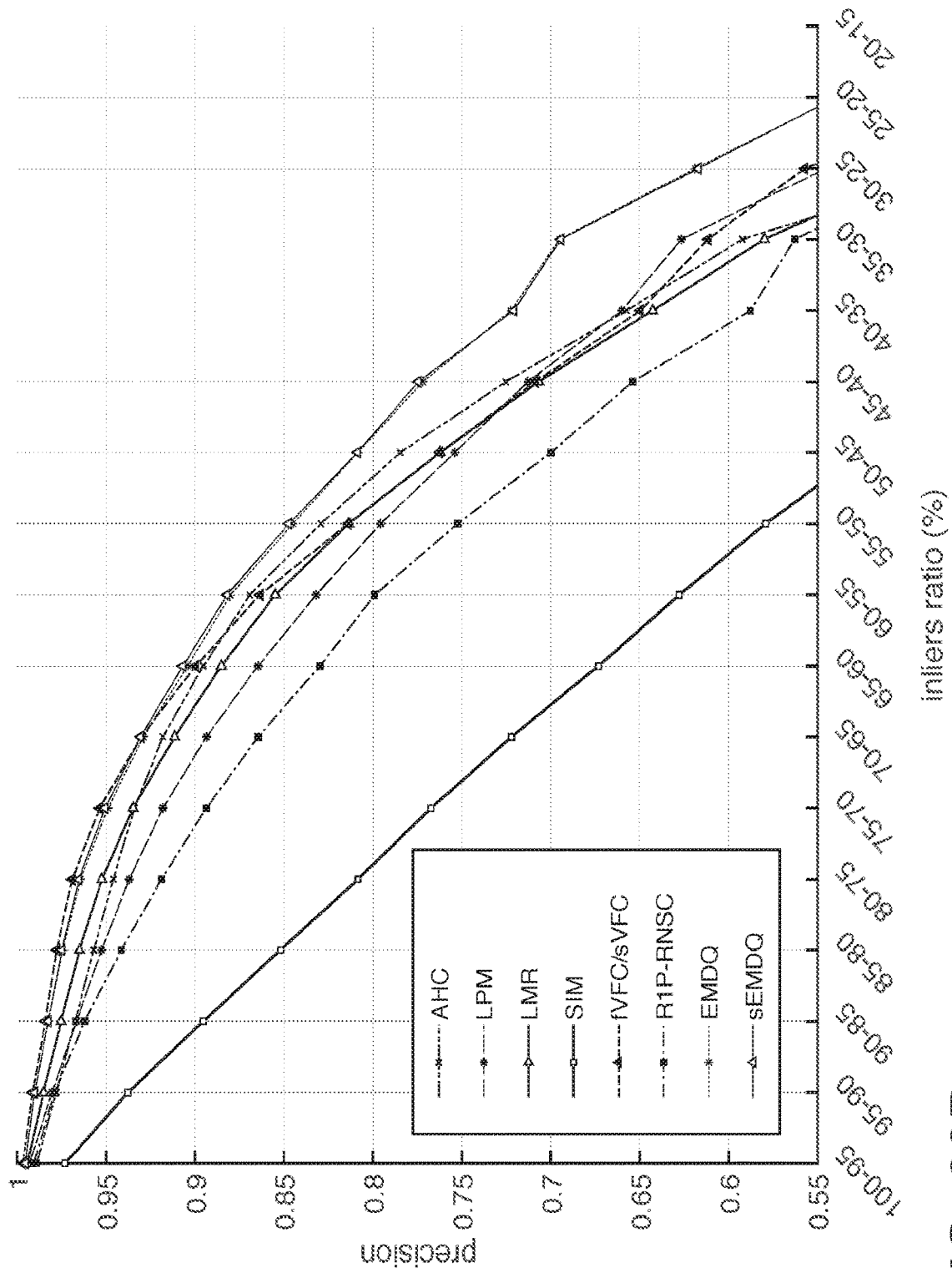
FIG. 30D is a graph of Precision vs. inliers ratio for various matching methods used on the DTU data.

FIG. 30A shows a graph of number of errors vs. inliers ratio for various matching methods used on the DTU data. FIG. 30B shows a graph of F-score vs. inliers ratio for various matching methods used on the DTU data. FIG. 30C shows a graph of Recall vs. inliers ratio for various matching methods used on the DTU data. FIG. 30D shows a graph of Precision vs. inliers ratio for various matching methods used on the DTU data.

As shown in FIG. 30, the proposed EMDQ method has the best accuracy in terms of number of errors and the F-score. sEMDQ did not show an obvious decrease in accuracy compared with EMDQ. Because we set a non-restrict threshold for 1P-RNSC, the recall rate of 1P-RNSC was high but the precision rate was low, which results in a comparable F-score with AHC, LPM and LMR. fVFC and sVFC had very similar results hence we combined them in FIG. 30. When the inliers ratio was high, the recall rate of fVFC/sVFC was lower than EMDQ/sEMDQ but the precision rate was slightly higher. As the inliers ratio decreased, the precision rate of fVFC/sVFC dropped significantly, which decreased their F-score significantly although the recall rate remained high.

Figure 31:
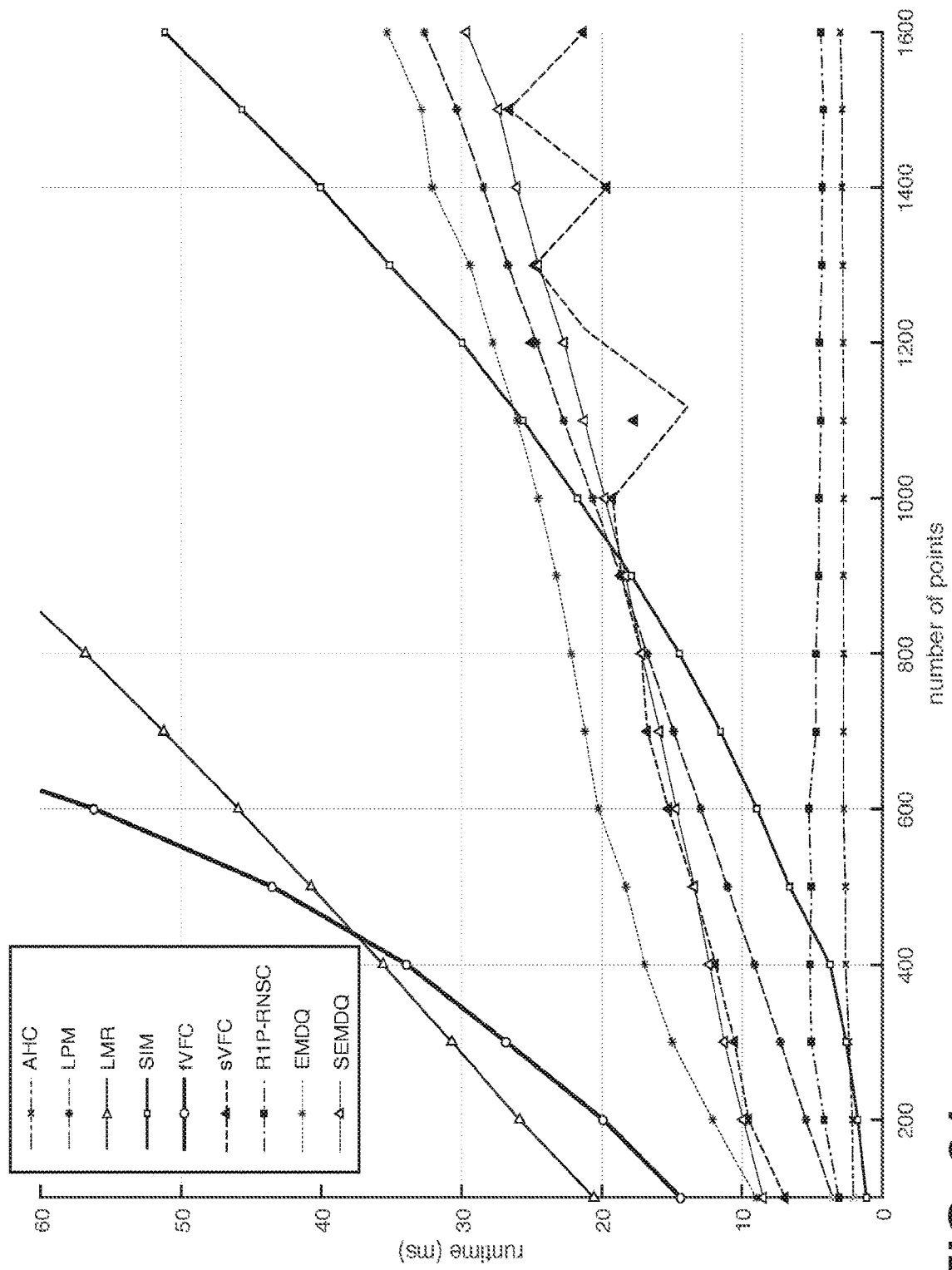
FIG. 31 is a graph of runtime vs. number of points for various matching methods.

As shown in FIG. 31, graph of runtime vs. number of points for various methods, sEMDQ had a comparable runtime with sVFC. AHC was fastest because it is based on an assumption that the object is planar, namely the planar homographies problem. This assumption makes AHC not suitable for solving the general outliers removal problem. Hence as shown in FIG. 30, the accuracy of AHC was lower than EMDQ and VFC. R1P-RNSC was also very fast.

The DTU dataset contains large data with different illuminations and object motion, hence it is sufficient for the evaluation of the proposed algorithms. Although the objects in the DTU dataset are rigid, the displacements of corresponding feature points on the images have large non-rigid deformation. In addition to the experiments on the DTU dataset, we also conducted qualitative experiments that included analyzing laparoscopic images of soft tissue undergoing non-rigid deformation due to physiological motions such as breathing, and tissue manipulation. The generated deformation fields by EMDQ were determined to be smooth and physically realistic.

3D Experiments

Most parameters for 3D cases are the same as that of 2D cases. However, because the scale of the input 3D point cloud may vary, we first developed a method to obtain the scale s to improve the adaptivity of the proposed methods, that is $$s = \sqrt{\frac{1}{2N}\left(\sum_{i=1}^{N}(x_i - \overline{x})^2 + \sum_{i=1}^{N}(y_i - \overline{y})^2\right)}, \quad (84)$$

where x and μ are the mean coordinates of $x_i$ and $y_i$, i=1, 2, . . . N, respectively. Certain parameters are adjusted for the 3D case as follows: H=0.1s, r=0.3s and a=20/s. Instead of normalizing the point cloud, we adjust the parameters according to scale s to obtain the deformation field f that can be directly used. In practice, we found that more neighboring matches are needed for 3D cases, hence we set $N_{neighbor}$=50.

We conducted the 3D experiments on medical data. The 3D models were generated by a stereo matching method from stereo laparoscopy videos. We performed ORB feature matching on the related 2D images and re-projected the feature points to the 3D models. The accuracy comparison results are shown in Table 4, which demonstrate that (s)EMDQ has the best accuracy. Compared with the generated results, the F-score is significantly higher in these experiments when the inliers ratio is low. This is because in these experiments, the modified ORB feature detection method can detect greater number of feature points than SURF, hence it is easier to generate the deformation field. The total number of matches are 629, 1784 and 693 for the three cases respectively, and the runtime of EMDQ are 53, 157 and 93 ms respectively.

At 816, the process 800 can output the deformation field generated at 812 to at least one of a memory or an external process.

In summary, two novel algorithms for solving the matching outliers removal problem, which are called as R1P-RNSC and EMDQ are presented in this disclosure. The two algorithms compensate for the drawbacks of each other. Specifically, R1P-RNSC is fast to extract hidden rigid transforms from matches with outliers, but it does not take into account smoothing information hence its accuracy is limited. EMDQ is based on dual quaternion-based interpolation to generate the smooth deformation field and have high accuracy, but it relies on the results of R1P-RNSC for initialization. The combination of R1P-RNSC and EMDQ achieves the best accuracy in terms of the total number of errors and F-score compared with other state-of-the-art methods. The proposed method is among the fastest methods for 2D cases, and can achieve real-time performance for 3D cases.

The proposed R1P-RNSC and EMDQ algorithms can be considered as a method to generate dense deformation field from sparse matches with outliers, which suggests that the displacements of all pixels can be obtained from the sparse matches (if uncertainty is not considered). Hence, the algorithms have potential to be used in many applications, such as non-rigid image registration.

This portion of the disclosure provides a method for accurate and real-time localization of breast tumors. Local-

TABLE 4

| 2* | case (a) (inliers ratio = 76%) | | | case (b) (inliers ratio = 39%) | | | case (c) (inliers ratio = 16%) | | |
|---|---|---|---|---|---|---|---|---|---|
| | recall | precision | F-score | recall | precision | F-score | recall | precision | F-score |
| LPM | 0.93 | 0.91 | 0.92 | 0.91 | 0.92 | 0.91 | 0.90 | 0.92 | 0.91 |
| LMR | 0.93 | 0.97 | 0.95 | 0.90 | 0.95 | 0.92 | 0.82 | 0.92 | 0.87 |
| SIM | 0.97 | 0.67 | 0.79 | 0.98 | 0.43 | 0.60 | 0.97 | 0.32 | 0.48 |
| VFC/sVFC | 0.99 | 0.94 | 0.96 | 0.99 | 0.96 | 0.97 | 0.99 | 0.94 | 0.96 |
| R1P-RNSC | 0.99 | 0.95 | 0.97 | 0.99 | 0.90 | 0.94 | 0.99 | 0.92 | 0.95 |
| EMDQ | 0.96 | 0.98 | 0.97 | 1.00 | 0.96 | 0.98 | 0.97 | 0.99 | 0.98 |
| sEMDQ | 0.97 | 0.98 | 0.98 | 0.99 | 0.96 | 0.97 | 0.97 | 0.98 | 0.98 |

Figure 32:
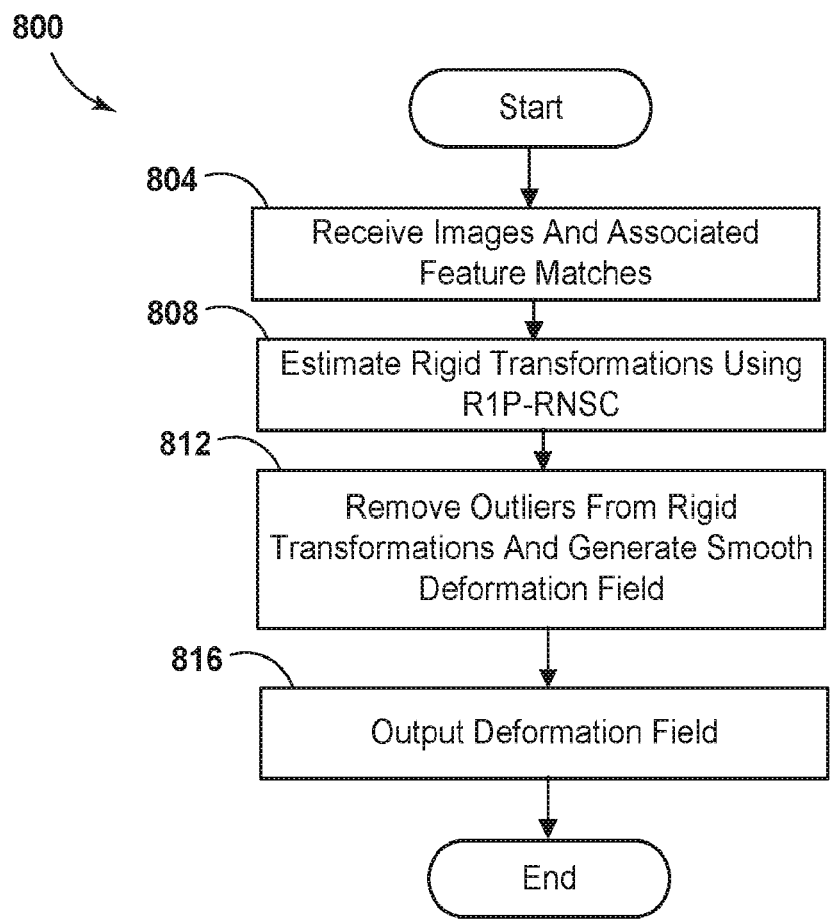
FIG. 32 is a flowchart of a method for generating a smooth deformation field.

FIG. 32 shows a method 800 for generating a smooth deformation field using the EMDQ algorithm described above.

At 804, the process 800 can receive images and associated feature matches (i.e., candidate feature matches) that have been previously generated. The feature matched may have been generated using an ORB-based technique. The process 800 can then proceed to 808.

At 808, the process 800 can estimate rigid transformations using R1P-RNSC. More specifically, the process 800 can estimate rigid transformations using at least one of the equations (56)-(66) and/or techniques described in the "Reweighting and 1-point RANSAC (R1P-RNSC)" section above. The process 800 can then proceed to 812

At 812, the process 800 can remove outliers from the rigid transformations estimated at 808 and generate a smooth deformation field using EMDQ. More specifically, the process 800 can remove outliers from the rigid transformations estimated at 808 and generate the smooth deformation field using Equations (67)-(83) and/or other techniques described in the "Expectation Maximization and Dual Quaternion (EMDQ)" section above. The process can then proceed to 816.

ization is essential for intraoperative navigation for lumpectomy. Standard diagnostic breast MRI cannot directly provide intraoperative navigation because it is performed in the prone position while lumpectomy is performed in the supine position, which causes significant deformation. To provide intraoperative navigation for lumpectomy, we propose a particle system-based (PS) method to calculate internal structural deformations with skin surface variations to localize the tumor.

Breast cancer is the most commonly diagnosed cancer among American women. In 2017, it is estimated that around 30% of newly diagnosed cancers in women will be breast cancers. Lumpectomy is one of the standard ways to cure breast cancer. Preoperative planning for lumpectomy is usually guided by diagnostic breast MRI, which is performed using a breast imaging coil in the prone position. However, the surgery is performed with the patient in supine position. Our previous clinical study has shown that the change of patient pose from prone to supine position causes significant displacement and deformation of breast tumors, therefore preoperative MRI cannot provide accurate intraoperative navigation and surgeons have to palpate to roughly localize the tumor during the surgery. The lack of accurate intraoperative localization of breast tumors may result in residual tumor so the patient may need a second surgery. The positive margin rate for lumpectomy have been reported to be as high as 35%.

To provide intraoperative navigation for lumpectomy, we propose a real-time breast deformation method to localize tumor by mapping the segmentation results of diagnostic MRI from the diagnostic prone to the surgical supine position. The deformation method mainly consists of three steps: (1) In the surgical planning stage, we segment the tumor, skin and chest wall from preoperative MRI with the 3D Slicer software. (2) During the surgery, we estimate the breast skin surface variations using stereo computer vision methods or depth map reconstruction. We have already developed a very efficient 3D reconstruction and tracking method running on GPUs. (3) According to the initial relative positions between the tumor and skin obtained in step 1, and the current skin model reconstructed in step 2, we estimate deformations of breast internal structures to localize the tumor. In this portion of the disclosure we will discuss the deformation algorithms used in step 3 and their validations.

The most widely used method to model deformations of soft tissues is finite element analysis (FEA). FEA is capable of handling complex objects, for example, a joint with bones and muscles. However, linear FEA suffers from inaccuracies under large strains or rotations. Non-linear FEA is precise but suffers from heavy computational burden. Hence non-linear FEA usually needs a tradeoff between speed and accuracy. For example, decreasing the number of elements can significantly speed up FEA but may lead to imprecise results. Although recent GPU parallel computing technology could make non-linear FEA methods more efficient, it is still attractive to develop simpler but accurate deformation methods.

Another type of deformation methods is based on the particle system (PS), which is widely used in the computer graphics field. The PS methods use virtual particles to represent physical units of the tissue. When controlling particles move, the rest particles are relocated following the as-rigid-as-possible (ARAP) rule. Compared with FEA, the PS method is much faster but suffers from difficulty to handle objects with complex stiffness. Fortunately, except for the tumor, stiffness inside of the breast is almost homogenous. PS methods can be divided into global and local methods. The global methods solve ARAP equations that use all particles as variables to find their optimal positions. Many computer graphics field researches have shown that global methods are efficient for handling high quality surface mesh. However, ARAP equations are sensitive to edge weights and usually use the triangular mesh angles to estimate edge weights, hence global PS methods incapable of handling deformation when internal structures need to be considered.

The main idea of the local PS method is that virtual particles only interact with their directly connected neighbors. Forces and motions are propagated through the connections. This Markov field-like model is reasonable because the motion of a real tissue unit is only directly related to its neighboring units. With surface variations, the deformation force model will update the deformation of the internal structures. Compared with global methods, local PS methods have much lower computational burden. The mass spring damper system is often employed for calculating the interaction forces between particles. However, the mass spring damper system has a significant drawback of not being able to take into account the variation in rotation directly. Although this drawback can be compensated by the implicit triangular stability in most cases, the mass spring damper system cannot handle situations with a large deformation.

To perform local particle system-based calculation, it is a prerequisite to build connections between particles. Many deformation methods use polygon meshes to represent the connections. However, for a three-dimensional (3D) structure, the Delaunay-based tetrahedral meshes generation is quite time consuming. Besides, the Delaunay-based methods need vertices as a prerequisite for performing mesh generation. Another type of deformation methods defines the connections by Euclidean distance thresholding, which greatly reduced the computation burden. For both types of deformation methods, the initial uniformly distributed particles with connections would improve the accuracy.

In this disclosure, we propose a novel local particle system-based algorithm to estimate the displacement of breast tumors from the diagnostic prone to surgical supine position. The main contribution of this disclosure are twofold: first, a novel sampling algorithm is proposed in the "Uniformly Sampling and Connections Generation" section to generate uniformly distributed particles inside of the breast, second; a novel local deformation model is proposed in the "Deformation Algorithm" section for calculating breast internal deformations and localize the tumor.

Uniformly Sampling and Connections Generation

A prerequisite for particle system-based breast deformation is to sample the breast with a given number of particles. Uniformly sampling could make the deformation estimation more accurate and smooth. Besides, it is necessary to build connections between particles hence motions could propagate through the connections. Because breast tumors are much more rigid than normal breast tissues, we did not take into account deformation of the tumor. Instead, we consider the tumor to be rigid and use one particle to represent the center of the tumor.

We first randomly generate particles inside the breast model, which is segmented from preoperative MRI. Then, particles receive virtual forces from the skin surface and their neighboring particles and move accordingly. Note that the virtual force model used in this section is only for uniformly sampling and while the deformation force model introduced in the next section will update the deformation of the internal structures based on the surface profile. For particle $p_i$, the relationship between its motion and the received virtual forces is given as follows:

$$dp_i = F_i/m \qquad (85)$$

$$F_i = \mu F_{surface \to i} + \Sigma_{j \in \Omega_i} F_{j \to i} \qquad (86)$$

where $F_i$ is the sum of all virtual forces it receives, $F_{surface \to i}$ is the virtual force applied from the surface to particle $p_i$, $F_{j \to i}$ is the virtual force applied from $p_j$ to $p_j$ (i≠j), $\Omega_i$ is the set of neighboring particles of $p_i$, m is the virtual mass of particles, and μ is a coefficient of weighting virtual forces.

In the following of this section we will discuss the details of the surface force calculation and how particles interact with each other.

Virtual Surface Force

The virtual surface force $F_{surface \to i}$ is introduced to keep particles inside of the breast model.

$$F_{surface \to i} = \begin{cases} 0 & \text{if } n_i \cdot d_{surface \to i} \leq 0 \\ -n_i & \text{if } n_i \cdot d_{surface \to i} > 0 \end{cases} \qquad (87)$$

where $d_{surface \to i}$ is the unit vector from the nearest surface point to $p_i$. $n_i$ is the unit normal direction of the nearest surface point, we assume $n_i$ points from inside to outside. As in Equation (86), the weight coefficient $\mu$ is a large number to make sure the virtual interaction forces between particles cannot push particles outside the breast model.

Particles Interaction

For uniformly sampling, we employed the concept that some entities repel or attract each other to avoid creating a density that is a too high or too low. We created a simple physical model by considering each particle as a balloon that is inflated gradually. The particles will repel each other when they come in contact. In this model we need to solve two problems: (1) how to calculate the interaction force, and (2) how to inflate or deflate the particles.

The interaction force applied from particle $p_j$ to $p_j$ is based on the simplified intermolecular forces (IMFs) model.

$$h = 1 \Big/ \left( \frac{a d_{i,j}}{r_i + r_j} + (1 - \alpha) \right) \qquad (88)$$

$$F_{j \to i} = (h^6 - h^3) d_{j \to i} \qquad (89)$$

where $d_{j \to i}$ is the unit vector from $p_j$ to $p_i$, $d_{i,j}$ is the distance between $p_i$ and $p_j$, $r_i$ and $r_j$ are the imaginary balloon radii, $\alpha$ is a coefficient. We choose $\alpha=0.5$.

The simplified IMFs model Equation (89) makes interaction force zero when $d_{i,j}=r_i+r_j$, i.e, when the particles are in a relaxed state. If $d_{i,j}<r_i+r_j$, $F_{j \to i} \cdot d_{j \to i} > 0$, which indicates particles will repel each other. On the other hand, if $d_{i,j}>r_i+r_j$, $F_{j \to i} \cdot d_{j \to i} < 0$ indicates particles will attract each other. When $p_i$ is far away from $p_j$, their interaction force will gradually decrease to zero.

In our algorithm, each particle $p_i$ gradually dilates, however, the particle interaction forces may compress the particle. The particle interaction force applied on $p_i$ can be divided into two parts (see Equation (90)). The first term on the right side of Equation (90) represents the motion of $p_i$ due to repulsive forces, and the second terms represents compressive forces on the particle.

$$\Sigma_{j \in \Omega_i} |F_{j \to i}| = |\Sigma_{j \in \Omega_i} F_{j \to i}| + |F_{compress,i}| \qquad (90)$$

where $|F_{compress,i}| \in R$ is a scaler.

Due to significant computational time, it is not appropriate to make the end point of the convergence progress near $d_{i,j}=r_i+r_j$, where the interaction forces are near zero. Hence, in our design, the algorithm converges at $d_{i,j} \neq 0.75(r_i+r_j)$, where particles are still repelling each other to reduce the computational time.

Considering a close-packing of equal spheres, which is an ideal uniform sampling pattern, each sphere has 12 adjacent spheres. Presuming that each balloon stops changing its radius at this ideal situation, from Equation (88) and Equation (89) the compressive force is as follows:

$$|F_{compress,i}^{ideal}| = \qquad (91)$$

$$\frac{12}{\left( \frac{0.5 \times 0.75(r_i + r_j)}{r_i + r_j} + 0.5 \right)^6} - \frac{12}{\left( \frac{0.5 \times 0.75(r_i + r_j)}{r_i + r_j} + 0.5 \right)^3} = 8.8257$$

Consequently, $r_i$ updates according to the compression force:

$$dr_i = -ln(1.0 + \eta(|F_{compress,i}| - |F_{compress,i}^{ideal}|)) \qquad (92)$$

where $\eta$ is a coefficient suggesting the hardness of each balloon.

According to Equation (92), when $|F_{compress,i}| < |F_{compress,i}^{ideal}|$, the radius $r_i$ becomes larger. According to Equation (89), $p_i$ will have larger interaction forces with neighboring points than before, which tends to make $|F_{compress,i}|$ larger. Similarly, when $|F_{compress,i}| > |F_{compress,i}^{ideal}|$, our algorithm tends to make $|F_{compress,i}|$ smaller. This forms a negative feedback system, with the result that all variables in our algorithm, including the points distribution, become stable.

For particle $p_i$, we assume it is connected to each particles in its neighboring particles set $$\Omega_i = \{j | d_{i,j} < 0.6(r_i + r_j)\}. \qquad (93)$$

Figure 33B:
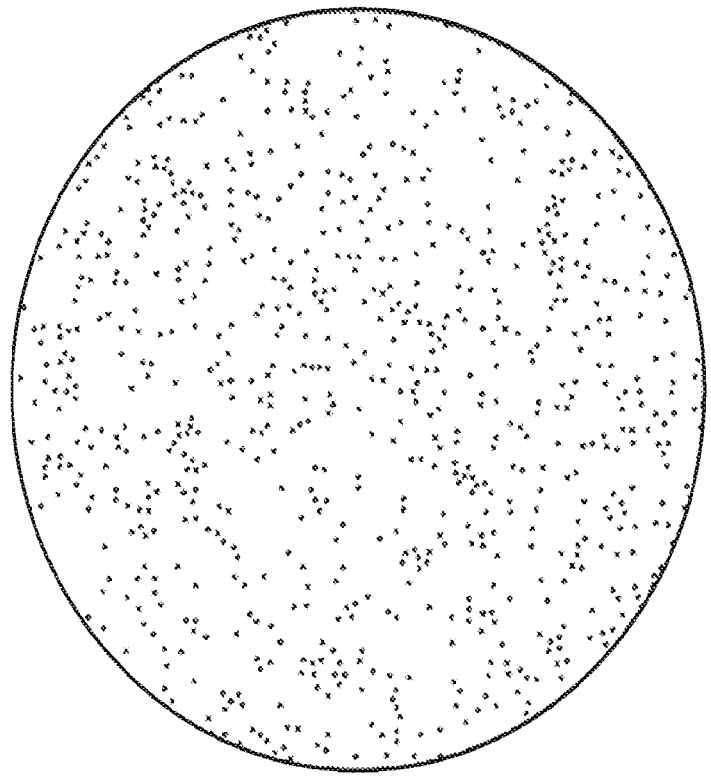
FIG. 33B is a graph of the particles after 5 iterations of a method.
Figure 33A:
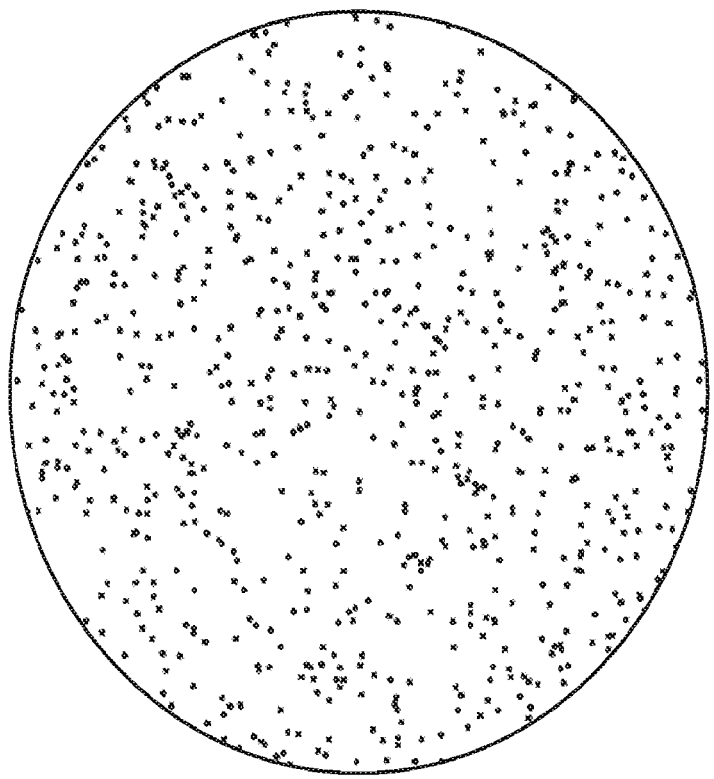
FIG. 33A is a graph of exemplary initial particles.
Figure 33D:
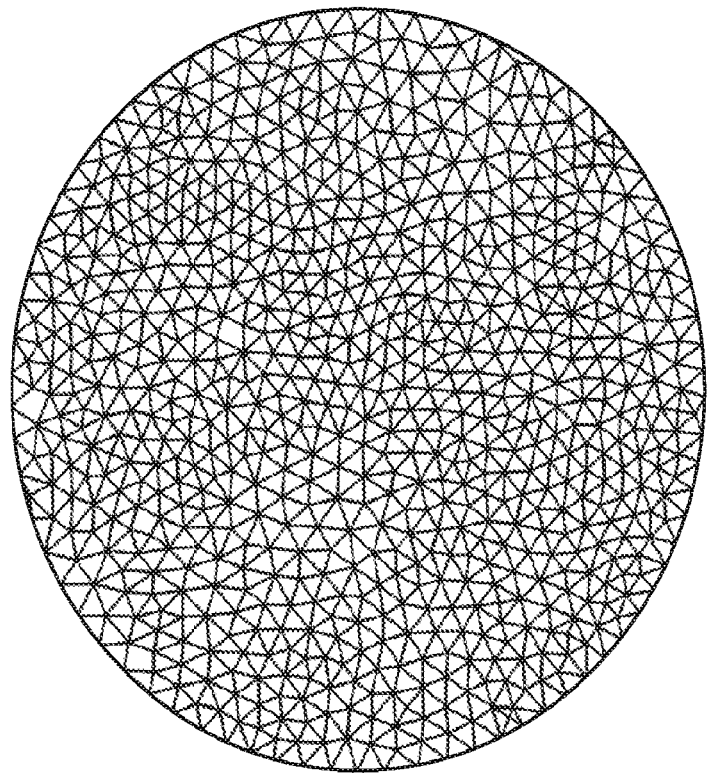
FIG. 33D is a graph of the final particles with connections.
Figure 33C:
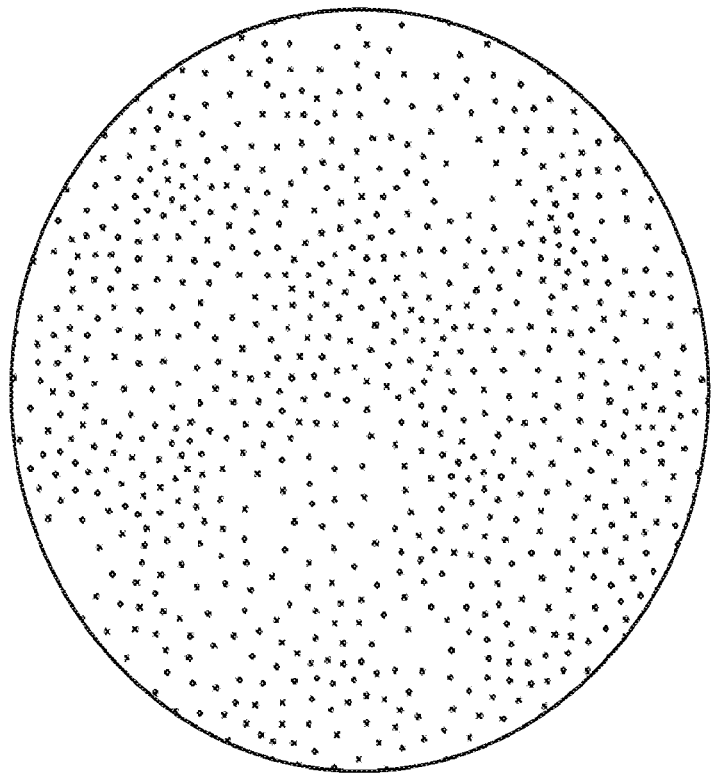
FIG. 33C is a graph of the particles after 10 iterations of the method.

FIG. 33A shows initial particles. FIG. 33B shows the particles after 5 iterations. FIG. 33C shows the particles after 10 iterations. FIG. 33D shows the final particles with connections. Our method generates particles on both surface and inside. Those surface particles will be used as the control points in the subsequent deformation simulation and their position changes according to the change of surface.

Deformation Algorithm

Figures 34A, 34B:
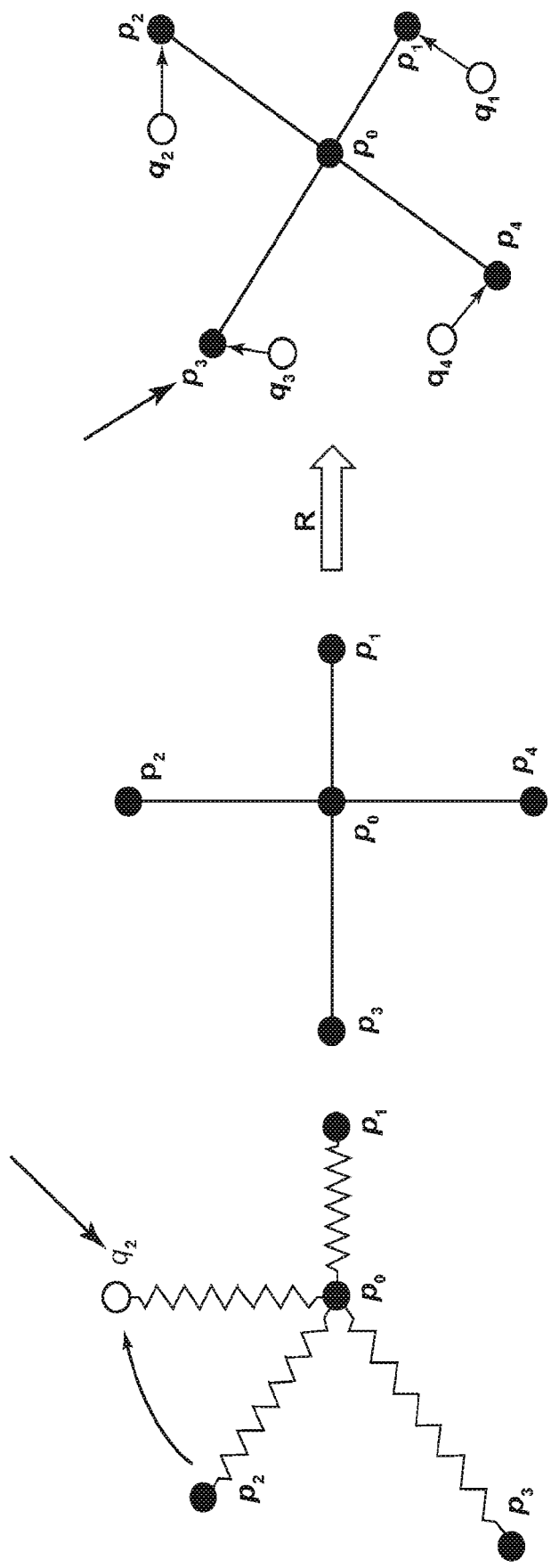
FIG. 34A shows a model of how a mass spring damper system cannot take into account certain deformations.
FIG. 34B shows an interaction force model.

The particles' initial distribution and connections are generated by the uniformly sampling method introduced in the "Uniformly Sampling and Connections Generation" section. If skin surface profile varies, the surface particles, which are considered as the controlling particles, will change their positions accordingly and apply deformation forces to internal particles connected to them. The surface particles deformation is propagated deeper into the internal structure and the final new distribution should follow the as-rigid-as-possible rule compared with the initial distribution. To date, the mass spring damper force model has been extensively used for deformation simulation. However, mass spring damper force model has a major drawback of not being able to take into account angles variation directly, as shown in FIG. 34A. Although implicit triangular stability could compensate for this drawback, in practice the mass spring damper force model cannot handle large deformation.

FIG. 34A shows how if particle $p_2$ moves to $q_2$ and keeps $|p_2 p_0|=|q_2 p_0|$, the mass spring damper system cannot take into account this deformation and no force is generated. FIG. 34B shows the interaction force model. After estimating rigid rotation R, the relax shape $p_i$ are compared with the current shape $q_i$ and deformation forces are generated (in arrows).

We propose a novel interaction force model to take into account all local deformation information. The idea of this deformation force model is straight forward, as shown in FIG. 34B. For a particle $p_i$ and its connected particles $p_j, j \in \Omega_i$, the change of their relative positions may cause interaction force. Because the relative position variations are affected by both rigid rotation and shape deformation, we need to first get rid of the effect caused by rigid rotation.

Denoting particles at the initial state as p and those at the current state as q, the related local shape at particle i can be described in matrix form:

$$A_{initial,i} = \begin{bmatrix} (p_j 1 - p_i)^T \\ \vdots \\ (p_{jn} - p_i)^T \end{bmatrix}_{n \times 3}, A_{current,i} = \begin{bmatrix} (q_j 1 - q_i)^T \\ \vdots \\ (q_{jn} - q_i)^T \end{bmatrix}_{n \times 3} \quad (94)$$

We find a rotation matrix $R_i$, which minimizes $$\|A_{initial,i} R_i - A_{current,i}\| \quad (95)$$

Hence, $R_i$ can be found as follows:

$$[U, S, V^T] = svd(A_{initial,i}^T A_{current,i}) \quad (96)$$

$$R_i = UV^T \quad (97)$$

The deformation force applied from particle i to j is:

$$F_{i \to j} = \sigma(R_i^T (p_j - p_i) - (q_j - q_i)) \quad (98)$$

where $\sigma$ is a coefficient suggesting the stiffness of the local tissue.

After calculations of all points we can get the sum of forces that a particle receives, and then we move particles according to the motion model Equation (85).

Experiments

In this disclosure, we propose a method to localize breast tumor from skin surface variations. To evaluate the speed and accuracy, we have collected patients' breast MRIs performed in both prone and supine positions. 20 patients with a new diagnosis of breast cancer who underwent MRI for staging at our hospital were included in the study. Standard breast MRIs were performed in prone position, and the patient was then placed in supine position and one axial T1-weighted VIBE image was then obtained with a 6-channel body coil. The MRIs were loaded, and the chest wall, skin, and tumors were segmented and surface mesh models were created from the corresponding prone and supine MRIs using 3D Slicer (slicer.org). First post-contrast prone and supine images were registered based on thoracic cavities using the Mutual Information criterion, and corresponding models were registered. The proposed particle system-based algorithms is performed to estimate the tumor location in the supine position according to the tumor in the prone position and the skin surface variations, and then compared with the segmentation results of supine MRIs. The algorithms proposed in this disclosure were implemented in C++ and VTK running on a 2.60 GHz Intel Core i7 processer.

Runtime

Figure 35A:
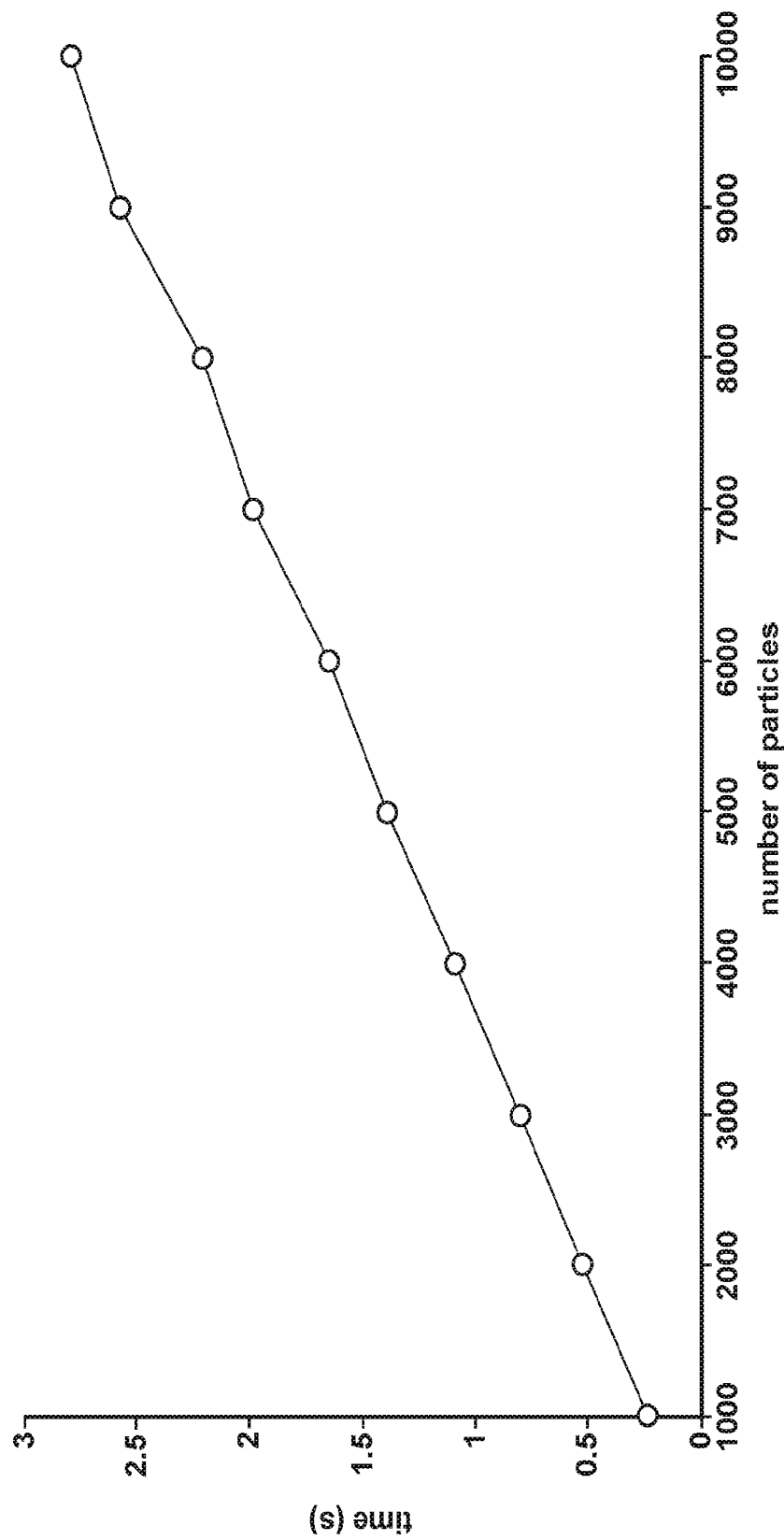
FIG. 35A is a graph of runtime of a uniformly sampling method.
Figure 35B:
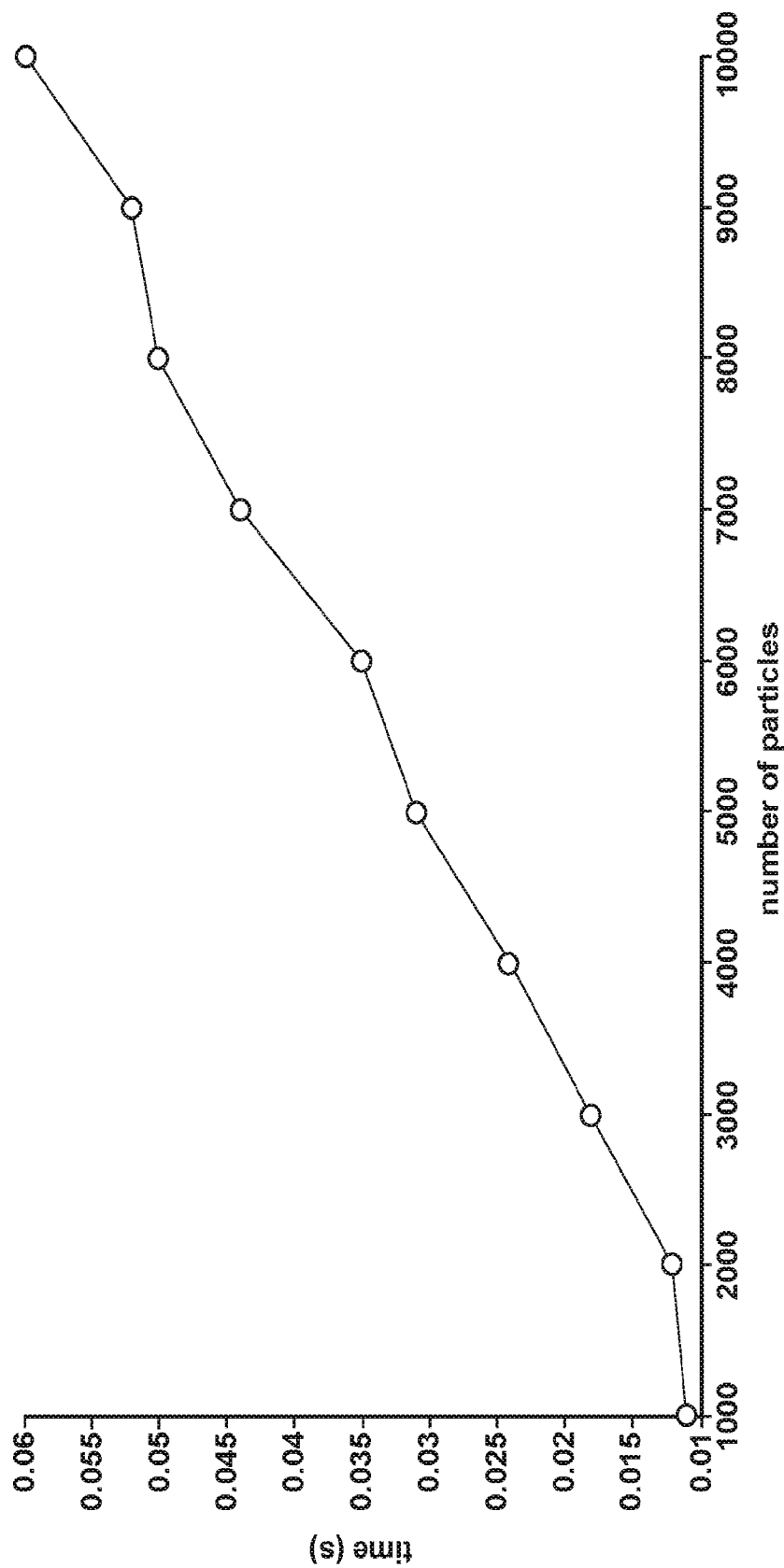
FIG. 35B is a graph of runtime of one iteration of a deformation algorithm.

FIG. 35A shows runtime of the uniformly sampling method. FIG. 35B shows runtime of one iteration of the deformation algorithm. Each point represents 100 trials.

Both algorithms, the uniformly sampling and deformation estimation algorithm, have linear time complexity with respect to the number of particles. In experiments we found that the runtime variations are very small with different pairs of prone and supine MRIs when the number of particles are the same. Hence, we evaluated their runtime with different number of particles varying from 1,000 to 10,000.

As shown in FIG. 35A, the uniformly sampling algorithm took less than 3 seconds for processing up to 10,000 particles. Because the uniformly sampling algorithm is only performed at the initialization stage, the real-time performance relies mostly on the deformation algorithm. As shown in FIG. 35B, one iteration of the deformation algorithm took an average of less than 60 ms for handling up to 10,000 particles, which is very fast. It should be noted that the required number of iterations depends on how large the relative deformation is between two states, hence it is not appropriate to give an exact total runtime needed for deformation simulation. In experiments we found that for consistently tracking a deforming object in realtime, it usually needed less than five iterations to change from one state to a new stable state. This suggests that for 10,000 particles, the average deformation runtime is around 0.3s.

Accuracy

The tumors were pre-segmented from both prone and supine MRIs, the latter of which was considered as the gold-standard segmentation to evaluate the deformation algorithm. The deformation algorithm calculated the effect of breast skin deformation on the displacement of the breast tumor, and compared positions between the displaced prone tumor and the real supine tumor. The breasts skin deformation were obtained by aligning intraoperative prone and supine breast MR imaging. Thereafter, the displacement of the prone tumor label map was computed based on the particle position at the center of the label map and overlaid on the supine MRI.

The error between the estimated position of the displaced prone tumor model and the position of supine tumor model was computed. For the 20 cases, the average error between the estimated and true position of the tumor model in the supine position is 3.66 mm, range=0.99 mm to 8.59 mm. For 16/20 cases, the average error distance was less than 5.0 mm. 15 cases have significant overlap between the estimated and true supine tumor models. For case 14 and 16 on the graph, the sizes of the breast tumors are 47 mm and 72 mm respectively; therefore a relatively larger maximum error distance is acceptable.

Figure 36A:
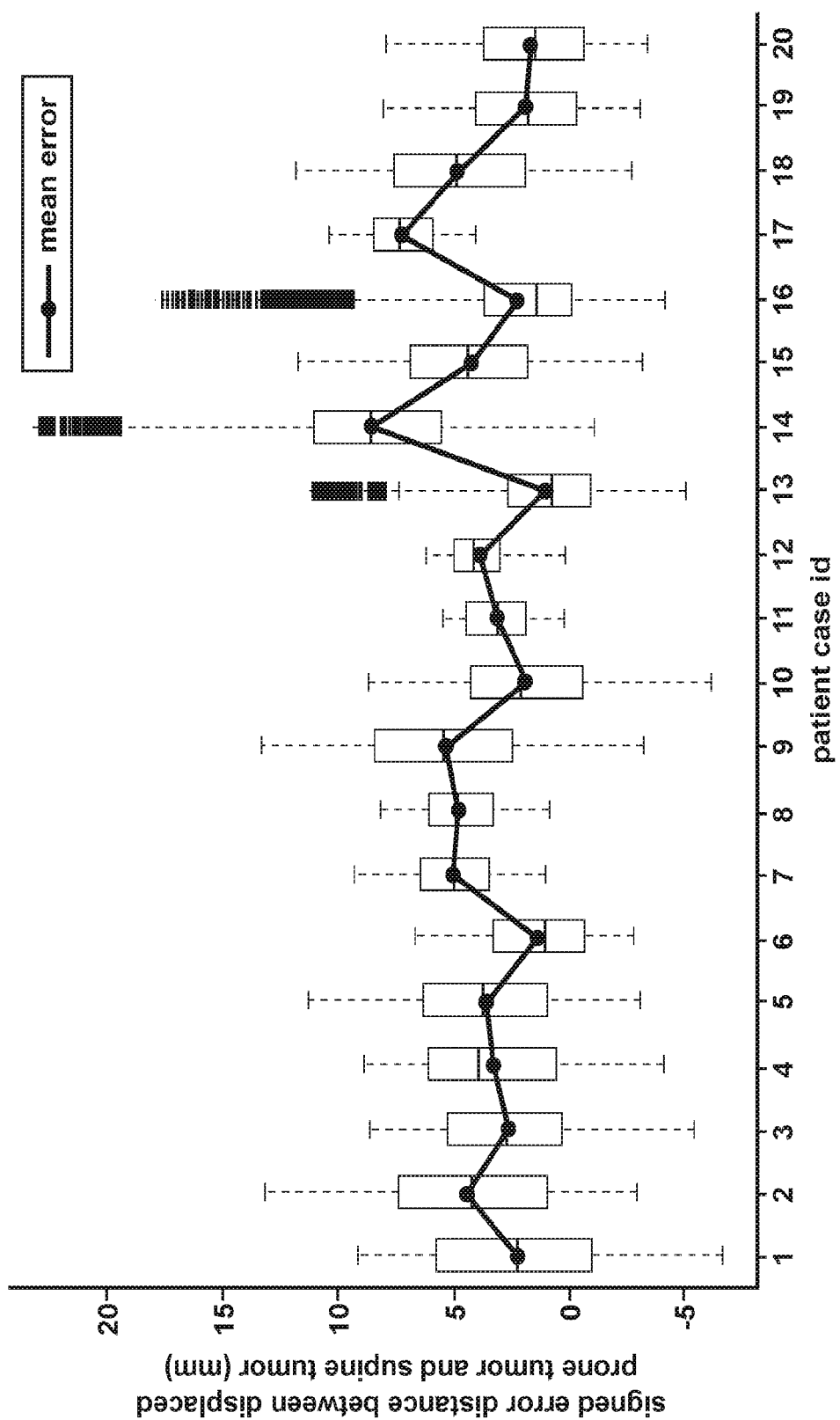
FIG. 36A is a graph of signed distance of all mesh model vertices between displaced prone tumor and real supine tumor for twenty cases.
Figures 36B, 36C:
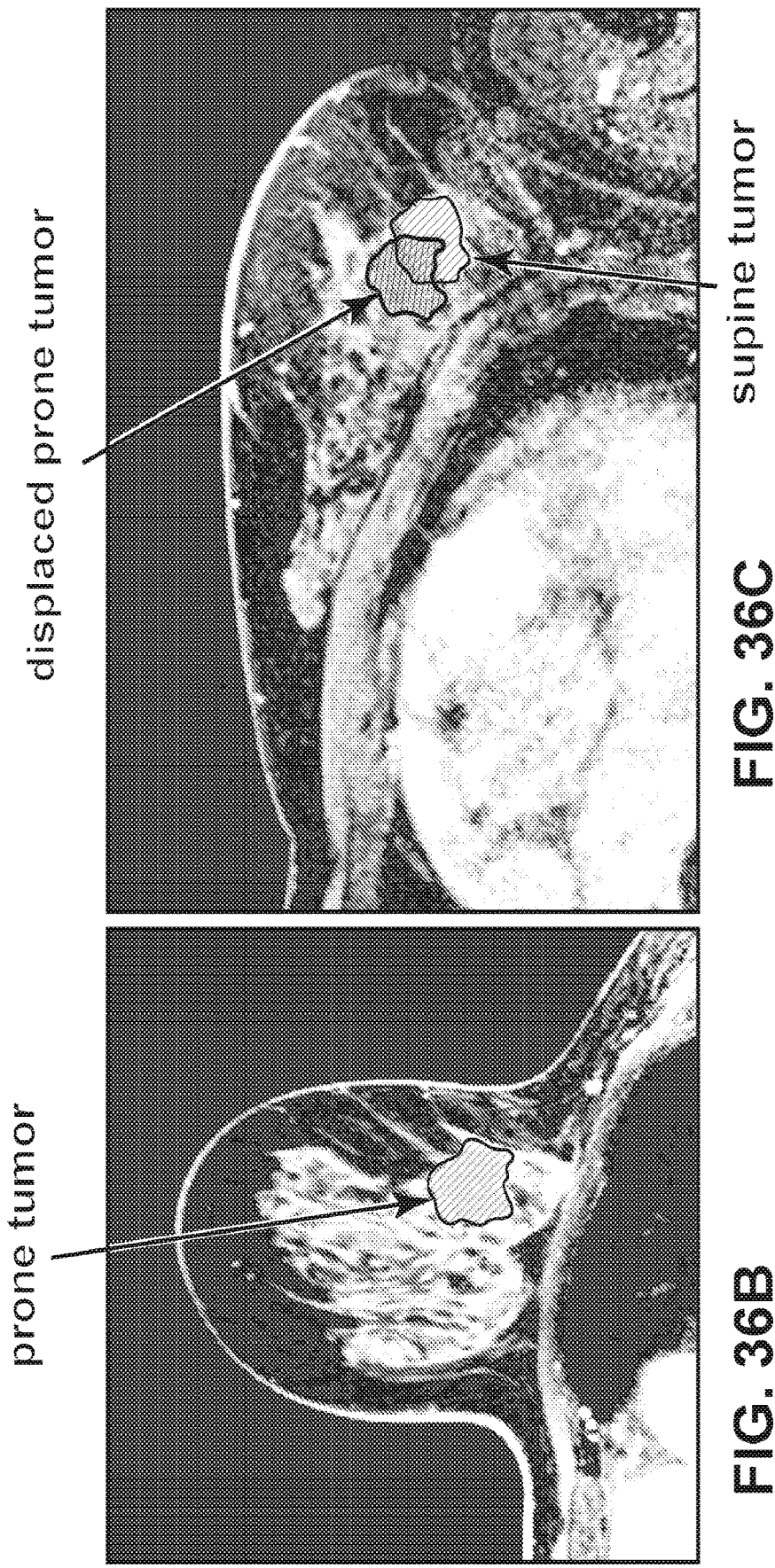
FIG. 36B is a mammogram showing positions of a tumor.
FIG. 36C is another mammogram showing positions of a tumor.

FIG. 36A shows signed distance of all mesh model vertices between displaced prone tumor and real supine tumor for the twenty cases. A negative distance suggests they overlap. FIGS. 36B and 36C show mammograms showing positions of tumors. FIG. 36B includes a prone tumor 880, and FIG. 36C includes a displaced prone tumor 882 and a real supine tumor 884.

Figure 37:
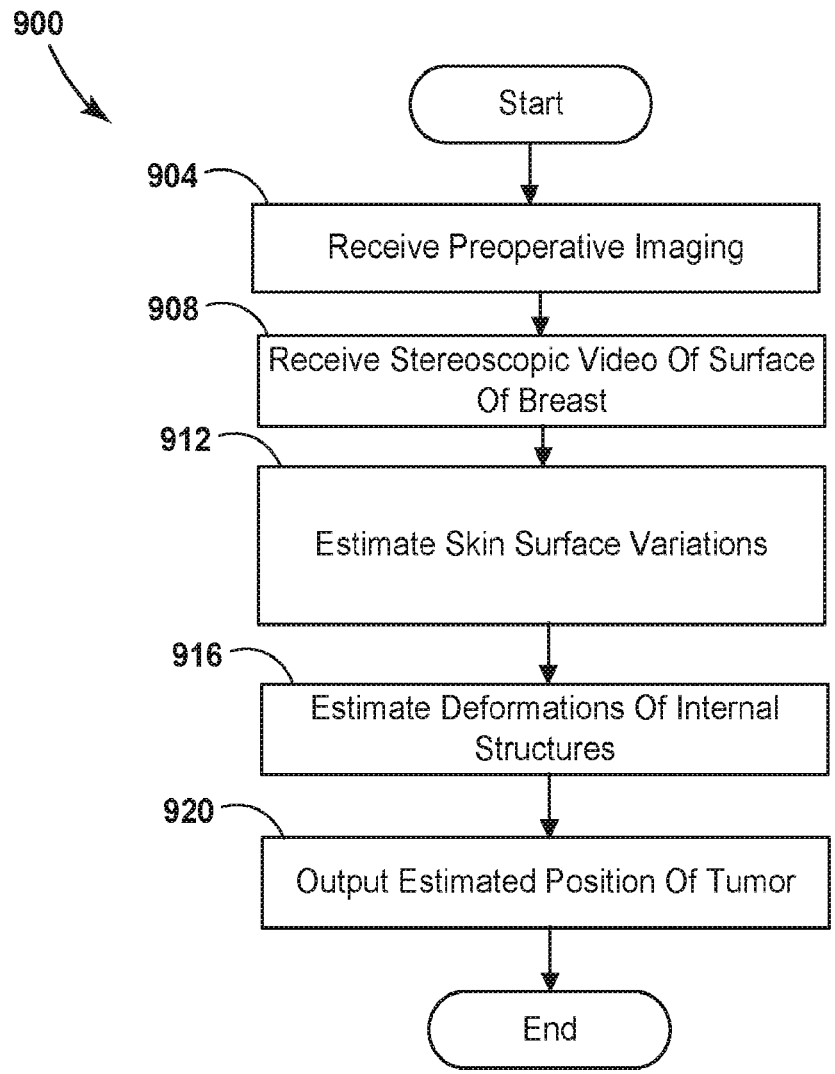
FIG. 37 is a flowchart a process for localizing a breast tumor based on skin surface variations.

FIG. 37 shows a process 900 for localizing a breast tumor based on skin surface variations.

At 904, the process 900 can receive preoperative imaging associated with a patient. The imaging can be performed using MRI, and can include segmentations of a tumor located in a breast of the patient, skin of the patient, and a chest wall of the patient. The preoperative process can also receive initial relative positions between the tumor and skin. The process 900 can then proceed to 908.

At 908, the process 900 can receive stereoscopic video of the surface of the breast. The process can then proceed to 912.

At 912, the process 900 can estimate breast skin surface variations based on the stereoscopic video. More specifically, as explained in the "Uniformly Sampling and Connections Generation" section, the process 900 can determine locations of surface particles of the breast. The process 900 can then proceed to 916.

At 916, the process 900 can estimate deformations of internal structures of the breast based on the surface particles. The process 900 can sum all forces that each particle receives and determine the final location of each particle (including particle associated with the tumor) using Equation (85). The process 900 can also determine an estimated location of the tumor. The process 900 can then proceed to 920.

At 920, the process 900 can output the estimated position of the tumor. The estimated position of the tumor can include the locations of the particles associated with the tumor. The process can then proceed to 908.

(1) In the surgical planning stage, we segment the tumor, skin and chest wall from preoperative MRI with the 3D Slicer software. (2) During the surgery, we estimate the breast skin surface variations using stereo computer vision methods or depth map reconstruction. We have already developed a very efficient 3D reconstruction and tracking method running on GPUs. (3) According to the initial relative positions between the tumor and skin obtained in step 1, and the current skin model reconstructed in step 2, we estimate deformations of breast internal structures to localize the tumor.

In this disclosure, we present a particle system-based method for real-time deformation of breast internal structures and further localization of the breast tumor. The methods proposed in this disclosure are important components of our lumpectomy intraoperative navigation system which first reconstructs and tracks the breast skin surface using stereo computer vision methods and then estimates deformation of internal tissues with the proposed methods. Evaluation experiments in this disclosure used supine MRIs as the benchmark since the true positions of tumor are known. However, supine MRIs are not the standard-of-care at most hospitals in the US. In our experiments we found that the proposed deformation method is more accurate when the tumor is closer to the skin. This is because the deeper the tumor is, the weaker relationship between the tumor and skin surface.

The FEA methods have the advantage of being able to handle deformations of objects with complex stiffness. For simple homogeneous objects, the PS methods are good alternative with much lower computational complexity. Many computer graphics applications, such as animation, have proved the feasibility of PS methods. Since the breast tissue is predominantly composed of fat tissue, the PS methods result in accurate estimation of the tumor position while the breast is deformed from the prone diagnostic to supine surgical position.

The present disclosure has been described in terms of one or more preferred embodiments, and it should be appreciated that many equivalents, alternatives, variations, and modifications, aside from those expressly stated, are possible and within the scope of the disclosure.

The invention claimed is:

1. A system for navigating an environment experiencing non-rigid motion, the system comprising:
   at least one imaging system including at least one camera configured to acquire imaging data from the environment;
   a processor configured to receive the imaging data from the at least one camera and programmed to provide a real-time display of the environment experiencing the non-rigid motion by:
      (i) selecting, from the imaging data, a three-dimensional-two-dimensional (3D-2D) correspondence as a control point for use in a perspective-n-point (PnP) problem to determine a position and orientation of the at least one camera from at least one known correspondence between 3D object points and their 2D image projections in the environment;
      (ii) reprojecting at least a selected number of the projections;
      (iii) determining a reprojection error for each of the projections;
      (iv) performing a weight assignment of reprojection errors to distinguish inliers and outliers;
      (v) repeating (i) through (iv) multiple times, wherein the weight assignment applied to outliers decreases during iterations to reduce an impact of outliers in the real-time display of the environment; and
   a display configured to display the real-time display of the environment experiencing the non-rigid motion.

2. The system of claim 1 further comprising applying a histogram voting process to select inliers.

3. The system of claim 2 further comprising using inliers selected using the histogram voting process as control points.

4. The system of claim 1 wherein the at least one imaging system includes at least one of a laparoscope, an endoscope, or a microscope.

5. The system of claim 1 wherein the at least one imaging system forms a steroscopic imaging system.

6. The system of claim 1 further comprising comparing the reprojection error to a threshold that distinguishes inliers from outliers.

7. The system of claim 6 wherein the threshold is a predetermined number of pixels.

8. A method for creating images of an environment experiencing non-rigid motion, the method including steps comprising:
   (a) controlling at least one camera to acquire imaging data from the environment;
   (b) selecting, from the imaging data, a three-dimensional-two-dimensional (3D-2D) correspondence as a control point for use in a perspective-n-point (PnP) problem to determine a position and orientation of the at least one camera from at least one known correspondence between 3D object points and their 2D image projections in the environment;
   (c) reprojecting at least a selected number of the projections;
   (d) determining a reprojection error for each of the projections;
   (e) applying a histogram voting process to select inliers;
   (f) performing a weight assignment of reprojection errors to distinguish the inliers form outliers;
   iteratively repeating steps (a)-(f), wherein the weight assignment applied to outliers decreases during iterations to reduce an impact of outliers in the real-time display of the environment; and
   displaying the images of the environment experiencing the non-rigid motion in real-time.

9. The method of claim 8 further comprising using inliers selected using the histogram voting process as control points.

10. The method of claim 8 wherein the at least one camera forms part of at least one of a laparoscope, an endoscope, or a microscope.

11. The method of claim 8 wherein the imaging data is steroscopic imaging data.

12. The method of claim 8 further comprising comparing the reprojection error to a threshold that distinguishes inliers from outliers.

13. The method of claim 12 wherein the threshold is a predetermined number of pixels.

14. A method for creating images of an environment experiencing non-rigid motion, the method including steps comprising:
   (a) controlling at least one camera to acquire imaging data from the environment;

(b) selecting, from the imaging data, a three-dimensional-two-dimensional (3D-2D) correspondence as a control point for use in a perspective-n-point (PnP) problem to determine a position and orientation of the at least one camera from at least one known correspondence between 3D object points and their 2D image projections in the environment;

(c) reprojecting at least a selected number of the projections;

(d) determining a reprojection error for each of the projections;

(e) performing a weight assignment of reprojection errors to distinguish the inliers form outliers;

iteratively repeating steps (a)-(e), wherein the weight assignment applied to outliers decreases during iterations to reduce an impact of outliers in the real-time display of the environment; and displaying the images of the environment experiencing the non-rigid motion in real-time.

15. The method of claim 14 further comprising applying a histogram voting process to select inliers.

16. The method of claim 15 further comprising using inliers selected using the histogram voting process as control points.

17. The method of claim 14 wherein the at least one camera forms part of at least one of a laparoscope, an endoscope, or a microscope.

18. The method of claim 14 wherein the imaging data is steroscopic imaging data.

19. The method of claim 14 further comprising comparing the reprojection error to a threshold that distinguishes inliers from outliers.

20. The method of claim 19 wherein the threshold is a predetermined number of pixels.

* * * * *

UNITED STATES PATENT AND TRADEMARK OFFICE
CERTIFICATE OF CORRECTION

PATENT NO. : 11,890,063 B2
APPLICATION NO. : 17/414640
DATED : February 6, 2024
INVENTOR(S) : Jayender Jagadeesan et al.

It is certified that error appears in the above-identified patent and that said Letters Patent is hereby corrected as shown below:

In the Specification

Column 10, Line 20, Eq. (8), "$\Sigma_{i=1,i\neq o}^{N}$" should be -- $\sum_{i=1,i\neq o}^{N}$ --.

Column 10, Line 35, Eq. (9), "$\sum_{i=1,i\neq 0}^{N}$" should be -- $\sum_{i=1,i\neq 0}^{N}$ --.

Column 11, Line 3, Eq. (12), "$\sum_{i=1,i\neq o}^{N}$" should be -- $\sum_{i=1,i\neq o}^{N}$ --.

Column 11, Line 15, Eq. (13), "$\sum_{i=1,i\neq 0}^{N}$" should be -- $\sum_{i=1,i\neq 0}^{N}$ --.

Column 11, Line 19, Eq. (19), "$\sum_{i=1,i\neq 0}^{n}$" should be -- $\sum_{i=1,i\neq o}^{N}$ --.

Column 12, Line 37, Eq. (20), "$\sum_{i=1}^{N}$" should be -- $\sum_{i=1}^{N}$ --.

Column 12, Line 62, "$P^{(k+1)}$" should be --$p^{(k+1)}$--.

Column 13, Line 42, "<(p-o$_1$, q-o$_1$)> <(p-o$_2$, 1-o$_2$)" should be --"$\angle$(p-o$_1$, q-o$_1$)> $\angle$(p-o$_2$, 1-o$_2$)--.

Column 15, Line 47, Eq. (25), "(1-p$_{inliers}^{s}$)" should be --$p_{inliers}^{s}$--.

Signed and Sealed this
Fourth Day of June, 2024

*Katherine Kelly Vidal*

Katherine Kelly Vidal
*Director of the United States Patent and Trademark Office*

CERTIFICATE OF CORRECTION (continued)  Page 2 of 4
U.S. Pat. No. 11,890,063 B2

Column 16, Line 7, Eq. (26), "$N_{inlier}^{(k)}$-$N_{inlier}^{(k-20)}$" should be -- $N_{inlier}^{(k)} - N_{inlier}^{(k-20)}$ --.

Column 16, Line 58, "($r_{k,true}^T \cdot r_k$)" should be -- $\left(r_{k,true}^T \cdot r_k\right)$ --.

Column 27, Line 20, Eq. (36), "$\lambda_i^* x_i - \lambda_o^* x_o$" should be -- $\lambda_i^* x_i - \lambda_o^* x_o$ --.

Column 27, Line 39, Eq. (39), "$\Sigma_{i=1,i\neq o}N$" should be -- $\sum_{i=1,i\neq o}^{N}$ --.

Column 29, Line 62, Eq. (48), "$J^T J = J_{BA}^T J_{BA} + \beta^2 J_{ICP}^T J_{ICP}$" should be -- $J^T J = J_{BA}^T J_{BA} + \beta^2 J_{ICP}^T J_{ICP}$ --.

Column 29, Line 64, Eq. (49), "$J^T b = J_{BA}^T b_{BA} + \beta^2 J_{ICP}^T b_{ICP}$" should be -- $J^T b = J_{BA}^T b_{BA} + \beta^2 J_{ICP}^T b_{ICP}$ --.

Column 29, Line 66, "off" should be --of J--.

Column 39, Line 41, Eq. (51), "$S_{k0}^l = [(o_1^l - o k_0^l, \cdots, o_N^l - o k_0^l 0]_{3\times N}, l=1,2$" should be
-- $S_{k0}^l = [(o_1^l - o_{k0}^l, \ldots, o_N^l - o_{k0}^l)]_{3\times N}, l=1,2$ --.

Column 39, Line 47, Eq. (52), "$S_{k0}^2(k) \approx : R S_{k0}^1(k)$" should be -- $S_{k0}^2(k) \approx R S_{k0}^1(k)$ --.

Column 39, Line 53, Eq. (53), "$\|S_{k0}^2(k) - R S_{k0}^1(k)\|$" should be -- $\| S_{k0}^2(k) - R S_{k0}^1(k) \|$ --.

Column 39, Lines 58-59, "$s_{ko}^1$ and $s_{ko}^2$" should be -- $S_{k0}^1$ and $S_{k0}^2$ --.

Column 40, Line 38, Eq. (55), "$\|p_{i2}^t - P_{i1}^r\| - \|p_{i2}^o - P_{i1}^0\|$" should be -- $\left\| p_{i2}^t - p_{i1}^t \right\| - \left\| p_{i2}^o - p_{i1}^o \right\|$ --.

Column 40, Line 40, Eq. (55), "$(W_{i1}^t(p_{i2}^o) - p_{i1}^t, p_{i2}^t - P_{i1}^t)$" should be -- $(W_{i1}^t(p_{i2}^o) - p_{i1}^t, p_{i2}^t - p_{i1}^t)$ --.

Column 40, Line 42, Eq. (55), "$\|W_{i1}^t(1,2,3,4) - W_{i2}^t(1,2,3,4)\|$" should be
-- $\| W_{i1}^t(1,2,3,4) - W_{i2}^t(1,2,3,4) \|$ --.

Column 40, Line 45, "$(p_{i2}^o) - p_{i1}^t$ and $-p_{i2}^t - p_{i1}^t$" should be -- $(p_{i2}^o) - p_{i1}^t$ and $p_{i2}^t - p_{i1}^t$ --.

Column 40, Line 45, "$W_{i1}^t(p_{i2}^o)$" should be -- $W_{i1}^t(p_{i2}^o)$ --.

CERTIFICATE OF CORRECTION (continued)  
U.S. Pat. No. 11,890,063 B2

Column 40, Line 46, "$W_{i1}{}^t$ to $p_{i2}{}^o$" should be -- $W_{i1}^t$ to $p_{i2}^o$ --.

Column 48, Line 6, Eq. (69), "$fx_i = \Sigma_{j=1}{}^N w^i{}_j g_j$" should be -- $fx_i = \Sigma_{j=1}^N w_j^i g_j$ --.

Column 48, Line 40, Eq. (72), "$\| \Sigma_{j=1}{}^N (w^i{}_j q_j) \|$" should be -- $\| \Sigma_{j=1}^N (w_j^i q_j) \|$ --.

Column 48, Line 42, Eq. (73), "$\Sigma_{j=1}{}^N (w^i{}_j \mu_j) / \Sigma_{j=1}{}^N$" should be -- $\Sigma_{j=1}^N (w_j^i \mu_j) / \Sigma_{j=1}^N$ --.

Column 49, Line 27, Eq. (77), "$w_{j,distance}{}^i p$" should be -- $w_{i,distance}^j p$ --.

Column 49, Line 29, "$w_{j,distance}{}^i$" should be -- $w_{i,distance}^j$ --.

Column 49, Line 37, "$w_{j,distance}{}^i$" should be -- $w_{i,distance}^j$ --.

Column 49, Line 45, Eq. (79), "$\sigma^2 = \Sigma_{i=1}{}^N$" should be -- $\sigma^2 = \Sigma_{i=1}^N$ --.

Column 49, Line 45, Eq. (79), "$/\Sigma_{i=1}{}^N p$" should be -- $/\Sigma_{i=1}^N p$ --.

Column 49, Line 63, Eq. (83), "$\sum_{i=1}^N$" should be -- $\Sigma_{i=1}^N$ --.

Column 50, Line 8, "$w_{j,distance}{}^i$" should be -- $w_{j,distance}^i$ --.

Column 50, Line 9, "$w_{j,distance}{}^i$" should be -- $w_{j,distance}^i$ --.

Column 51, Line 21, "$w_{j,distance}{}^i$" should be -- $w_{j,distance}^i$ --.

Column 51, Line 22, "a=1e-5" should be --α=1e-5--.

Column 53, Line 2, Eq. (84), "$\sum_{i=1}^N (x_i - \overline{x})^2 + \sum_{i=1}^N$" should be -- $\sum_{i=1}^N (x_i - \overline{x})^2 + \sum_{i=1}^N$ --.

Column 53, Line 6, "µ" should be --y--.

Column 53, Line 8, "a=2/s" should be --α=2-/s--.

CERTIFICATE OF CORRECTION (continued)
U.S. Pat. No. 11,890,063 B2

Column 57, Line 55, "$d_{i,j} \neq 0.75$" should be --$d_{i,j} \approx 0.75$--.

Column 58, Line 10, Eq. (92), "$F_{compress,i}^{ideal}$" should be --$F_{compress,i}^{ideal}$--.

Column 58, Line 14, "$F_{compress,i}^{ideal}$" should be --$F_{compress,i}^{ideal}$--.

Column 58, Line 18, "$F_{compress,i}^{ideal}$" should be --$F_{compress,i}^{ideal}$--.